US007169358B2

(12) United States Patent
Henkens et al.

(10) Patent No.: US 7,169,358 B2
(45) Date of Patent: Jan. 30, 2007

(54) ELECTROCHEMICAL DETECTION OF NUCLEIC ACID SEQUENCES

(76) Inventors: Robert W. Henkens, 169 N. Shore Dr., Beaufort, NC (US) 28516; John P. O'Daly, 112 Jasmine Ct., Carrbor, NC (US) 27510; Marek Wojciechowski, 102 Otterbein Ct., Cary, NC (US) 27513; Honghua Zhang, 12865 Caminito Diego, San Diego, CA (US) 92130; Najih Naser, 4123 Pescadero Ct., Orlando, FL (US) 32817; R. Michael Roe, 104 Bromfield Way, Apex, NC (US) 27502; Thomas N. Stewart, 4802 Glendarion Dr., Durham, NC (US) 27713; Deborah M. Thompson, 5909 Baird Dr., Raleigh, NC (US) 27606-9445; Rebecca Sundseth, 114 Settlers Mill La., Durham, NC (US) 27713; Steven E. Wegner, 204 Donegal Dr., Chapel Hill, NC (US) 27514

( * ) Notice: Subject to any disclaimer, the term of this patent is extended or adjusted under 35 U.S.C. 154(b) by 312 days.

(21) Appl. No.: 10/082,714

(22) Filed: Feb. 25, 2002

(65) Prior Publication Data
US 2004/0072158 A1    Apr. 15, 2004

Related U.S. Application Data

(60) Division of application No. 09/549,853, filed on Apr. 14, 2000, now Pat. No. 6,391,558, which is a continuation-in-part of application No. 09/044,206, filed on Mar. 17, 1998, now abandoned.

(60) Provisional application No. 60/040,949, filed on Mar. 18, 1997.

(51) Int. Cl.
| | | |
|---|---|---|
| G01N 15/06 | (2006.01) | |
| G01N 21/76 | (2006.01) | |
| G01N 21/00 | (2006.01) | |
| B32B 5/02 | (2006.01) | |
| C07H 21/00 | (2006.01) | |
| C12Q 1/68 | (2006.01) | |

(52) U.S. Cl. .......................... 422/68.1; 435/6; 422/52; 422/55; 422/82.1; 422/61; 536/23.1
(58) Field of Classification Search ................... 435/6; 422/52, 55, 61, 68.1, 82.1, 53; 536/23.1
See application file for complete search history.

(56) References Cited

U.S. PATENT DOCUMENTS

| 5,518,901 A | * | 5/1996 | Murtagh ..................... 435/91.2 |
| 6,063,259 A | * | 5/2000 | Wang et al. ............. 205/777.5 |
| 2002/0177135 A1 | * | 11/2002 | Doung et al. .................. 435/6 |
| 2004/0086423 A1 | * | 5/2004 | Wohlstadter et al. ......... 422/52 |

FOREIGN PATENT DOCUMENTS

EP        0407291 A1 *  1/1991

OTHER PUBLICATIONS

Stratagene catalog 1988, p. 39.*

* cited by examiner

*Primary Examiner*—Jezia Riley
(74) *Attorney, Agent, or Firm*—Akerman Senterfitt; Nicholas A. Zachariades

(57) ABSTRACT

An electrochemical detection system which specifically detects selected nucleic acid segments is described. The system utilizes biological probes such as nucleic acid or peptide nucleic acid probes which are complementary to and specifically hybridize with selected nucleic acid segments in order to generate a measurable current when an amperometric potential is applied. The electrochemical signal can be quantified.

14 Claims, 20 Drawing Sheets

SEQUENCE LISTING

```
<160> NUMBER OF SEQ ID NOS: 40

<210> SEQ ID NO 1
<211> LENGTH: 35
<212> TYPE: DNA
<213> ORGANISM: Escherichia coli

<400> SEQUENCE: 1
tcaatgagca aaggtattaa ctttactccc ttcct                           35

<210> SEQ ID NO 2
<211> LENGTH: 35
<212> TYPE: DNA
<213> ORGANISM: Escherichia coli

<400> SEQUENCE: 2
tgaaagtact ttacaacccg aaggccttct tcata                           35

<210> SEQ ID NO 3
<211> LENGTH: 25
<212> TYPE: DNA
<213> ORGANISM: Escherichia coli

<400> SEQUENCE: 3
gtctcacggt tcccgaaggc acatt                                      25

<210> SEQ ID NO 4
<211> LENGTH: 25
<212> TYPE: DNA
<213> ORGANISM: Escherichia coli

<400> SEQUENCE: 4
tctctgaaaa cttccgtgga tgtca                                      25

<210> SEQ ID NO 5
<211> LENGTH: 20
<212> TYPE: DNA
<213> ORGANISM: Artificial sequence
<220> FEATURE:
<223> OTHER INFORMATION: universal bacterial primer

<400> SEQUENCE: 5
agagtttgat cctggctcag                                            20

<210> SEQ ID NO 6
<211> LENGTH: 19
<212> TYPE: DNA
<213> ORGANISM: Artificial sequence
<220> FEATURE:
```

<223> OTHER INFORMATION: universal bacterial primer

<400> SEQUENCE: 6
ggttaccttg ttacgactt                                            19

<210> SEQ ID NO 7
<211> LENGTH: 32
<212> TYPE: DNA
<213> ORGANISM: Escherichia coli
<220> FEATURE:
<221> NAME/KEY: misc_feature
<222> LOCATION: (1)..(1)
<223> OTHER INFORMATION: Bound by a fluorescein moiety.
<220> FEATURE:
<221> NAME/KEY: misc_feature
<222> LOCATION: (2)..(2)
<223> OTHER INFORMATION: Bound by a fluorescein moiety that is present
      between nucleotides 1and 2.
<220> FEATURE:
<221> NAME/KEY: misc_feature
<222> LOCATION: (31)..(31)
<223> OTHER INFORMATION: Bound by a fluorescein moiety that is present
      between nucleotides 31and 32.
<220> FEATURE:
<221> NAME/KEY: misc_feature
<222> LOCATION: (32)..(32)
<223> OTHER INFORMATION: Bound by one 5' and one 3' fluorescein moiety.

<400> SEQUENCE: 7
tggagttagc cggtgcttct tctgcgggta at                             32

<210> SEQ ID NO 8
<211> LENGTH: 19
<212> TYPE: DNA
<213> ORGANISM: Homo sapiens

<400> SEQUENCE: 8
ctcctgagga gaagtctgc                                            19

<210> SEQ ID NO 9
<211> LENGTH: 19
<212> TYPE: DNA
<213> ORGANISM: Homo sapiens

<400> SEQUENCE: 9
gaggactcct cttcagacg                                            19

<210> SEQ ID NO 10
<211> LENGTH: 19
<212> TYPE: DNA
<213> ORGANISM: Homo sapiens

<400> SEQUENCE: 10
ctcctgtgga gaagtctgc                                            19

<210> SEQ ID NO 11
<211> LENGTH: 19
<212> TYPE: DNA
<213> ORGANISM: Homo sapiens

<400> SEQUENCE: 11
gaggacacct cttcagacg                                            19

<210> SEQ ID NO 12
<211> LENGTH: 21
<212> TYPE: DNA
<213> ORGANISM: Homo sapiens

```
<400> SEQUENCE: 12
ataacagatg ggctggaagt a                                              21

<210> SEQ ID NO 13
<211> LENGTH: 21
<212> TYPE: DNA
<213> ORGANISM: Homo sapiens

<400> SEQUENCE: 13
ataacagatg ggctggaagt a                                              21

<210> SEQ ID NO 14
<211> LENGTH: 19
<212> TYPE: DNA
<213> ORGANISM: Homo sapiens

<400> SEQUENCE: 14
gcggactccc agcacagaa                                                 19

<210> SEQ ID NO 15
<211> LENGTH: 19
<212> TYPE: DNA
<213> ORGANISM: Homo sapiens

<400> SEQUENCE: 15
gcggactccc agcacagaa                                                 19

<210> SEQ ID NO 16
<211> LENGTH: 24
<212> TYPE: DNA
<213> ORGANISM: Homo sapiens

<400> SEQUENCE: 16
tttctgaatg ctgctattta gtgt                                           24

<210> SEQ ID NO 17
<211> LENGTH: 24
<212> TYPE: DNA
<213> ORGANISM: Homo sapiens

<400> SEQUENCE: 17
tttctgaatg ctgctattta gtgt                                           24

<210> SEQ ID NO 18
<211> LENGTH: 24
<212> TYPE: DNA
<213> ORGANISM: Homo sapiens

<400> SEQUENCE: 18
catgaggatc actggccagt aagt                                           24

<210> SEQ ID NO 19
<211> LENGTH: 24
<212> TYPE: DNA
<213> ORGANISM: Homo sapiens

<400> SEQUENCE: 19
catgaggatc actggccagt aagt                                           24

<210> SEQ ID NO 20
<211> LENGTH: 43
<212> TYPE: DNA
```

<213> ORGANISM: Homo sapiens

<400> SEQUENCE: 20
gataatacga ctcactatag ggttttttgag taccttgtta ttt     43

<210> SEQ ID NO 21
<211> LENGTH: 42
<212> TYPE: DNA
<213> ORGANISM: Homo sapiens

<400> SEQUENCE: 21
gatttaggtg acactataga acgtttggtt agttccctga tt      42

<210> SEQ ID NO 22
<211> LENGTH: 25
<212> TYPE: DNA
<213> ORGANISM: Homo sapiens

<400> SEQUENCE: 22
cctgaggtgt agacgccaac tctct     25

<210> SEQ ID NO 23
<211> LENGTH: 24
<212> TYPE: DNA
<213> ORGANISM: Homo sapiens

<400> SEQUENCE: 23
actttgcaca tctcatgggg ttat      24

<210> SEQ ID NO 24
<211> LENGTH: 21
<212> TYPE: DNA
<213> ORGANISM: Homo sapiens

<400> SEQUENCE: 24
ataacagatg ggctggaagt a         21

<210> SEQ ID NO 25
<211> LENGTH: 19
<212> TYPE: DNA
<213> ORGANISM: Homo sapiens

<400> SEQUENCE: 25
gcggactccc agcacagaa            19

<210> SEQ ID NO 26
<211> LENGTH: 30
<212> TYPE: DNA
<213> ORGANISM: Homo sapiens

<400> SEQUENCE: 26 cattctttc tctcacacag gggatcagca  30

<210> SEQ ID NO 27
<211> LENGTH: 19
<212> TYPE: DNA
<213> ORGANISM: Homo sapiens

<400> SEQUENCE: 27 cattctttc tctcacaca             19

<210> SEQ ID NO 28
<211> LENGTH: 25

```
<212> TYPE: DNA
<213> ORGANISM: Homo sapiens

<400> SEQUENCE: 28
cctgaggtgt agacgccaac tctct                                    25

<210> SEQ ID NO 29
<211> LENGTH: 24
<212> TYPE: DNA
<213> ORGANISM: Homo sapiens

<400> SEQUENCE: 29
catcttgttg agggcagggg agta                                     24

<210> SEQ ID NO 30
<211> LENGTH: 29
<212> TYPE: DNA
<213> ORGANISM: Homo sapiens

<400> SEQUENCE: 30
atctctagga ttctctgagc atggcagtt                                29

<210> SEQ ID NO 31
<211> LENGTH: 30
<212> TYPE: DNA
<213> ORGANISM: Homo sapiens

<400> SEQUENCE: 31
acatcttcag tatctctagc atggcagttt                               30

<210> SEQ ID NO 32
<211> LENGTH: 20
<212> TYPE: DNA
<213> ORGANISM: Homo sapiens

<400> SEQUENCE: 32
ctctaggatt ctctgagcat                                          20

<210> SEQ ID NO 33
<211> LENGTH: 20
<212> TYPE: DNA
<213> ORGANISM: Homo sapiens

<400> SEQUENCE: 33
cagtatctct agcatggcag                                          20

<210> SEQ ID NO 34
<211> LENGTH: 16
<212> TYPE: DNA
<213> ORGANISM: Homo sapiens

<400> SEQUENCE: 34
agactcccca tcatgt                                              16

<210> SEQ ID NO 35
<211> LENGTH: 15
<212> TYPE: DNA
<213> ORGANISM: Homo sapiens

<400> SEQUENCE: 35
agactcccat catgt                                               15

<210> SEQ ID NO 36
```

-continued

```
<211> LENGTH: 24
<212> TYPE: DNA
<213> ORGANISM: Homo sapiens

<400> SEQUENCE: 36
catgaggatc actggccagt aagt                                              24

<210> SEQ ID NO 37
<211> LENGTH: 20
<212> TYPE: DNA
<213> ORGANISM: Homo sapiens

<400> SEQUENCE: 37
tcatgtgctg tgactgcttg                                                   20

<210> SEQ ID NO 38
<211> LENGTH: 15
<212> TYPE: DNA
<213> ORGANISM: Homo sapiens

<400> SEQUENCE: 38
gactccccat catgt                                                        15

<210> SEQ ID NO 39
<211> LENGTH: 20
<212> TYPE: DNA
<213> ORGANISM: Homo sapiens

<400> SEQUENCE: 39
ataccttatt ccattctttt                                                   20

<210> SEQ ID NO 40
<211> LENGTH: 30
<212> TYPE: DNA
<213> ORGANISM: Homo sapiens

<400> SEQUENCE: 40
atctctagga ttctctgagc atggcagttt                                        30
```

ELECTROCHEMICAL DETECTION OF NUCLEIC ACID SEQUENCES

Figure 1:
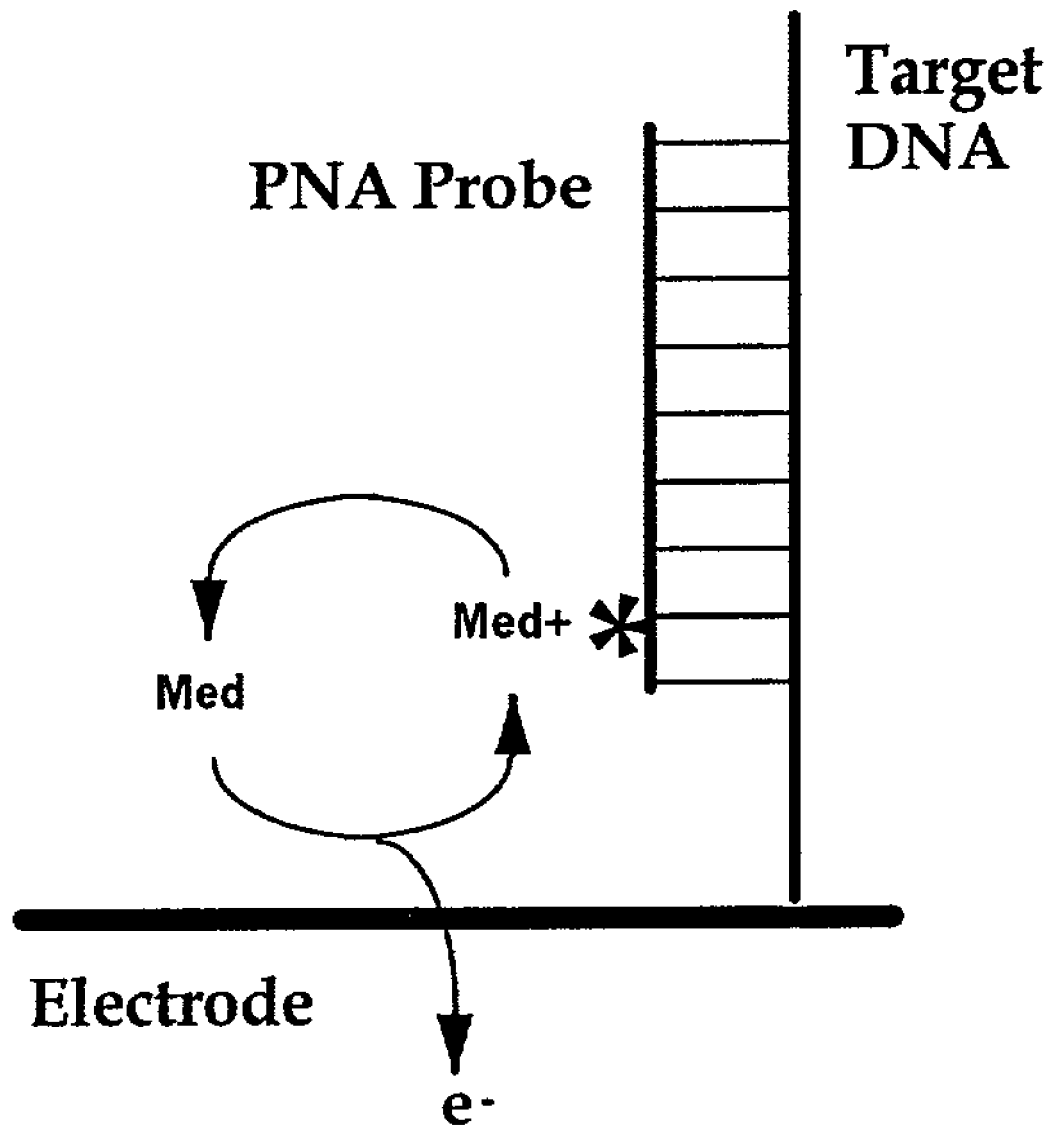

The application is a divisional application of patent application Ser. No. 09/549,853 filed Apr. 14, 2000 now U.S. Pat. No. 6,391,558 which is a continuation-in-part of patent application Ser. No. 09/044,206 filed Mar. 17, 1998 now abandoned which is a continuation-in-part of provisional patent application Ser. No. 60/040,949 filed Mar. 18, 1997, now abandoned, the entire contents of each application are herein incorporated without prejudice and without disclaimer.

The government owns rights in the present invention pursuant to contract number DAAM01-95-C-0077 from the Department of Defense.

1.0 BACKGROUND OF THE INVENTION

1.1 Field of the Invention

The present invention relates generally to the fields of sensor technology and molecular diagnostics. More particularly, it concerns the quantitative electrochemical detection of selected nucleic acid sequences in complex mixtures.

1.2 Description of Related Art

The determination of a specific DNA or RNA target nucleic acid sequence or segment present in air, food, water, environmental or clinical samples is of great significance in the medical, microbiology, food and water safety-testing, and environmental monitoring fields. The detection of the presence of a DNA or RNA sequence in a sample can rapidly and unambiguously identify genetic defects, oncogenic events and bacterial, viral or parasitic agents of concern.

Diagnosis of numerous infectious and inherited human diseases is possible with clinical assays that detect known DNA sequences characteristic of a particular disease (Molecular Diagnostics; 1993; Benn et al, 1987; Lowe, 1986). Unfortunately, few detection methods are suitable for routine diagnostic use either in the clinical laboratory or in the field setting. Many assays are not sufficiently rapid, inexpensive, simple or robust for routine application.

Recent advances in molecular diagnostics have focused on methods of detection at the genetic level. Since the advent of PCR™ technology, the ability to detect or identify point mutations, allelic variation, the presence of minute amounts of a pathogen, species, and from individual microscopic samples, to give a few examples, has been vastly improved. Yet even with the advances of PCR™ technology many limitations still exist which prevent diagnostic assays from being as versatile as desired or needed.

For example, one of the biggest problems with highly sensitive assays, such as PCR™ based assays, is contamination by extraneous air-borne organisms or by human contact. In general, if a molecular diagnostic assay is highly sensitive and can detect minute quantities of a selected or target nucleic acid segment, the sample to be assayed must be highly purified or at least not contain extraneous nucleic acid fragments which may be at least partially complementary to the target nucleic acid segment. Otherwise, false positive or ambiguous readings may result. Of course, obtaining highly purified samples is not cost ineffective due to time and labor involved. Strong technical expertise and well-equipped diagnostic laboratories are required in most cases. Thus in many instances where a highly sensitive assay is desirable, it is impractical, if not impossible, to perform such assays.

A variety of methods have been used to detect and quantitate polynucleotide sequences. Almost all of these begin with amplification of individual sequences or their transcripts by PCR. Some require separation by gel electrophoresis and/or laser detection. These needs Greatly complicate the development of good technology for scale-up, automation, and reduction of cost. Probe-array technologies are being developed by a number of companies—including Nanogen (San Diego, Calif.) and Affymetrix (Santa Clara, Calif.). The electrochemical methods described do not rely upon electrophoresis or laser technology, and can make use of DNA or PNA robes in arrays.

In cases where it is desirable to detect more than one target nucleic acid species in a sample, or the sample is highly complex, highly sensitive assays must be customized to detect the desired targets. Although not entirely understood, it is well known that many highly sensitive assays suffer from undue interference caused by background sample material. In fact, the time and labor required to develop some assays is so great that the assays are not useful and less sensitive means of analysis are employed.

Diagnostic assays that do not require high purity samples are less sensitive and therefore cannot detect minute amounts of target. Thus larger or more concentrated samples must be obtained. In some cases, larger sample quantities are not available or are too costly.

Probe assays, including oligonucleotide-probe and gene-probe assays, have been developed recently in an attempt to take advantage of the ability to detect selected DNA or RNA sequences with high sensitivity and replace conventional detection methods. However, these techniques still tend to be labor-intensive and often require significant technical training and expertise. Further, highly sensitive gene-probe assays require specialized equipment and are generally not compatible with field settings. Those that can be used in a field setting are limited to determining the presence or absence of a target nucleic acid fragment and do not provide quantitative information. The utility of gene-probe assays for environmental monitoring and other uses outside of a laboratory setting is limited.

Moreover, gene-probe assays may use a label that is either toxic or requires substantial expertise and labor to use. Radiolabeling is one of the most commonly used techniques because of the high sensitivity of radiolabels. But the use of radiolabeled probes is expensive and requires complex, time consuming, sample preparation and analysis and special disposal. Alternatives to radioactivity for labeling probes include chemiluminescence, fluorimetric and colorimetric labels (Kricka, 1993) but each alternative has distinct disadvantages. Colorimetry is relatively insensitive and has limited utility where minute amounts of sample can be obtained. Samples must also be optically transparent. Fluorimetry requires relatively sophisticated equipment and procedures not readily adapted to routine use. Chemiluminescence, although versatile and sensitive when used for Southern blots, northern blots, colony/plaques lift, DNA foot-printing and nucleic acid sequencing, is expensive, and is not well-adapted for routine analysis in the clinical laboratory.

Another limitation to the versatility of oligonucleotide-probe assays is that virtually all current oligonucleotide-probes are designed as heterogeneous assays, i.e., a solid phase support is used to immobilize the target nucleic acid so that free, non-hybridized probe can be removed by washing. Complex procedures and long incubation times (one to several days) are usually required which makes these assays difficult to incorporate into the simple and rapid formats that are desirable for clinical applications or on-site analysis (Molecular Diagnostics, 1993).

Various techniques exist for the detection of differential gene expression into closely matched cell populations. These include subtractive cloning (Sagerstrom et al., 1997, Differential Display (Liang and Pardee, 1992), serial analysis of gene expression (SAGE) (Velculescu et al., 1995), expressed sequence tags (ESTs) (Adams et al. 1991). While all of the above-mentioned approaches have yielded significant results most have drawbacks. Subtractive cloning, SAGE and ESTs tend to be labor intensive and costly and therefore not suitable for use on a routine basis. For example SAGE and ESTs entail the use of hundreds or thousands of DNA sequencing reactions. Recently the feasibility of hybridization based technology as well as its superiority to other screening process has been shown. The human genome project has identified new genes and unique ESTs at a rapid rate. As of Nov. 30, 1998 17,583 human genes or complete coding sequences had been identified and 52,277 unique ESTs had been cataloged. DNA microarray or gene chip technology has catalyzed further advances. The technology involves the positioning of highly condensed and ordered arrays of DNA probes on glass slides or nylon membranes. Up to 50,000 DNA fragments, each representing an individual gene can be placed on a single glass slide and up to 5,000 placed on a nylon membrane. The resulting microarrays can then be used to examine presence and levels of gene expression.

Alternatives to gene-probe and other assay methods of detecting nucleic acid sequences have employed electrochemical biosensors that employ intercalators and discriminate between immobilized single-stranded and double-stranded DNA (Hashimoto et al., 1994; Millan et al., 1994; Millan and Mikkelsen, 1993). While such biosensors are capable of detecting a known target DNA sequence, they are handicapped by the fact that the electrode must be cleaned between each use. The procedures used to strip away the hybridized target DNA from the electrode surface are not suitable for widespread screening applications, such as clinical diagnostics where labor and expense must be kept minimal and speed is essential, or in settings outside of the laboratory such as field testing.

DNA diagnostics have recently achieved importance because of the advances in molecular biology that have highlighted the importance of gene mutations and hereditary diseases. Many studies have focused on the breast cancer susceptibility gene BRCA1 which is estimated to account for a large fraction of hereditary breast cancer and the majority of familial breast/ovarian cancer. Over 111 unique BRCA1 mutations distributed throughout the gene have been described (Shatkuck-Eldens et al., 1995: Breast Cancer Information Core Database). Many methods have been used to screen for BRCA1 mutations. Almost all of these based on amplification of individual exons or their transcripts by PCR™ (Nollau and Wagener, 1997). All require separation by gel-electrophoresis. The need for electrophoresis greatly complicates scale-up automation and streamlining of procedures. A method that does not require electrophoresis (Affymetrix, Santa Clara, Calif.) is epifluorescence confocal scanning microscopy that utilizes high-density oligonucleotide arrays of over 96,000 oligonucleotides to scan 3,450 bases of exon 11 of BRCA1 (Hacia et al., 1996). Although it is powerful technique it is expensive and not readily available to most laboratories.

There are many human diseases associated with known gene alterations. These diseases include cystic fibrosis, muscular dystrophy, sickle cell anemia, phenylketonuria, thalassemia, hemophelia, α1-antitrypsin deficiency and lipoprotein metabolism disorders (Ben et al., 1987; Lowe, 1986; Landegren et al., 1988; Young et al., 1989; Kricka, 1993). Quantitative analysis of human genes is also useful for analysis of amplified oncogenes (Altitalo, 1987) and in a measurement of gene expression levels in tumors (Slamon et al., 1989). Genetic aspects of human diseases contributed by factors such as BRCA1, BRCA2 and p53 mutations all of which confer high cancer risk would benefit from gene analysis as would mutational changes in genes caused by chemical radiation.

Breast cancer is considered to have a hereditary cancer risk component. Among women who have a blood relative with the disease the risk of developing breast cancer is 1 in 5. Two mutated genes increase a woman's chances of developing breast cancer and genetic tests for detecting women at greatest risk have been used clinically.

Several genes in have been associated with the pre-disposition to cancer. These include BRCA1, p53, RBI and APC which are just a few of the more than 20 genes identified that are associated with the pre-disposition to cancer (Fearon, 1997; Ponder, 1997). The BRCA1 gene and its expressed protein as it relates to diagnosis and potential treatment of disease, has utility in diagnosis and potential disease treatments.

Clearly, there is a need for improved detection of nucleic acid sequences. Unfortunately, few assays are currently available for routine monitoring and/or diagnostic use because of the expense, complexity and/or physical limitations which prevent their use outside of a well-equipped laboratory. As discussed, the few existing assays that have limited applications and do not meet the diverse needs of clinical diagnostics and field testing.

2.0 SUMMARY OF THE INVENTION

The present invention seeks to address these and other deficiencies inherent in the prior art by providing simple and sensitive electrochemical methods of detecting virtually any type of nucleic acid sequence or segment, provided the target nucleic acid has been identified. The target nucleic acid sequences are detectable in synthetic and natural environments by capturing target nucleic acid sequences at the surface of an electrochemical sensor through hybridization with specific nucleic acid probes and subsequent triggering of an electrochemical reaction that generates current.

In preferred embodiments, the invention comprises a biosensor array having a plurality of both working and reference electrodes formed on a circuit board. The working electrodes are linked or attached to bioreporter molecules that are typically a protein or a nucleic acid, including peptides, polypeptides and peptide nucleic acids. The proteins may be antigens or antibodies, protein variants or functional derivatives. Virtually any protein or peptide may be used as a bioreporter, including enzymes with a variety of functions, e.g., reductases, peroxidases or phosphatases. The nucleic acids may be oligonucleotides, such as a DNA or RNA, including mRNAs, rRNAs and tRNAs.

In a particularly preferred embodiment, the plurality of working and reference electrodes of the biosensor array are comprised on a printed circuit board, preferably screen printed, with a plurality of labeled nucleic acid segments are attached to the surface of the working electrodes. The labeled segments will generate an electric current when an electric potential is applied to the working electrode after the attached labeled nucleic acid segments are hybridized or annealed with a target nucleic acid. Of course a plurality of labeled proteins, peptides, polypeptides or protein nucleic acids may likewise be attached to the working electrode and will produce an electric signal under similar conditions subsequent to binding or combining with a selected Substrate or receptor. The attached nucleic acids or other molecules attached to the working electrode need not be identical and each different labeled nucleic acid may, for example, bind to a different target nucleic acid.

An electric potential applied to the working electrodes may be applied with a multiplexed potentiostat. This allows measurement of any current produced on binding of the attached nucleic acid or other substance binding with a target molecule in situations where each labeled nucleic acid is hybridized to a different target and each generates a current.

The biosensor electrodes will be connected or operably linked to an electrochemical pulse analyzer which provides an electrical potential to the working electrode and also detects any signal produced by the bioreporter molecule as a result of sending an electrical pulse across the working electrode. The electrical pulse may be provided by a potentiostat may generate a current from the bioreporter under conditions where the bioreporter combines with a target molecule.

The working electrodes may be carbon or metal electrodes, including gold, silver, platinum, iridium, mercury, nickel, copper, palladium or colloidal forms of these metals such as colloidal gold, colloidal silver, colloidal carbon or combinations of these materials. The particular electrodes will be chosen to some extent for their ability to attach a selected reporter. In certain cases it will be advantageous to coat the electrode surface with a material that will increase binding of a reporter molecule. Typical surface coatings on gold or colloidal gold, for example, include avidin, streptavidin, protein G, protein A and NeutrAvidin. A preferred working electrode is a gold or colloidal gold electrode surface coated with biotin, digoxigenin or NeutrAvidin that attaches to a short nucleic acid segment specifically bounds or hybridized with a species specific region of a DNA or RNA. Nuclei acid segments are conveniently about 15 to about 25 bases in length, e.g. SEQ ID NO:8 and SEQ ID NO:9. The electrodes are useful in detecting plant, animal, and mammalian DNA or RNA and targeted nucleic acid sequences from microbes and vertebrates, including humans The type of coating will of course determine the nature of the attachment to a reporter molecule. Generally this will be a link arising from chemical crosslinking, covalent bonding but may also be from charge-charge interaction or adsorption.

The biosensor is preferably small in size for easy handling, and the working electrode may have a surface area from about 0.001 mm$^2$ to about 100 mm$^2$. The array may comprise several sample wells including 4, 96, 384, 1536-well configurations or larger; however, the 96-well array is currently convenient for most applications.

In a most preferred embodiment, the circuits are screen printed. Printed circuit-board technology may be employed to photolithograph the circuit onto a board. Where screen printed circuits are employed, a preferred embodiment is screen printed of carbon and silver over the working electrodes in the biosensor array in the area around the sample wells or where the sample is applied to the circuit board.

Bioreporters may be selected to recognize a single target molecule or several different bioreporters may be used in the same array, each specific for a different target molecule. Of course one may wish to utilize several reporters that each recognize the same molecule to assure that the target molecule is detected. Target molecules may be in separate or multiple samples that are applied to the multiple array for analysis.

Target molecules will be selected that can be recognized and will attach to the bioreporter. Depending on the types of molecules, attachment may be by hybridization, annealing, charge-charge interaction, hydrophobic or covalent bonding. Generally, the targets are oligonucleotides, including DNA, mRNA, rRNA, tRNA or PNAs. Of particular interest are the many ESTs available that may be useful as bioreporter targets in identifying new genes. Target molecules will typically include mRNA expressed from any of a number of microorganisms, pathogens and mutant genes. Examples include mRNA from *E. coli, Salmonella, Chlamydia, Neisseria*, polio virus and *Vibrio*. The biosensor may also be used to detect mRNA expressed form an APOAI BRCAI, p53) or sickle cell human β-globin gene. DNA deletions, insertions and single base changes in human and animal genes are also detectable. The source of nucleic acid, whether DNA or RNA, may be from humans, animals or plants.

The biosensor may comprise an apparatus or be used in a system that includes the necessary components for detecting and measuring a signal produced by one or more bioreporters. An apparatus will comprise integrated circuit including the biosensor array combined with a power supply and a detector. Such integrated circuits are known to those of skill in the art. Systems including the biosensor array may additionally include means for measuring an electrochemical signal after a potential is applied across a working electrode. Applying the electrical potential and measuring the electrochemical signal are conveniently accomplished with a programmed processor.

The signal to be detected from the bioreporter is measured by pulse amperometry, preferably by intermittent pulse amperometry or differential pulse amperometry.

Alternatively, the biosensor need not comprise a plurality of working and reference electrodes but may comprise a single working electrode and a single reference electrode. Whether in an array or a single working electrode, the biosensor may optionally include one or more counter electrodes.

The methods and apparatus herein disclosed are particularly suitable for the detection of infectious disease organisms; for example malaria, enterobacteria, viruses such as dengue, hantavirus, encephalitis virus, filovirus as well as *Brucella, Clostridium*, anthrax and plague causing microorganisms. Additionally, the method is suitable for the rapid detection of altered gene sequences and heterozygous mutations. Assays for breast cancer sequence mutation, point mutations in the Factor V gene, detection of disease-associated mRNAs and detection of low levels of circulating K ras tumor DNA in blood plasma are also within the scope of the invention. Selective detection of the polio virus, hepatitis A virus, rotavirus, and liver-associated mRNA has been achieved with the disclosed method.

An important aspect of the invention is the use of the disclosed biosensor and biosensor arrays and apparatus to detect and identify target molecules. One therefore will select an appropriate bioreporter molecule to attach to one or more working electrodes based on a selected target molecule. The working electrode is comprised within a circuit that will generate a current when an electric signal is applied to the working electrode and after the bioreporter has interacted with the target molecule. Preferably, the electrical signal is a pulsed signal. The resulting current is indicative of the presence of the target molecule and may be quantitatively related to the amount of target molecule detected.

The target molecule may be from any of a variety of sources, including microorganisms, plants or mammals and particularly from pathogens such as *E. coli, Salmonella,*

*Chalmydia, Neisseria*, polio virus and *Vibrio*. Preferably, the targets are proteins, peptides, polypeptides or nucleic acids, including DNA, mRNA, tRNA or rRNA. The method readily detects deletions, insertions or single base alterations in DNA. This has been exemplified with human BRCA1 and sickle cell human β-globin gene.

Methods for detecting a target nucleic acid sequence may include additional steps to further enhance detection and measurement of the target. A hybridized target nucleic acid, hybridized with the bioreporter (capture) molecule and/or detector probe, may be incubated with precursor-DNA or RNA nucleotide bases to extend the length of the hybridized target. This is accomplished with a single primer if desired. Where a reporter and a detector probe are employed, the bioreporter probe may be 3'-end blocked and the detector probe may have a 3'-hydroxyl group. Alternatively, the bioreporter may be extended before hybridization with the target molecule. The precursors may be labeled, for example with fluorescein or other fluorescent label.

Methods of a nucleic acid are another important aspect of the invention using the disclosed system. In this case, one prepares or obtains a capture probe complementary to a first selected region of the target nucleic acid. The capture probe is attached to the surface of a working electrode. A labeled detector probe is obtained and this probe is complementary to a second selected region of the target nucleic acid. The target nucleic acid which may be a DNA or an RNA, is then incubated with the capture and detector probes, separately or together, under conditions that allow or promote hybridization or annealing of the target with both the capture and the detector probes. The incubation step in many cases will be performed at an elevated temperature, preferably at or near the melting point temperature of the target/probe hybrid.

The amount of target nucleic acid may be extremely low and in such cases amplification may be advisable. One method may then utilize additional steps by generating a PCR-amplified double-stranded nucleic acid with a forward primer and a 5'-phosphate-modified reverse primer positioned outside a selected of a target nucleic acid. The double-stranded nucleic acid molecule will then be digested with an exonuclease, preferably lambda exonuclease, in order to degrade the 5'-phosphate modified strand. This results in a single strand target nucleic acid which is then detected as described. The forward primer may optionally be modified with biotin, or 5'-modified with phosphate and the reverse primer optionally modified with biotin or a functionally equivalent protein.

The method is readily applied to detection of mutations in nucleic acid sequences. In a preferred embodiment, a nucleic acid segment from a genomic DNA sample is amplified and the resulting double-stranded DNA digested with an exonuclease, preferably lambda exonuclease. The resulting single-stranded DNA is hybridized to a labeled detector probe and a labeled capture probe and then attached to the surface of an electrode. The mutation is detected by the electrochemical method described. Mutations in BRCA1 gene and a single base in sickle cell anemia gene have been detected with this method.

An important aspect of the disclosed methods is the use of differential pulse amperometry for the detection and quantitation of a target molecule. This procedure includes applying a first potential to the working electrode. The potential applied is preferably close to or at the open circuit potential. A second shorter potential is then applied to the working electrode to oxidize or reduce any reporter molecules at or near the working electrode surface. The difference between the current measured close to the end of each pulse then can be used to indicate the presence of the hybridized target nucleic acid.

Intermittent pulse amperometry is yet another preferred step in the detection of a target nucleic acid. A pulse of potential is directed to the working electrode to which a target/capture or target/reporter molecule is attached. The reporter or capture molecule is electrochemically oxidized or reduced. The working electrode is then disconnected from the potentiostat circuit for a period at least as long as the applied pulse which may be applied for a period of time from about 0.1 millisecond to about 100 milliseconds. Pulse separation time is from 1 millisecond to about 10 seconds. The measured current generated by each pulse can be related to the amount of target nucleic acid present.

Alternatively, the capture probe may be hybridized to the target molecule in solution, then attached to the working electrode. The detector probe is then hybridized with the hybridized capture/target nucleic acid. The capture probe may be labeled with avidin, streptavidin, NeutrAvidin, protein G, protein A or biotin which attaches to the working electrode surface. The detector probe may be labeled with fluorescein, digoxigenin, horseradish peroxidase, alkaline phosphatase or the like. The electrode surface is typically gold, colloidal gold, carbon or screen-printed conductive ink and may include an oligonucleotide or protein that will bind with the capture probe. The capture probe and the detector probes will bind with the target nucleic acid; either may be annealed across a deletion, insertion or single base alteration in the target.

2.1 Detection of Pathogens

By using specific sequences of DNA or RNA that are characteristic of target microbes, pathogens can be unambiguously identified, regardless of their cultivable states, by direct analysis of contaminated food or water samples. As used herein, "microbes" is intended to include unicellular organisms, eukaryotic cells, bacteria, viruses, cyanobacteria, fungi, yeast, molds, prions and archebacteria. Definitive data may be obtained regarding food and water quality, and the time-consuming culturing step associated with coliform counts is reduced or eliminated. In addition, distinctions can be made between different coliform bacteria, e.g. pathogenic v. nonpathogenic bacteria.

Examples of pathogens that can be detected using the invention include, but are not limited to, bacteria such as *Salmonella* sp., *Escherichia coli*, *Klebsiella pneumoniae*, *Bacillus* sp., *Shigella* sp., *Campylobacter* sp., *Helicobacter pylori*, *Vibrio* sp., *Chlamydia*, *Giardia*, parasites such as *Naegleria* and *Acanthamoeba* and viruses such as *Hepatitis* and *poliomyelitis*.

2.2 Detection of Genetic Variations

The invention may be employed to detect genetic variations associated with different disorders or diseases. Examples of diseases that can be detected include cystic fibrosis, muscular dystrophy, sickle cell anemia, phenylketonuria, thalassemia, hemophilia, $a_1$-antitrypsin deficiency, disorders of lipoprotein metabolism and inherited forms of cancer. In addition, quantitative analysis of human genes is also desirable for analysis of amplified oncogenes (Altitalo, 1987), detection of genetic defects and in the determination of gene expression levels in tumors (Slamon et al., 1989).

Cell samples may be from biological or clinical sources which are first lysed to free nucleic acid sequences into an aqueous medium and then allowed to hybridize with capture and detector probes that incorporate the respective characteristic target nucleic acid sequences. An electrochemical signal is generated by the hybridized probes/nucleic acid sequences and detected with an electrode biosensor. In certain cases, electron transfer mediator and an electroactive reporter group may be used to facilitate generation of an electrochemical signal.

2.3 Kits

Easy-to-use kits also form part of the invention. Such kits contain monitors, reagents and procedures that can be utilized in a clinical or research setting or adapted for either the field laboratory or on-site use. In particular, kits comprising the disclosed biosensor or biosensor array, or an apparatus comprising the biosensor in an integrated chip form, or a system that includes any of a number of means for detecting the captured target molecule and measuring the electrochemical signal produced subsequent to target capture, along with appropriate instructions, are contemplated. Kits comprising electrodes with one or more capture or reporter probes attached to the electrode surface where the probes are hybridizable with selected nucleic acid segments, one or more detector probes capable of hybridizing with a nonselected segment of the target nucleic acid along with instructions for use of the electrode or electrodes to electrochemically detect the selected target nucleic acid are also contemplated. An electrode with a 15–25 base oligonucleotide that selectively hybridizes or anneals with a targeted nucleic acid is a preferred embodiment.

The kits can be widely employed in less technologically developed areas or countries which do not have well-equipped laboratories and at remote sites far from well-equipped laboratory facilities. The invention thus is useful in monitoring for the presence of selected nucleic acids indicative of human health concerns (pathogens, genetic defects) at small laboratories, physician's offices, bedsides, and field locations.

2.4 Screening Methods

The invention further provides a screening system for rapid detection of genetic polymorphisms and small mutations scattered throughout long coding regions of the gene. The method takes advantage of inherent differences in the melting temperature of DNA strands which are perfectly homologous and comparing these to duplexes containing mismatched deleted or inserted base pairs. Depending on the extent of homology and the length of the DNA probe, the temperature at which a target probe hybrid will melt can differ by several degrees. The ability to electrochemically differentiate the melting temperatures of sample and reference for different regions of a gene provides a method to screen for mutations- or polymorphisms using probes for any stretch of DNA for which the DNA sequence is known. The disclosed electrochemical differential thermal scanning approach permits rapid detection as well as the ability to localize differences between a standard reference gene and the gene rather than require de novo determination of the complete sequence of each sample.

The screening method also takes advantage of the disclosed technology to identify candidate drugs for modulating cell function. The putative drug candidate is incubated with a cell culture selected as being of interest in some therapeutic area such as antibiotic utility. Nucleic acids are extracted from the cells after the incubation and hybridized with a selected array of nucleic acid segments prepared on the disclosed biosensor array. The selected nucleic acids are bioreporter or capture probes prepared from nucleic acids with known functions, e.g., metabolic enzyme mRNAs from a pathogen. Detection and quantitation can be performed as described by applying a pulsed electrical potential to the biosensor array. A comparison of the "library" of nucleic acids from the putative drug treated cell culture with the library obtained from a cell culture without the putative drug will be indicative of a substance that affects cell function. Generally the nucleic acids to be detected will be mRNAs. One application will be to determine the effect of potential drugs on mRNA expressed from ApoA1, p53), BRCA1 and other genes associated with cancer as well as genes associated with mutated genes. The screening method may also be of use in targeting substances to mRNAs associated with gene expression in individuals with inborn errors of metabolism.

2.5 Detection of PCR Amplified Products

In another embodiment, the disclosed invention can be coupled to polymerase chain reaction (PCR™) or other nucleic acid amplification methods. Thus, DNA from a pathogen may be amplified or the RNA from a pathogen may be reverse transcribed (RT) and then amplified or amplified directly, and the amplified product detected electrochemically in accordance with the invention. The amplification and detection may be employed to increase the concentration of a pathogen for purposes of detection, or to follow the progress of an amplification reaction.

In an illustrative example, the disclosed methods may be used to detect and quantify a double-stranded PCR™ product by tagging one strand and binding that strand to a NeutrAvidin-coated biosensor, and by tagging the other strand with fluorescein and reacting that strand with an anti-fluoresein HR-P conjugate. Promptly following the addition of a peroxide and a mediator such as ferrocene to the PCR™ product, in an electrochemical cell in accordance with the invention, an amperometric signal is generated and may be detected.

Confirmation of the product may be accomplished by first denaturing the fluorescein labeled strand from the hybrid with base. The captured (biotin-labeled) strand may be verified by forming a second hybrid with a known fluorescein-labeled probe, followed by electrochemically detecting the hybrid.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Schematically illustrates PNA probe attachment to target DNA attached to electrode surface.

Figure 2A:
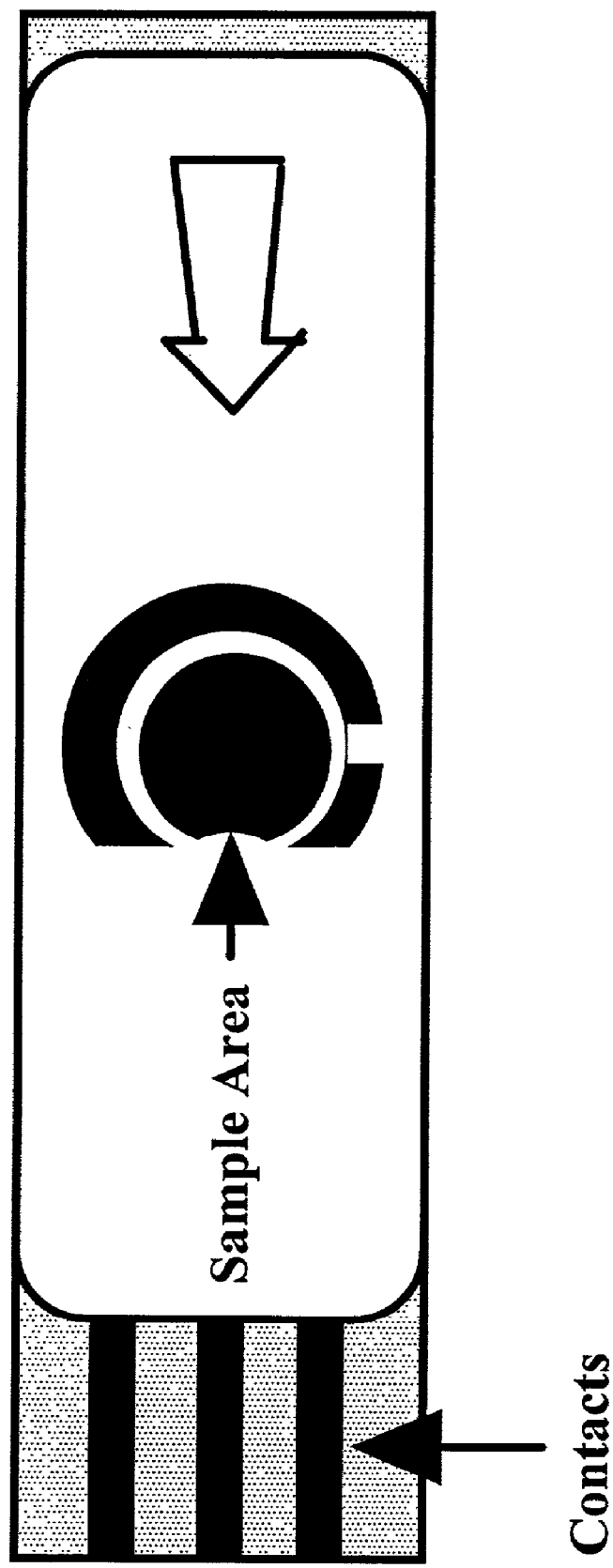
Figure 2B:
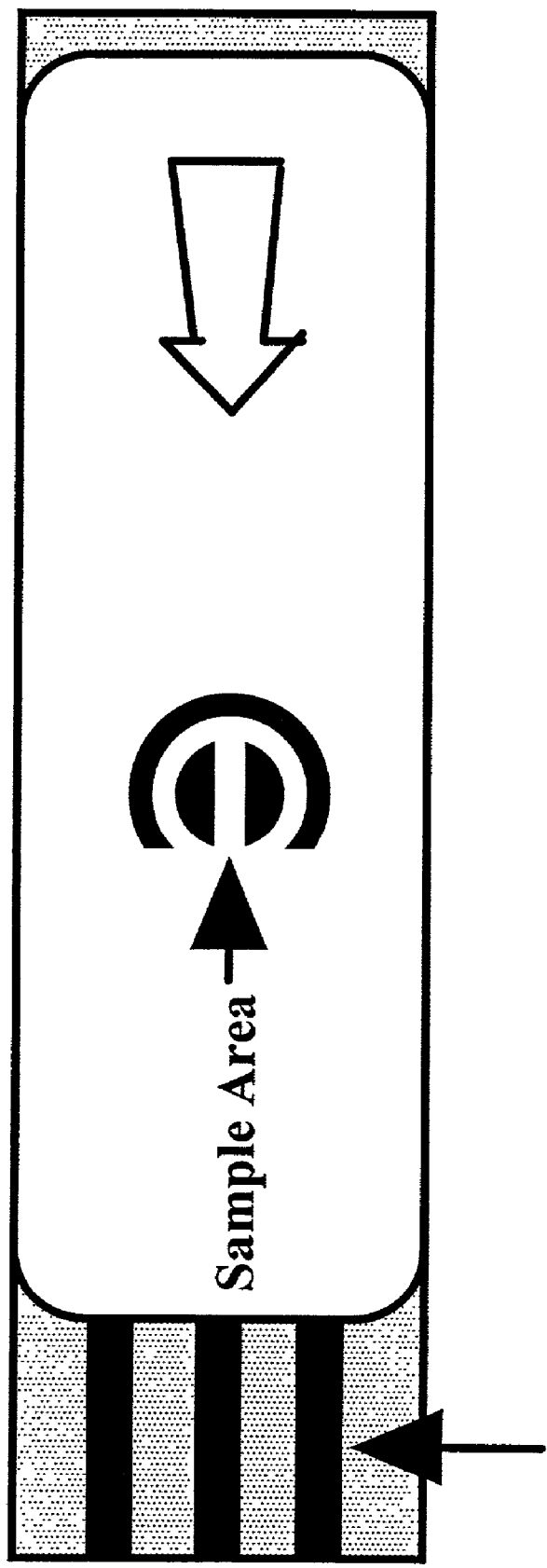

FIG. 2A. Exemplary embodiment of screen printed biosensor strip with one working electrode sensor;

FIG. 2B. Exemplary embodiment of screen printed biosensor strip with two working electrode sensors.

Figure 3:
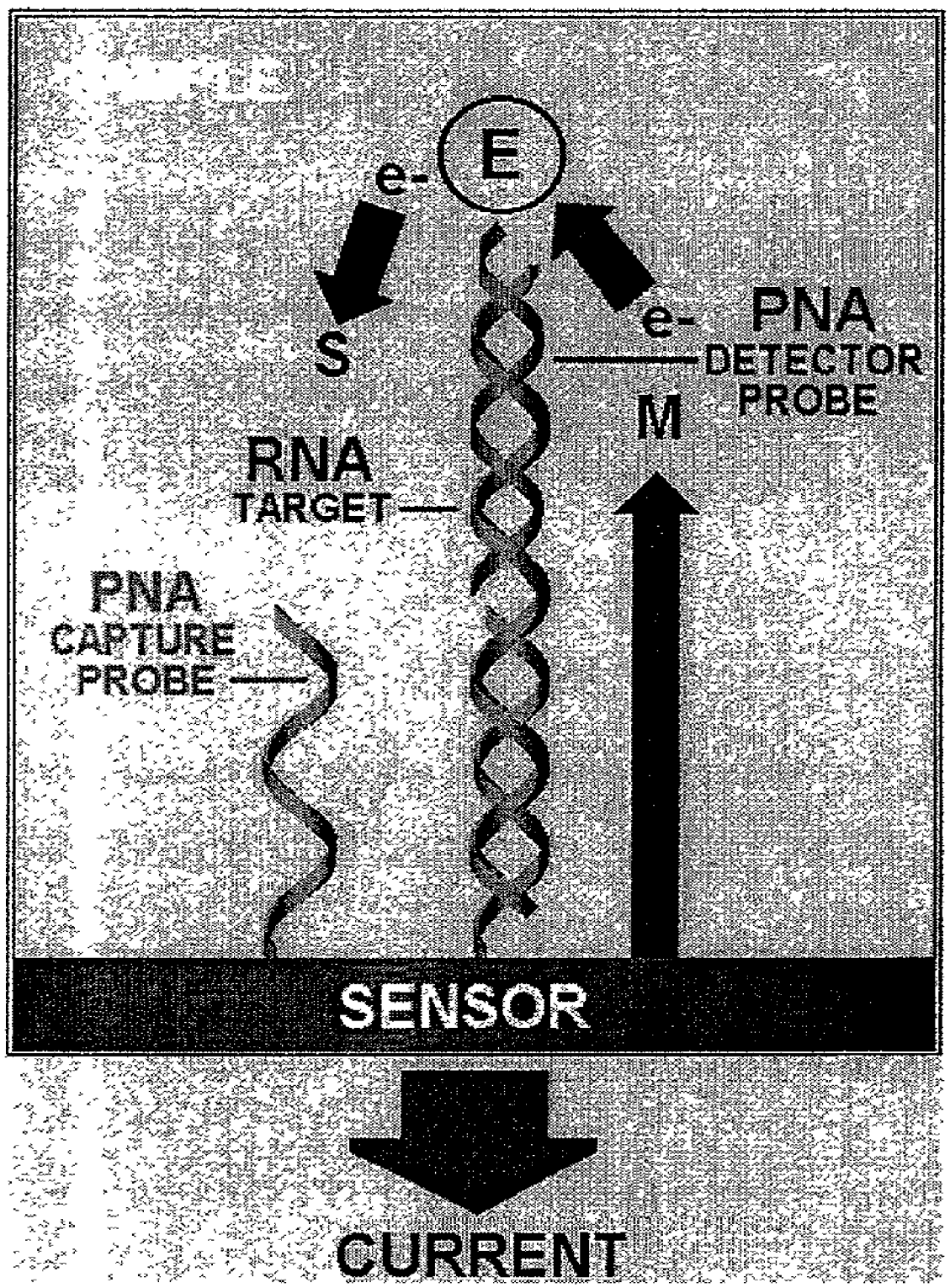

FIG. 3. Schematically illustrates the electrochemical measurement. E represents a redox-active enzyme; M represents an electroactive mediator; and S is the enzyme substrate. The arrows show electron flow during reduction of S. When a potential is applied to the sensor electrode, electrons (e−) are removed from the sensor by M which carries the electron from a solid electrode to accomplish enzyme-catalyzed reduction of S, producing a current.

Figure 4:
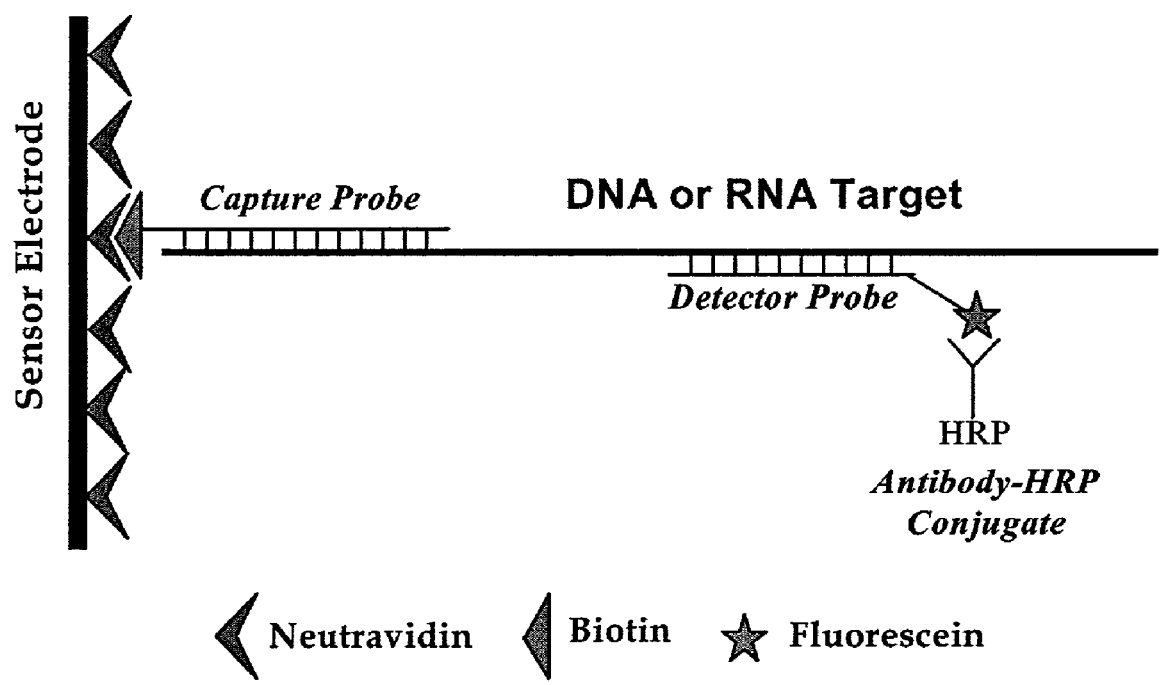

FIG. 4. Schematic illustration of the target nucleic acid sequence hybridized by capture and detector probes and bound at a Neutravidin-modified surface of a gold working electrode. A potential is then applied and current measured, thus detecting and measuring the target nucleic acid sequence.

Figure 5:
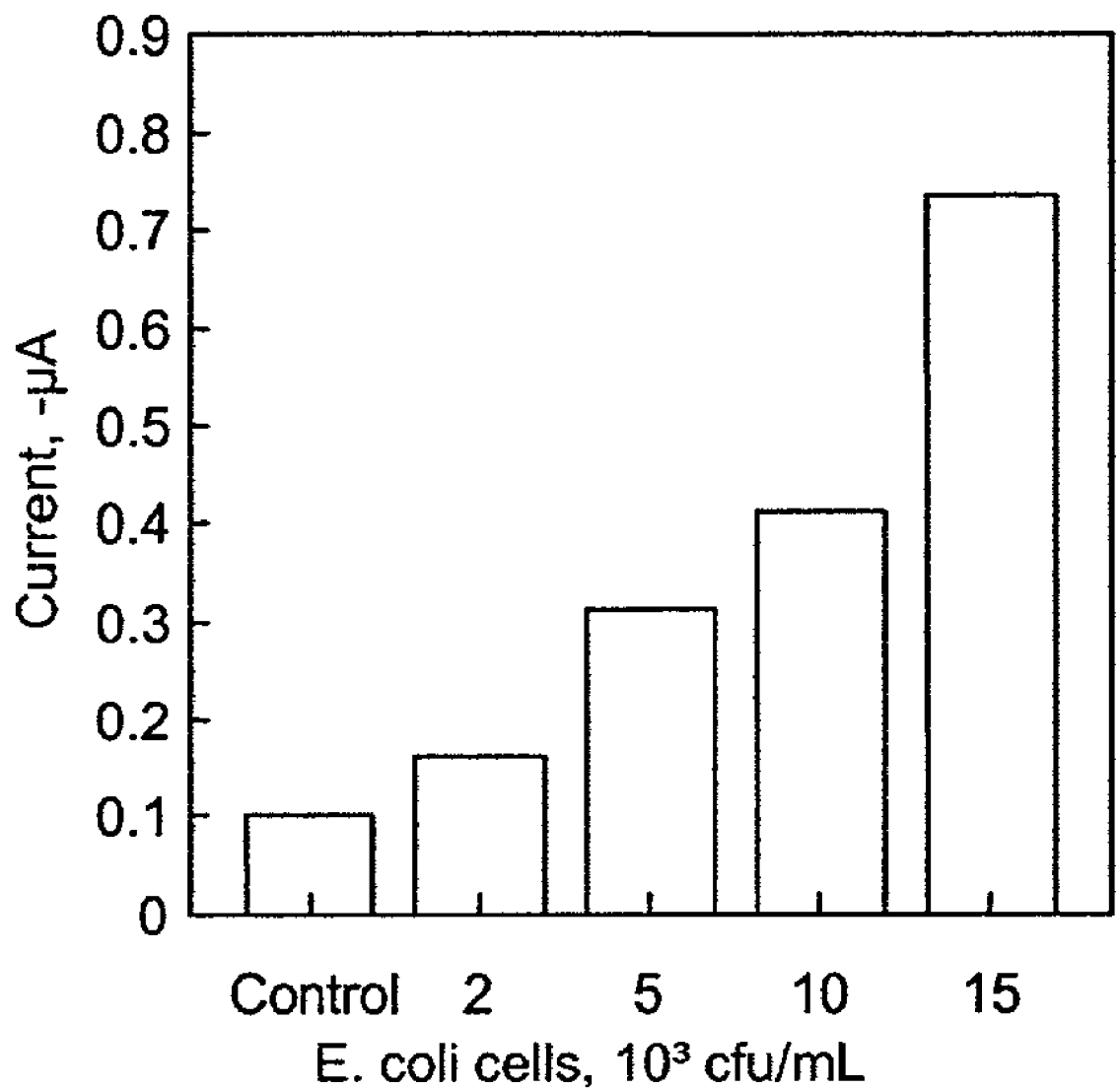

FIG. 5. Shows detection of rRNA from E coli in relation to current produced using capture probes bound to Neutravidin modified surface of a colloidal gold working electrode and electrochemical detection by the disclosed methods. E coli rRNA can be detected directly from blood in the presence of blood products using electrochemical detection. As few as $2.25 \times 10^4$ cells were detected by this method.

Figure 6:
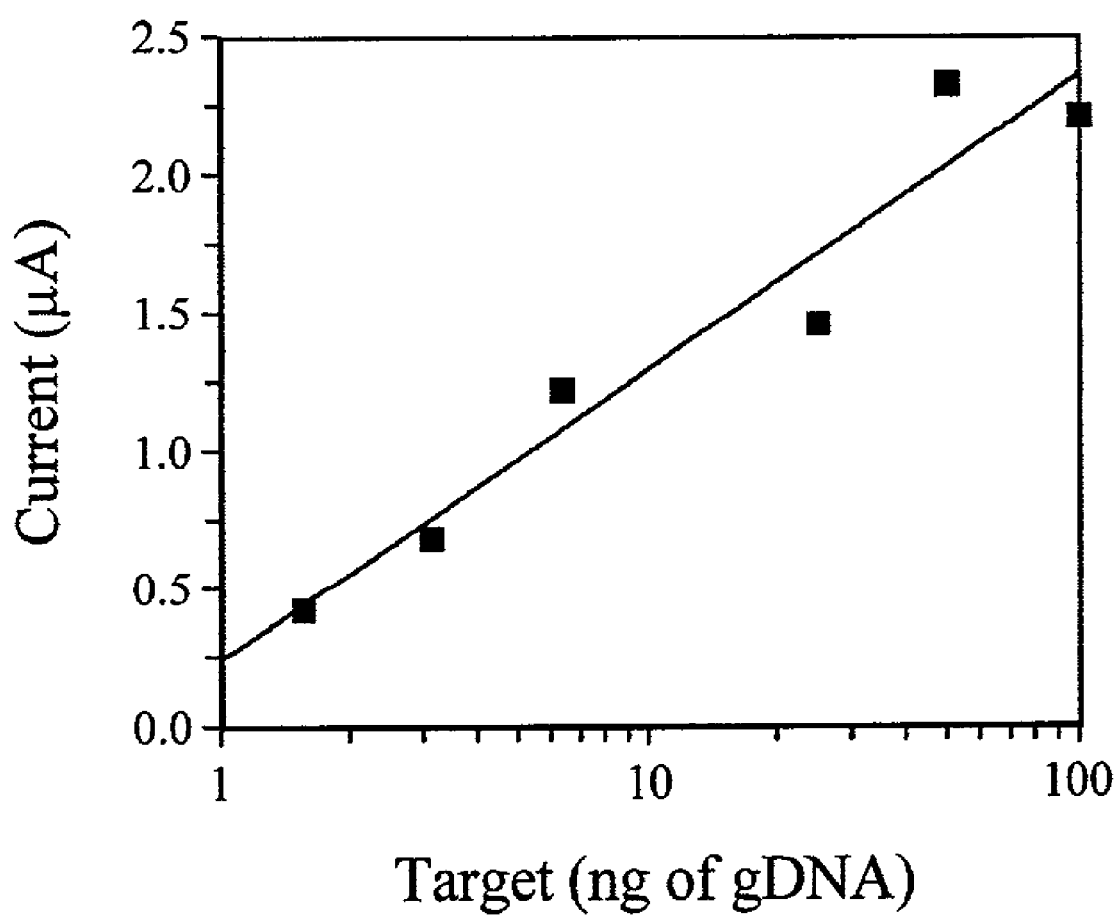

FIG. 6. Detection of PCR amplicon of a single-copy gene BRCA1 in human genomic gDNA, on colloidal-gold/neutravidin sensors.

Figure 7:
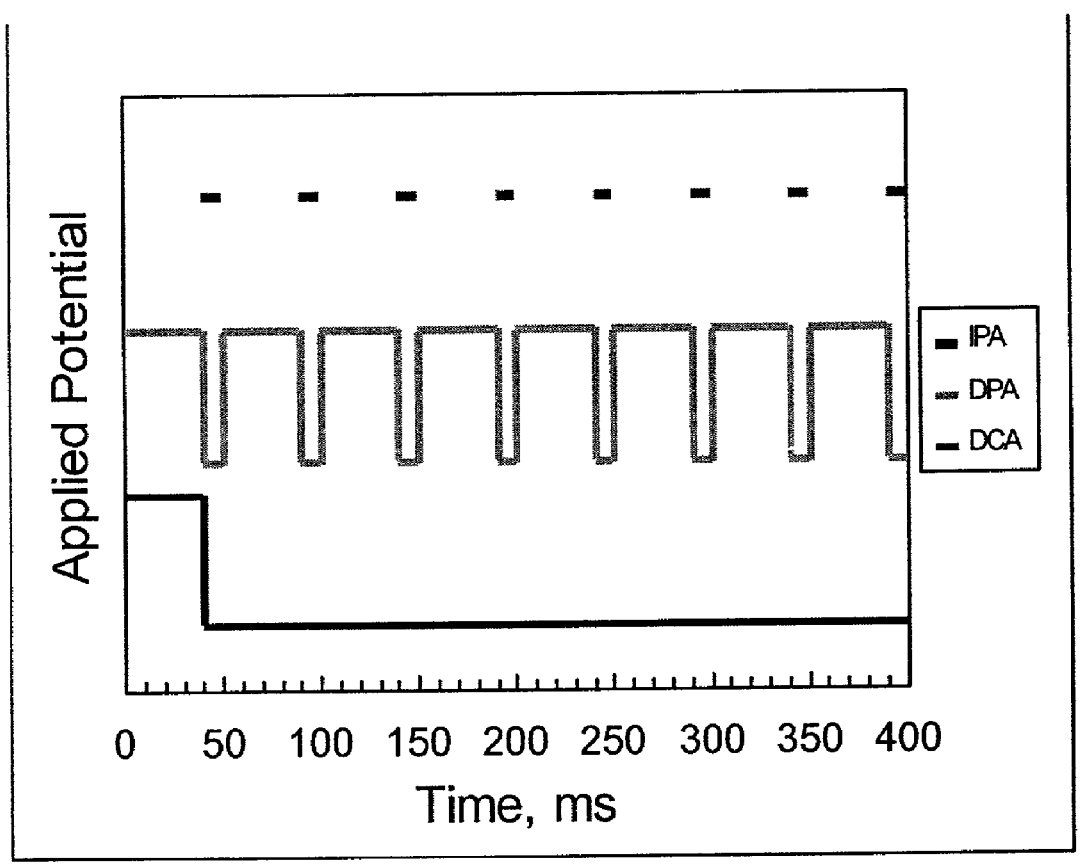

FIG. 7. Shows the potential vs. time comparison profiles for IPA, DPA, and DCA. The potential wave forms shown here are characteristic of Intermittent Pulse Amperometry, Differential Pulse Amperometry and Direct Current Amperometry. The Differential Pulse Amperometry potential waveform is comprised of 45 millisecond base pulses and 5 millisecond detection pulses is used at 20 Hz frequency, with currents measured at the end of each pulse. Current is measured at the end of the detection pulse which is part of a three pulse sequence repeated every 60 milliseconds. The Intermittent Pulse Amperometry waveform consists of 5 millisecond pulses of –100 mV potential, separated by 45 millisecond intervals when a sensor is disconnected from the electronics of a current measuring instrument. This particular waveform was used successfully to increase current signals detected in an E coli assay.

Figure 8:
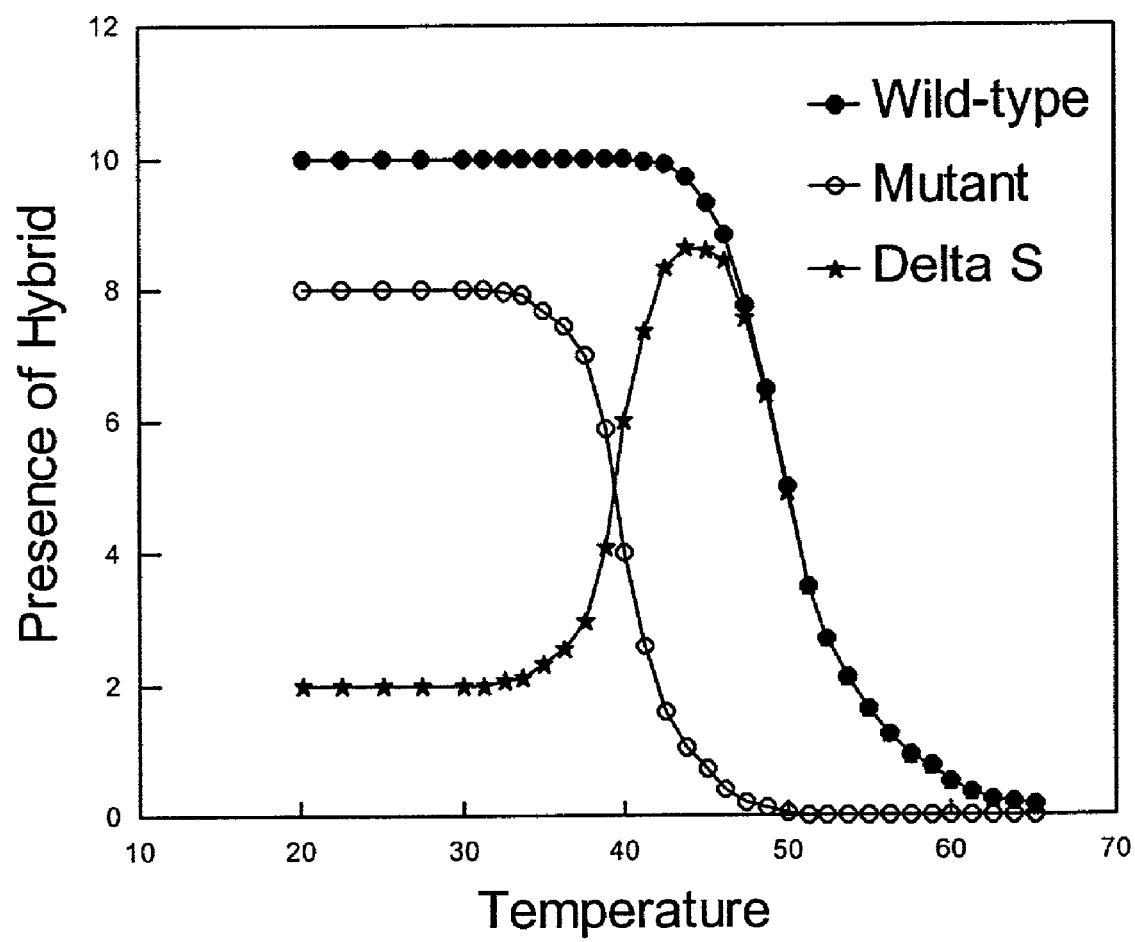

FIG. 8. Hypothetical wild-type and mutant targets give predictable melting curves which when subtracted yield a delta curve with a characteristic peak. The delta plot will vary in amplitude and shape with the peak falling at different temperatures depending on size and type of mutation, size of capture probe and percent G/C of the hybrid.

Figure 9A:
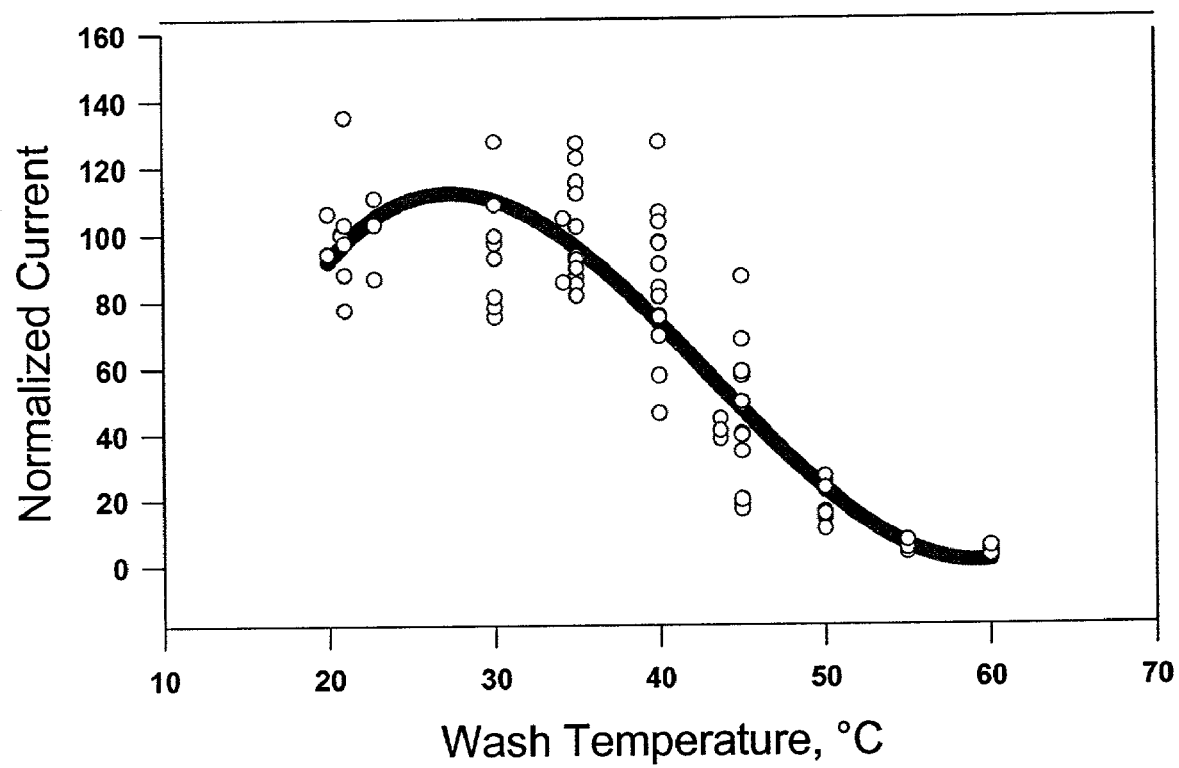
Figure 9B:
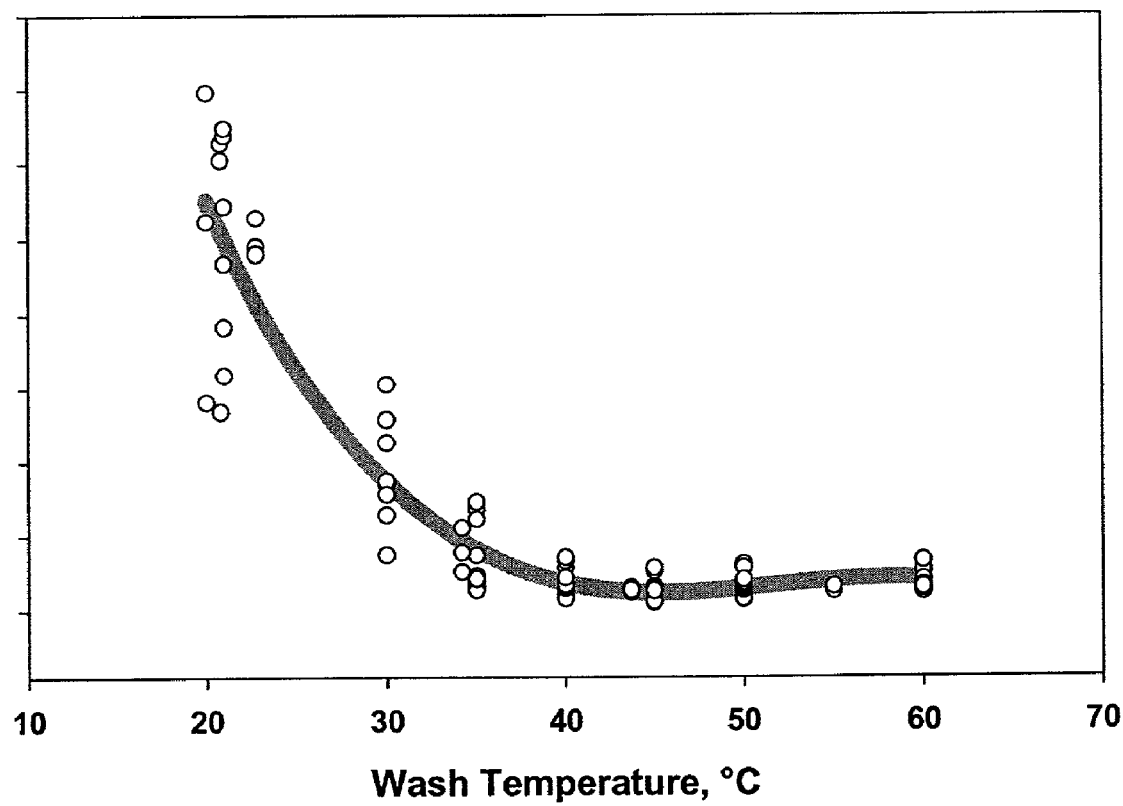
Figure 9C:
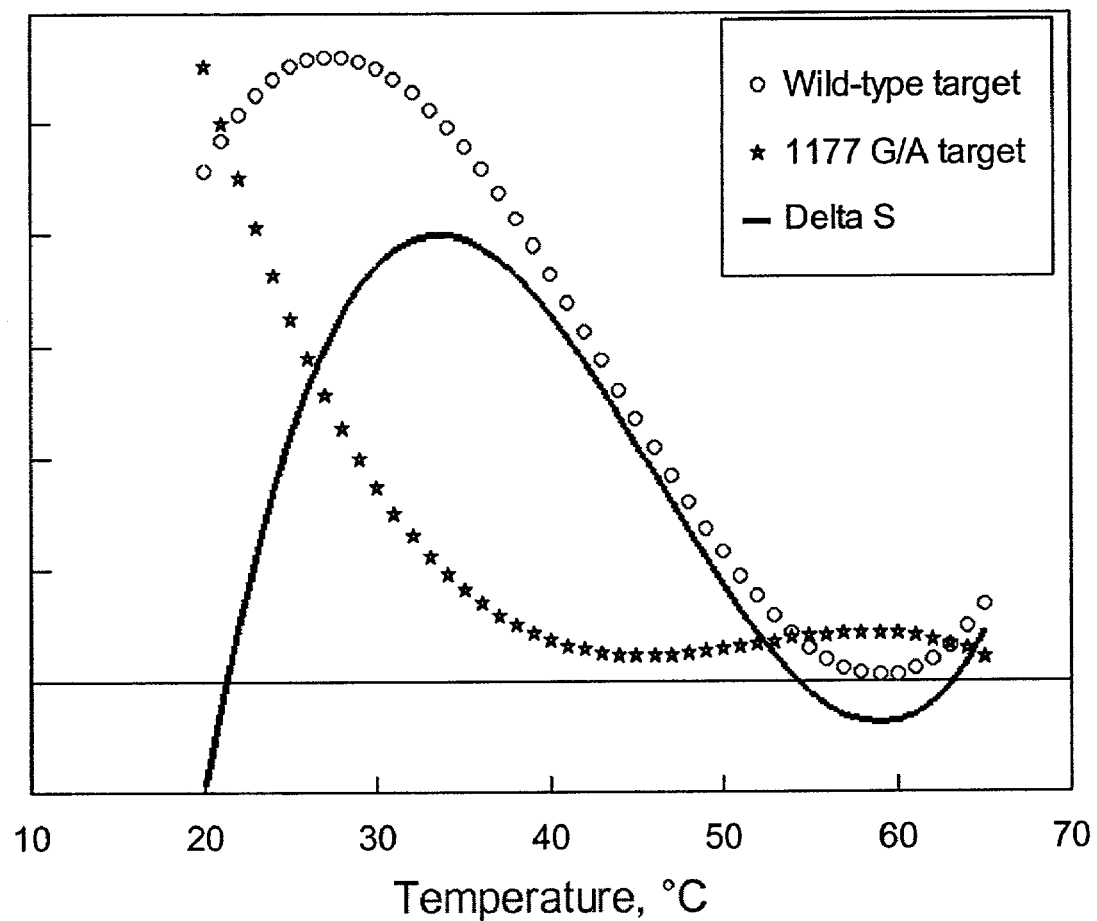

FIG. 9A, FIG. 9B and FIG. 9C. Difference thermal scanning data was analyzed by $3^{rd}$ order polynomial regression to obtain target melting curves (left & middle) and difference curve/peak temperature (right). Wild-type and mutant synthetic targets were combined in solution hybridization reactions with appropriate Capture and Detector probes. Hybrids were captured on replicate sensors and washed at the various temperatures shown on the graphs.

Figure 10:
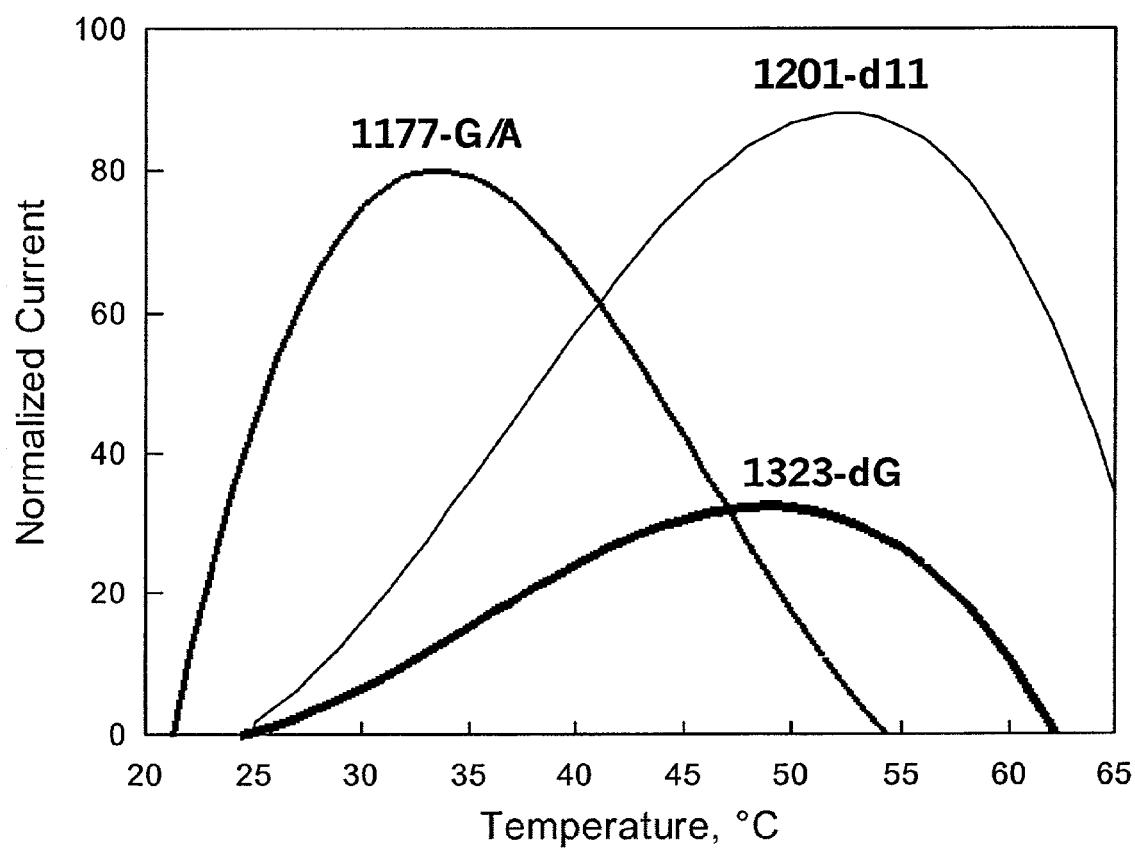

FIG. 10. Compares data collected for the BRCA1 gene mutations: 1177 G/A, 1201-d11 and 1323-dG under similar conditions showing distinct peaks in the delta or difference curves for three different mutations (see FIGS. 11A–C).

Figure 11:
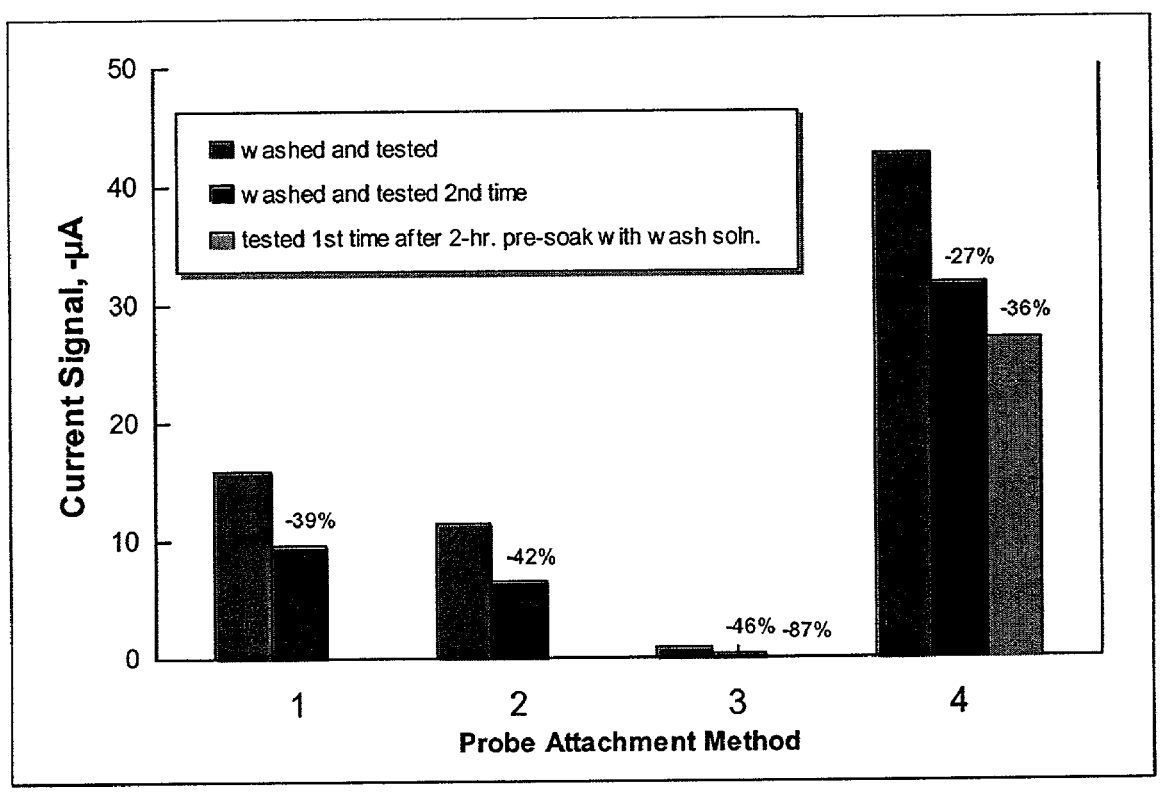

FIG. 11. Shows the effects of different methods of surface attachment of a capture probe on the sensor's responses to DNA. 1: Covalent binding on pre-oxidized carbon electrode; 2: Covalent binding on untreated carbon electrode; 3: Adsorption on untreated carbon electrode; and 4: Avidin-biotin binding on cAu/NA-modified carbon electrode.

Figure 12:
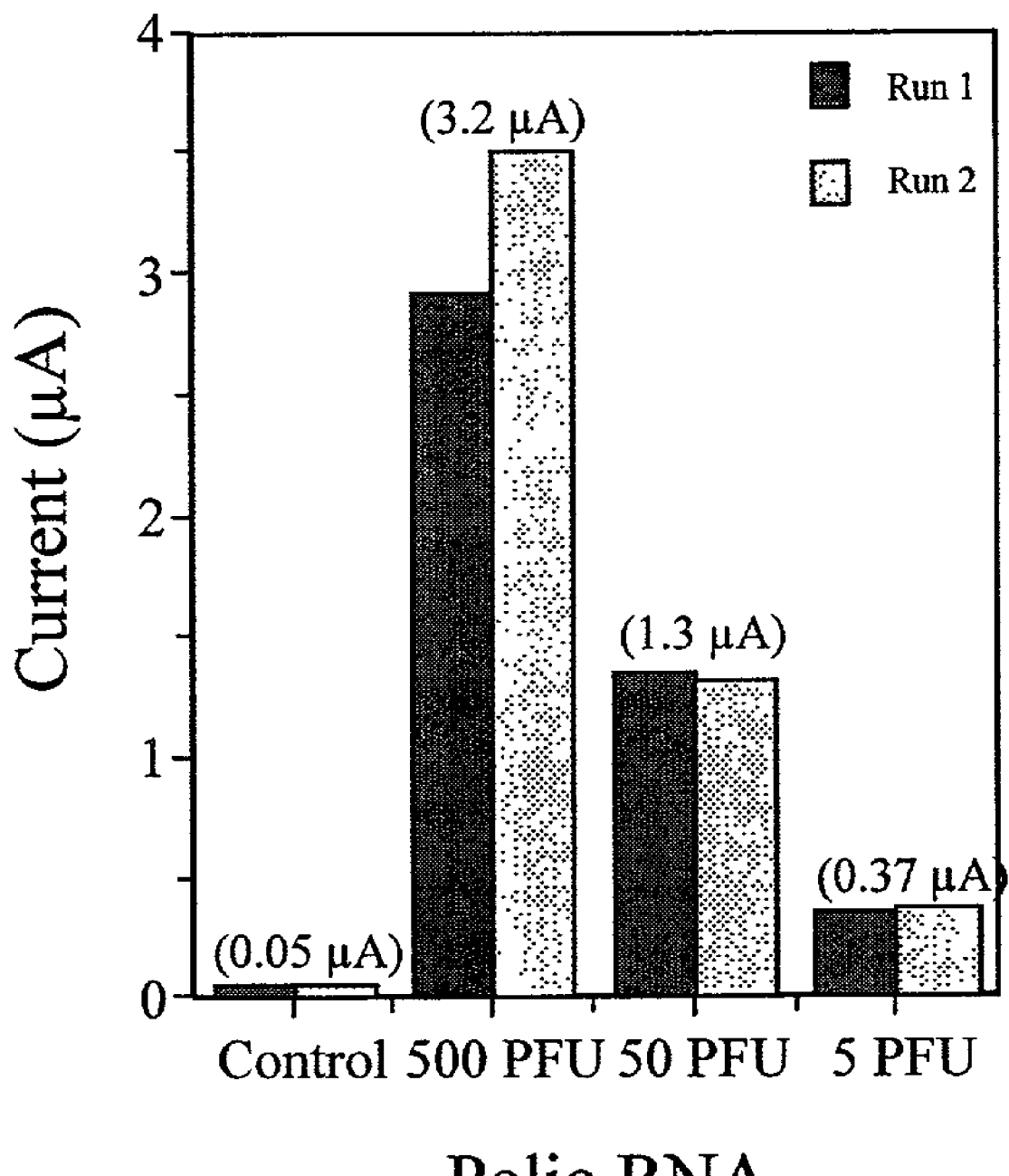

FIG. 12. Detection of polio virus at low levels. Polio virus RNA from polio infected cells corresponding to 5, 50 and 500 pfu of virus was amplified by RT-PCR and measured electrochemically. Large currents proportional to viral RNA content were measured and only small background current was detected with RNA isolated from uninfected cells (control).

Figure 13:
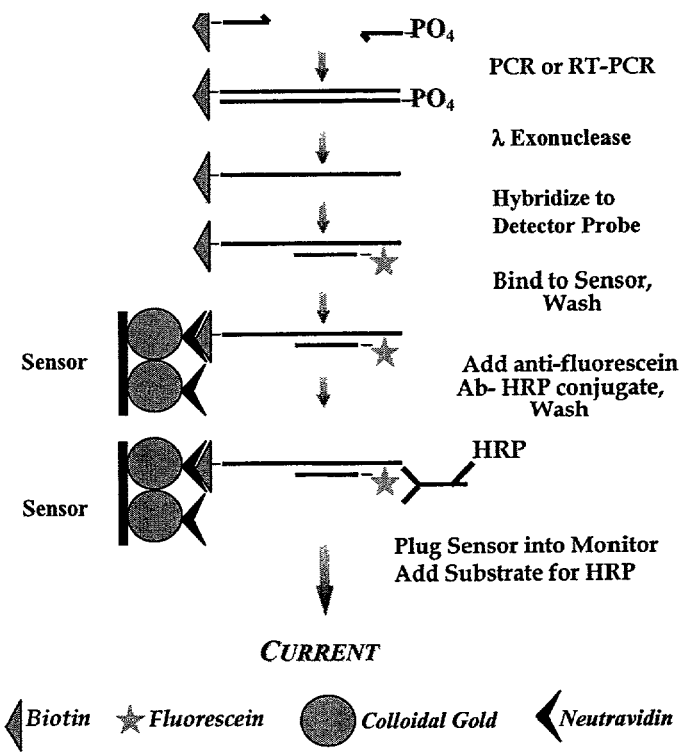

FIG. 13. Schematic diagram showing method of generation of single strand DNA by lambda exonuclease digestion prior to hybridization to detector probe.

Figure 14:
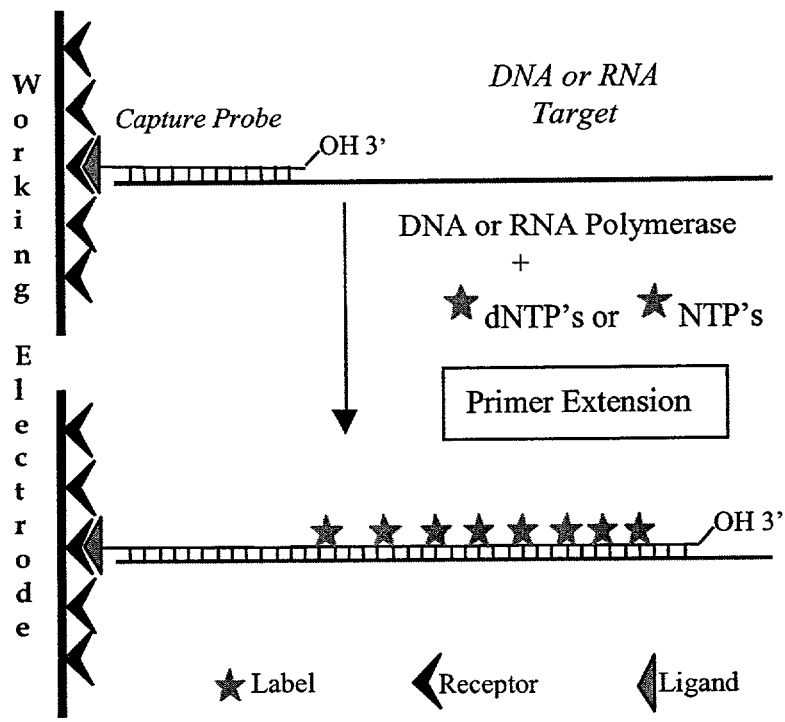

FIG. 14. Schematic diagram showing primer extension signal amplification (PESA). A star represents a labeled nucleotide substrate for the enzyme used in the primer extension. The label used in the example is fluorescein.

Figure 15A:
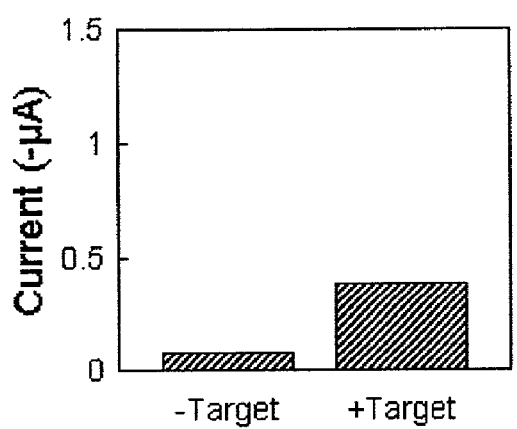

FIG. 15A. Shows detection of nucleic acid target without PESA. −Target refers to the control samples containing no target. +Target refers to test samples containing nucleic acid target. Solutions were assayed by a standard sandwich hybridization method using a capture probe and a detector probe.

Figure 15B:
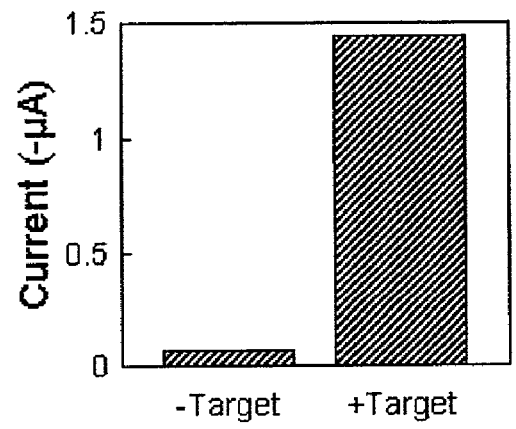

FIG. 15B. Shows detection of nucleic acid target with PESA. −Target refers to the control samples containing no target. +Target refers to test samples containing nucleic acid target. Solutions were subjected to PESA reaction and then assayed.

Figure 16:
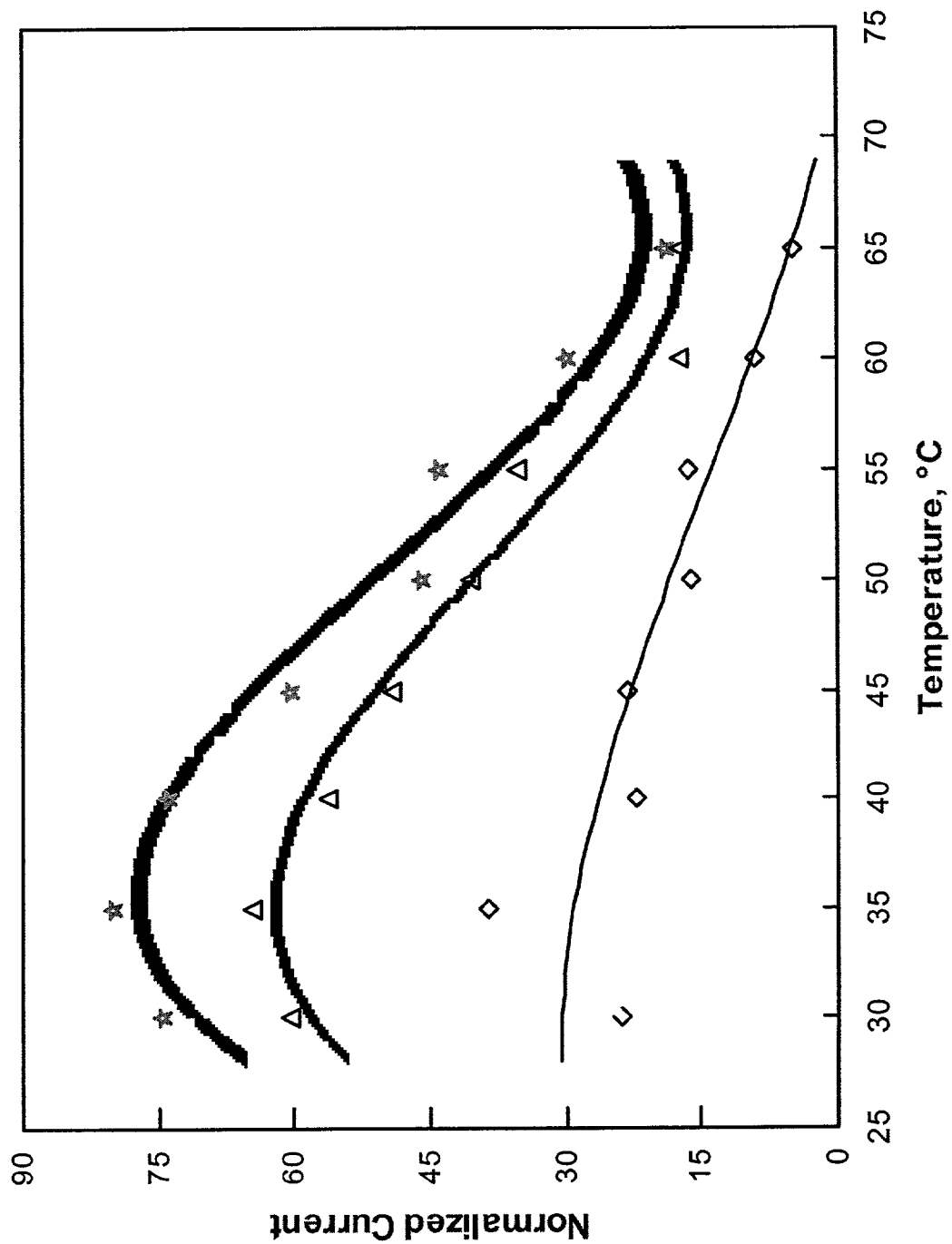

FIG. 16. Difference ($\Delta$) curves showing the presence or absence of a mutation detected by comparing wild-type with target signals at different temperatures. The wild-type target yields a flat difference curve where a heterozygous mutant and a homozygous mutant yield peak differences of increasing, size at similar peak temperatures. The amplitude of the $\Delta$ for the heterozygous mutant is roughly halfway between that for wild-type and homozygous targets.

Figure 17:
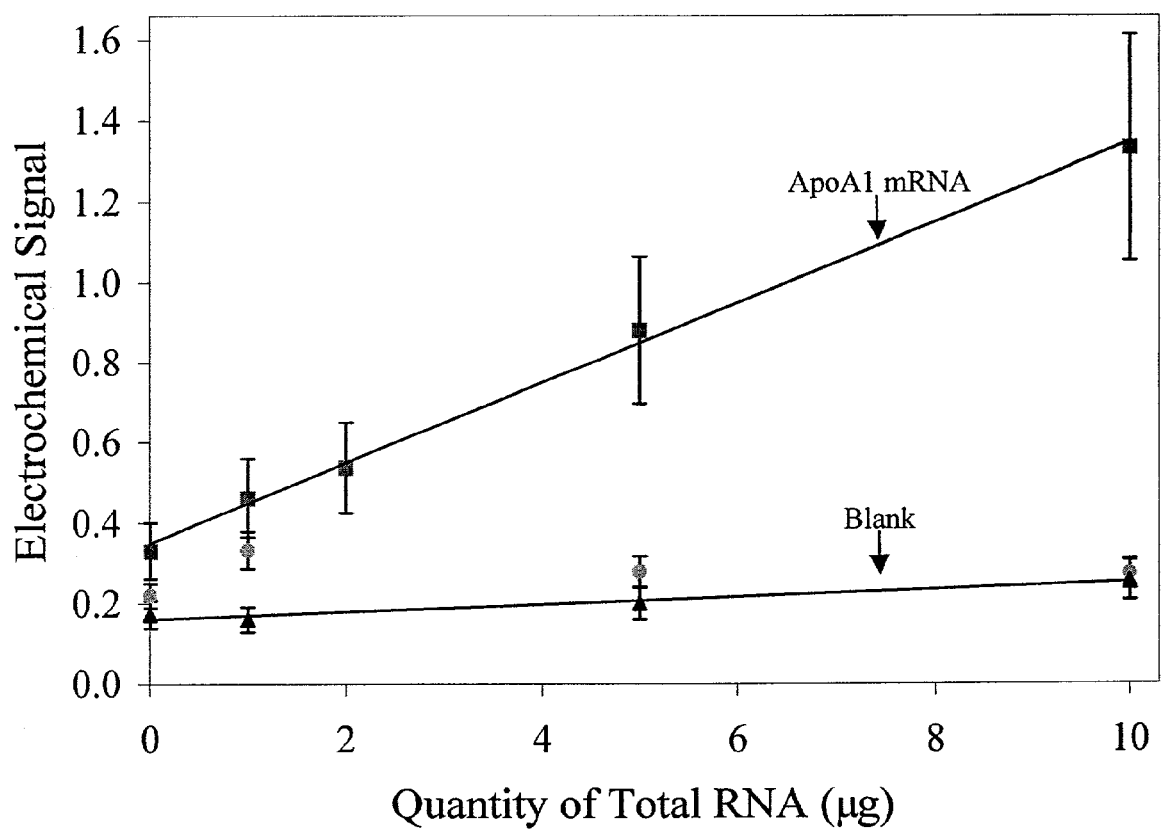

FIG. 17. Shows the electrochemical detection of ApoA1 mRNA expressed in cultured hepatocellular carcinoma cells in relation to current produced using, capture probes bound to Neutravidin modified surface of a working electrode and electrochemical detection by the disclosed methods. Expressed mRNA target can be detected directly in total RNA. As little as 60 fg of mRNA target were detected I µg of total RNA by this method.

Figure 18:
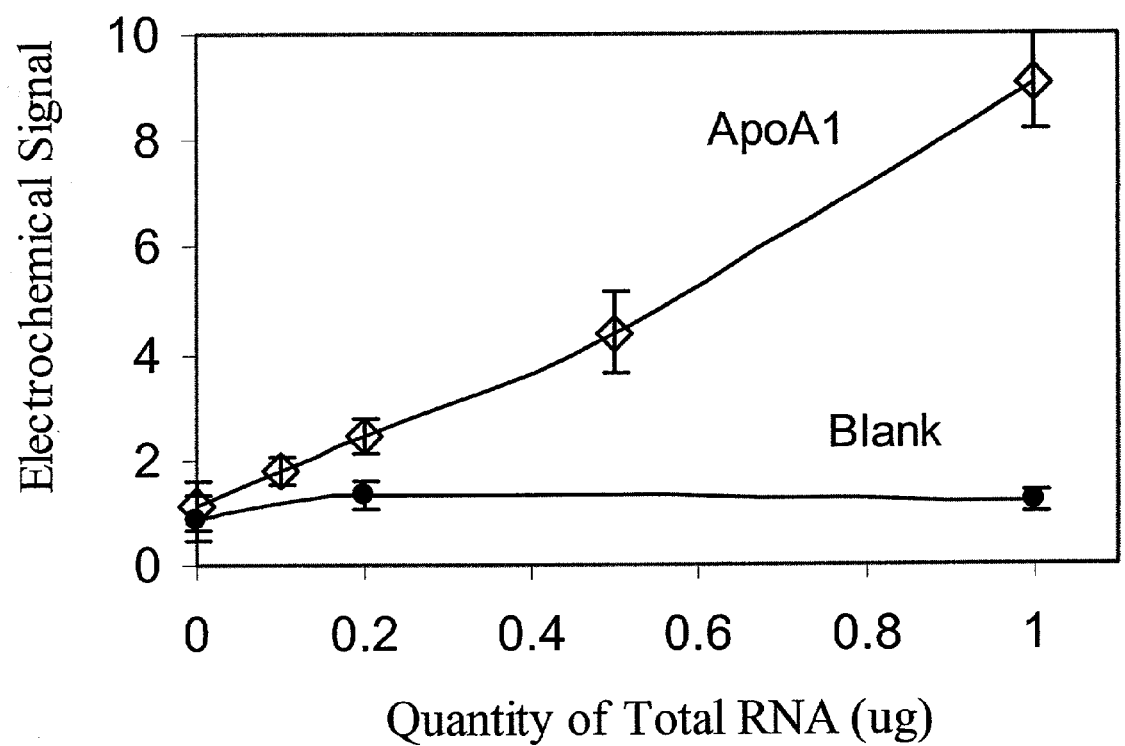

FIG. 18. Shows detection of mRNA with PESA. ApoA1 refers to the test sample containing target and probe. Blank refers to the control samples without target.

4.0 DESCRIPTION OF ILLUSTRATIVE EMBODIMENTS

The present invention provides methods and compositions for the selective, rapid, and sensitive electrochemical detection of any nucleic acid, particularly those with a known sequence or sufficiently identified to allow selection of appropriate hybridization probes. The methods are applicable to the analysis of samples in clinical, research, or outdoor, i.e. field settings, and are also useful for monitoring in genetic epidemiology and environmental remediation.

The quantifiable electrochemical signals of the invention result from electroactive groups bound or in close proximity to a working electrode surface by an immobilized probe-target. A free electroactively labeled probe in solution that is not immobilized on the electrode surface does not couple efficiently enough to the electrode to produce an electrode response (O'Daly et al., 1992). Thus, no separation of free probe from hybridized probe of the invention is needed.

In general, an electrochemical analysis performed using the disclosed methods and biosensor requires no more than about 10 or 15 minutes to perform. The signals generated are typically proportional to the amount (concentration) of target nucleic acid present in the sample.

An especially effective component for use in the invention is an electrochemical monitor available from AndCare, Inc., (Durham, N.C.). This apparatus is sufficiently compact to be hand-held and utilizes samples that are mounted on disposable test strips. Each test strip is inserted through a small opening into a box-like structure. A sample well on the test strip contains a sample of target nucleic acid sequence/ oligonucleotide-probe hybrid. The sample well is located over a colloidal gold electrode which is screen-printed on the test strip together with a reference (preferably silver) electrode and a counter (preferably carbon) electrode. The system automatically performs the necessary assay steps and measures current generated by the sensor. Each element in the array can be individually addressed and can probe for the presence of a specific DNA sequence. The system can be used to probe multiple samples for one or more gene variations. Strong signals from a particular element in the array are indicative of the presence of gene variations in that sample.

Species specific segments or sequences of nucleic acids which are known to characterize or identify the nucleic acids are employed. Thus, the present invention in a broad aspect concerns an electrochemical system for detecting specific nucleic acids, including DNA and RNA, by the use of oligonucleotide probes which are specific for identifying segments of such acids. The invention has application for detecting identified nucleic acids in complex mixtures and is particularly useful for assaying virtually any species, whether microbial or higher life forms, so long as an identifiable gene or other segment can be determined. Diagnostic assays, such as for aberrant chromosomal variations, cancers and genetic abnormalities are also part of the invention to the extent that targeted nucleic acid sequences or segments can be selectively probed employing the disclosed methods.

The invention may be viewed in several different contexts: as a method involving the capture of an electrochemically labeled nucleic acid on an electrode surface; as an electrode for use in the electrochemical identification of nucleic acid sequences; and also as an electrochemical system for identifying a pathogen, genetic defect, or messenger RNA expression for example.

The present invention improves upon current gene-probe assays by requiring fewer steps to perform, detecting specific targets at lower concentrations, and needing less time to complete. A particular advantage of the present invention is that it can be used outside of a well-equipped laboratory setting. Complex instrumentation is not required because the probes and electrodes may be used with an inexpensive, hand-held meter or field-usable monitor. The electrochemical assays can be automated in a number of ways using relatively inexpensive equipment and procedures that are generally more robust and less complex for the operator to perform than comparable immunoassays.

The present invention couples the simplicity and sensitivity of electrochemical techniques with gene-probe or other biological probe hybridization assays to detect specific types of DNA or RNA through direct analysis. The methods comprise hybridizing a "target" nucleic acid sequence with a selected probe that specifically hybridizes to the target nucleic acid sequence or segment. A particular advantage of the disclosed method is that optically transparent samples are not required, nor is the purification or isolation of a target nucleic acid sequence. Target sequences may possess more than one characterizing sequence or segment. Naturally, it is preferable that such characterizing sequences be unique to the target sequence.

More than one target DNA or RNA species may be detected from a sample; that is, more than one target-nucleic acid segment may be hybridized to a distinct probe or set of probes. For example, target-nucleic acid segments from both *E. coli* and *Salmonella* may be hybridized to different probes such that two different hybridized probe-target complexes are formed: one which comprises a nucleic acid segment from *E. coli* and one which comprises a nucleic acid segment from *Salmonella*. Each hybridized target nucleic acid sequence is capable of bonding or otherwise coupling to a working electrode that is specific to that hybridized target nucleic acid segment.

The current detection range for the quantitation of a target nucleic acid segment is between about 0 nA and about 10,000 nA. Qualitative detection of a selected nucleic acid segment can be between about 100 nA and about 20,000 nA.

Accordingly, a method of electrochemically detecting a target nucleic acid segment is provided. A DNA or RNA segment is "captured" at a working or "test" electrode surface by a probe which hybridizes with the segment. The captured target is then electrochemically detected by applying an amperometric potential across a working electrode and a reference electrode to generate a current which then flows between the working electrode and one other electrode. Measurement of such a current indicates the presence of the target nucleic acid segment.

Target nucleic acid sequences of segments may vary widely. Especially attractive are characteristic or unique nucleic acid sequences found in various microbes or mutated DNA that can be used in the diagnosis of diseases, in environmental bioremediation, in the determination of genetic disorders, and in genetic epidemiology. A targeted nucleic acid sequence may be detected in complex mixtures such as whole blood or blood fractions, tissue samples, lysed bacterial samples, culture media, ground meat samples, the surface of a meat sample, biofilms, soil, fish slime, water from fish tanks, marine sediment, and marine or freshwater samples, for example.

In many cases, the invention reduces or eliminates the need for using PCR™ (Polymerase Chain Reaction) based technology, cell culture or other methods of selectively amplifying a target nucleic acid sequence. The invention also has application in readily detecting the degree of amplification and the amount of PCR™ amplified product as the product is produced.

An important aspect of the present invention lies in the electrode biosensor and electroactive label coupling which promotes a strong, quantifiable catalytic current when a "bridge" is made by hybridization of the capture probe with its complementary target nucleic acid segment. At the molecular level, this "bridge" puts the electroactive label in close proximity to the electrode, such that a current is generated when an amperometric potential is applied across the working and reference electrodes.

The electrochemical cell comprises two or more electrodes. One electrode serves as a reference electrode and one is a working electrode. In one embodiment, two electrodes are present, in which case the current flows between the working and reference electrodes. Alternatively, three electrodes are present; a working, a reference and a counter electrode, in which case the current flows between the working and the counter electrodes.

Preferred working electrodes are disposable and in certain embodiments have ultramicro-arrays of colloidal gold particles on the surface. One working electrode is present for each different probe-target complex one desires to detect. A potentiostat or other suitable electrometric device serves to measure current generated between the working electrode either a reference or counter electrode. While working electrodes with arrays of colloidal gold particles have proven to be effective and are preferred in many applications, it is contemplated that bulk metals as well as colloidal or fine particulate metals may also be employed. Colloidal metals include gold, silver and platinum. Particulate metals may include gold, silver, platinum, and copper.

The potential imposed on an electrochemical cell of the invention may be constant, such as provided by a potentiostat and which measures a resulting steady-state current. A preferred potential is a "pulsed" potential, i.e. a series of brief, intermittent potentials of generally constant amplitude that are applied or pulsed through the electrochemical cell. The pulses may also alternate between two voltage levels on each side of a common voltage level. A preferred pulsed potential is intermittent in which the potential is simply disconnected from the electrochemical cell at intervals.

The electrochemical potential pulses confine the electrochemical reaction to specific short intervals thereby minimizing depletion of reporter molecules at the surface of the working electrodes and enabling repetitive measurements and acquisition of large number of data points thus increasing sensitivity at least 10-fold. The printed biosensor array is particularly useful for intermittent electrochemical pulse measurements because as little as 10 seconds is sufficient to stabilize the intermittent pulse signal; high density working electrode arrays with electrode sizes <1 mm require the sensitivity, precision, and reproducibility of intermittent pulse detection for optimal response; and a single potentiostat, with suitable multiplexing capability, can be used for simultaneous measurements of arrays of sensors.

Rapid probe hybridization and electrochemical sequence detection are utilized to achieve rapid and sensitive detection of nucleic acids. Most current tests for DNA sequences are based on fluorescent signals. When the DNA or RNA target is present in low levels the polymerase chain reaction (PCR™ or RT-PCR) may be employed to multiply the nucleic acid sequence so that detectable quantities of the target nucleic acid are produced. The present invention utilizes electrochemical sensor signals instead of fluorescence and can be used with a small hand-held apparatus to detect multiple biological agents rapidly and, in some embodiments, without amplification of target nucleic acid sequences.

Distinct advantages of electrochemical detection combined with biological-probe methodology are readily apparent. A detectable signal can be generated in minutes as opposed to hours, as with many calorimetric assays, or even days, as with many radioassays. Harmful and increasingly difficult to dispose of materials, such as radioisotopes or mutagenic colorimetric labels, are not required. Quantification of the signal is easily accomplished, and in one example, a pathogen was detected with as little as picogram to femptogram ($10^{-12}$ to $10^{-15}$ gram) levels of target DNA.

Probes are effectively coupled to the surface of electrodes so that a target-DNA or RNA is detected with high sensitivity. Several examples have demonstrated the increased sensitivity achieved by the electrochemical probe methods compared to conventional methods of detecting coliform bacteria in samples collected from marine/freshwater environments or food extracts. The electrochemical detection system provides an improved means of monitoring human and environmental health through food and water-safety assays as well as a highly selective method of detecting gene mutations associated with genetic or acquired diseases.

The invention further encompasses a monitoring system that operates using intermittent pulse amperometry (IPA) which is a sensitive electrochemical technique for simultaneous and independent measurements of DNA in multitarget samples using low or high-density sensor arrays. IPA measurements involve a series of millisecond pulses of constant potential separated by short periods when the electrode is held at open circuit potential. IPA currents are significantly larger than those measured by conventional DC amperometry (DCA). In comparison with differential pulse amerometry (IPA), IPA is more precise and more accurately measures currents from very low concentrations of one form of a redox couple (mediator) in the presence of a large excess of the other form. In comparison with the sensitivity of DCA, IPA provides approximately ten-fold signal amplification for picomolar concentrations ($10^{-12}$ mol/L) of nucleic acid targets and measurement in 10 seconds or less. IPA is particularly suitable for multi-channel measurements.

The disclosed electrochemical detection system typically utilizes a first probe, the "capture probe", and may also comprise a second probe, the "detector probe." Optionally, three, four, five or more probes are used. Where two or more probes are used, there should be no sequence overlap between the two or more selected target nucleic acid segments. The target nucleic acid segments may be adjacent to each other or widely separated from each other.

In a 2-probe assay method, each probe typically comprises an oligonucleotide segment coupled or covalently bound with another molecule such that one of the probes (termed the capture probe) bonds or otherwise couples to a working electrode of an electrochemical cell; the other probe (termed the detector probe) is typically labeled with an electroactive label or reporter. When both capture probe and detector probe are hybridized to their respective target nucleic acid segments and the hybrid is bonded or otherwise coupled to a working electrode and an electroactive label, the complex formed can be coupled to an electrochemical cell to produce a catalytic current when an amperometric potential is applied.

In certain cases, a nucleic acid, sequence or segment may inherently possess an electroactive reporter so that a detector probe may not be required. A nucleic acid probe normally does not bond to an electrode surface but may be attached with an agent which binds it to the electrode. A bonding agent bonds the capture probe to the working electrode which is preferably a colloidal gold electrode. Bonding agents include proteins, oligonucleotides or other molecules that bond to the working electrode and the capture probe. One method of bonding or coupling is to incorporate a protein such as avidin or streptavidin or an oligonucleotide on the electrode surface. By also incorporating a molecule such as biotin into the capture probe, the oligonucleotide attached to the electrode hybridizes with both the bonding agent and the capture probe.

In a one probe assay method, a probe that comprises an oligonucleotide segment is hybridized to a target nucleic acid segment and coupled to a working electrode such that when an amperometric potential is applied across the working electrode, a current is generated which flows between the working electrode and another electrode. The latter electrode may be a reference electrode or preferably a third electrode, designated as a counter electrode.

Each probe comprises at least an oligonucleotide sequence, which is complementary to a contiguous nucleic acid sequence of an identified, target pathogen such that the oligonucleotide sequence specifically hybridizes to the nucleic acid sequence of the pathogen under conditions of high stringency. Oligonucleotide sequences of 15 to 50 nucleotides are preferred; however, shorter or longer sequences may in certain instances be employed such as 15, 16 or 17 nucleotides in length.

In certain embodiments where at least two probes are used, either the capture probe or the detector probe may hybridize to any one of a generic group of related targets of interest. In such cases, it is generally preferred that the other probe be specific to a particular target species. Alternatively, one may choose to use both a capture probe and a detector probe that hybridize to any one of a group of related targets if the objective is to measure the occurrence of a particular generic group. For example, a detector probe can hybridize to 16S rRNA of both *E. coli* and *Salmonella*, and a first capture probe can also hybridize to 16S rRNA of both *E. coli* and *Salmonella*. An electrochemical signal generated by using these two probes would indicate that either or both *E. coli* and *Salmonella* are present in the sample. Alternatively, a second capture probe which hybridizes only to nucleic acid segments of *E. coli* maybe used in place of the first capture probe. An electrochemical signal generated by using the detector probe and the second capture probe indicates only the presence of *E. coli* in the sample. *Salmonella* nucleic acid segments that are hybridized to the detector probe would not be detected, since the *Salmonella* nucleic acid segments are not coupled to the electrode.

The oligonucleotide sequence of a probe may be bound, bonded, conjugated or otherwise coupled with either a protein, a small molecule such as biotin, or an antibody; or with another molecule, such as fluorescein (Fl) or dioxigenin (DIG), that is able to bond with an electroactive reporter group; or is bonded directly to a biosensor electrode; or is able to hybridize to another molecule, such as an oligonucleotide or protein, such as an avidin, which is bound to a biosensor electrode.

In certain cases, the capture probe may include an additional component, such as biotin or an antibody, that is reactive with a component of a colloidal gold electrode, such as avidin, streptavidin, protein G or protein A, so that the capture probe becomes bound to that component or is itself bonded, bound, conjugated or otherwise coupled directly to the colloidal gold electrode.

The detector probe includes at least one molecule, such as fluorescein (F1) or digoxigenin (DIG), that can be coupled, conjugated, bound or otherwise bonded to an electroactive label, such as horseradish peroxidase (HRP), or the probe is directly coupled, conjugated, bound or otherwise bonded to an electroactive reporter group.

In a preferred embodiment, the molecule conjugated to the oligonucleotide of the capture probe is biotin, at least one molecule of Fl or DIG is conjugated to the detector probe, and the electroactive reporter group is HRP. Alternatively, either probe or both may recognize an antibody such as HRP-anti-fluorescein antibody.

Target nucleic acids may be labeled or tagged with an electroactive label that bonds sufficiently to an electrode surface to obviate the need for a special capture probe. In most instances, it will be desirable to hybridize or otherwise couple probes to more than one sequence in a target nucleic acid as this may provide improved signal strength and accuracy in identifying the target nucleic acid.

An electroactive label may be added to the target nucleic acid sequence or to any detector probe, or it can be inherent in the target. A variety of labels may be used to label the nucleic acid probe to allow efficient detection. Biotin-labeled deoxyribonucleoside triphosphates incorporated into the DNA probe by enzymatic polymerization has been described (Langer et al., 1981). After hybridization biotin-labeled probes are detected using neutravidin modified sensor electrodes. While there are numerous nucleoside triphosphate modifications only a few effectively incorporate into DNA. The pyrimidine nucleotides dUTP and dCTP modified at the C5 positions can be incorporated with both DNA polymerase and terminal transferase. In addition, dATP modified at the N6 position may be incorporated with either enzyme (Gebeychu et al., 1997). The probe is attractive because it is modified at the C5 position where it does not interfere with hybridization and also has a linker arm long enough to allow access to neutravidin. Neutravidin is superior to streptavidin for DNA detection because it has less non-specific binding. The labeling method and detection method contributes to probes with a lower detection limit near 0.1 picograms or less. Incorporation of a biotinylated nucleotide is the standard for non-radioactive DNA detection. Using the disclosed methods, biotin-labeled probes can be detected in a 10 minute neutravidin binding step. Detection with antibodies that provide equivalent sensitivity requires the use of two antibodies and at least two hours incubation time (Keller and Manak, 1993).

An electron transfer mediator and a substrate may be added to the electrochemical cell. An exemplary electron transfer mediator is ferrocene monocarboxylic acid (Fc). An exemplary substrate is a peroxide such as hydrogen peroxide. The substrate and electron transfer mediator are added to the aqueous medium after hybridization of the capture and/or detector robes with target nucleic acid sequences and, if necessary as separate steps, allowing the hybridization product to couple with an electroactive label and the working electrode.

A variety of electroactive labels may be used. A preferred electroactive reporter group is horseradish peroxidase (HRP). Other electroactive reporter groups that can be used include, but are not limited to, microperoxidase, soybean peroxidase, alkaline phosphatase, and thiol groups inherent in the target nucleic acid segment. Soybean peroxidase is stable up to 90 C. and has an activity similar to HRP. Electrochemical measurement of the activity of the soybean peroxidase label is expected to give results similar to a horseradish peroxidase.

Microperoxidases may also be employed. This group consists of themostable peroxidases. The structure is based on the heme portions of cytochrome C. In addition to their resistance to higher temperatures, the microperoxidase enzymes are small, having molecular weights of 1500–1900 compared with the larger horseradish peroxidase which has a molecular weight of 44,000 and alkaline phosphatase which has a molecular weight of 80,000. The mobility measured as the diffusion coefficients of probes conjugated to the microperoxidases is significantly higher than the mobility of horseradish peroxidase and alkaline phosphatase conjugated probes. This results in higher efficiency of hybridization that may compensate for the lower activity of these enzymes.

Alkaline phosphatase is stable up to 75 C. It is expected to also be useful as a label for hybridization assays. A particularly preferred substrate for the enzyme is 4-aminophenyl phosphate which has the appropriate potential required for oxidation on the sensor and current sensitivity.

Detector probes of the present invention may be coupled directly or indirectly with electroactive reporters or reporter groups such as horseradish peroxidase (HRP) so that a strong catalytic current is produced from hybridized HRP-labeled probes, for example, captured on the working electrode surface. Indirect coupling of a detector probe to an electroactive reporter group is achieved through the attachment of another molecule to the oligonucleotide sequence of the detector probe. This molecule may be, but is not limited to, biotin, fluorescein, digoxigenin, a thiol group or other oligonucleotide sequence.

4.1 Peptide Nucleic Acids

PNAs may be used in the disclosed biosensor as detection and/or capture probes. When used as a detection and/or capture probe, the PNAs may be utilized to detect polynucleotides such as PNAs, RNAs, DNAs, or oligonucleotides, ribozymes, or modified polynucleotides.

Alternatively, PNAs may be the target molecules to be detected using one or more of the disclosed biosensors. When PNAs are the target molecules, the detection and/or capture probes may comprise DNA, RNA, or PNA probes.

The synthesis, properties, and use of PNAs as DNA or RNA "homologs" is well-known to those of skill in the art. PNAs recognize complementary DNA and RNA by Watson-Crick base pairing (Egholm et al., 1993), but PNA probes often hybridize faster and more specifically in certain hybridization and affinity-capture techniques. PNAs also afford several additional advantages, in that they are not degraded by enzymes that decrease the useful lifetime of DNA probes, and they work as well with double-stranded as with single-stranded DNA. Such properties simplify requirements for sample preparation and handling, as well as preserve the effective usefulness and lifetime of PNA-derived target or capture probes.

4.1.1 Peptide Nucleic Acid Compositions

In certain embodiments, the inventors contemplate the use of peptide nucleic acids (PNAs) in the practice of the methods of the invention. PNAs are DNA analogs that mimic the structure of the polynucleotide, in which the nucleobases are attached to a pseudopeptide backbone (Good and Nielsen, 1997). PNAs can be utilized in a number of methods that traditionally have used RNAs or DNAs (U.S. Pat. Nos. 5,786,461; 5,773,571, 5,766,855; 5,736,336; 5,719,262; and 5,539,082, each specifically incorporated herein by reference in its entirety). Often PNA sequences perform better in techniques than the corresponding RNA or DNA sequences and have utilities that are not inherent to RNA or DNA. Methods of making, and using PNAs are also found in Corey (1997).

PNAs when delivered within cells have the potential to be general sequence-specific regulators of gene expression. Reviews of PNAs and their use as antisense and anti-gene agents exist (Nielsen et al., 1993b; Hanvey et al., 1992; and Good and Nielsen, 1997). Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding Vickers et al., 1995), genome cleavage (Veselkov et al., 1996), biosensors (Wang et al., 1996), in situ hybridization (Thisted et al., 1996), and in an alternative to Southern blotting (Perry-O'Keefe, 1996).

FIG. 1 depicts an illustrative attachment of a PNA probe onto the biosensor through specific interaction with a target molecule. By employing a unique electrochamical measurement method, the detectors deliver accurate, quantitative test results on complex and optically opaque samples in a fraction of the time required to conduct ordinary assays.

4.2 Electrode Circuits

The electrode circuits of the disclosed biosensors may be fabricated by screen-printing carbon and silver inks onto disposable plastic strips, or alternatively by using printed circuit boards. FIG. 2 shows screen-printed single- and dual-sensor strips. DNA or PNA probes are immobilized on the surface of the colloidal gold that coats the working electrodes at the center of each strip or directly on the working electrodes.

Fabrication of the sensor utilizes inexpensive screen printing rather than the more-expensive lithographic technologies. Higher-throughput parallel processing of samples is much simpler than using current chip technology. Furthermore, the technology can be used to process many samples simultaneously for population or drug-discovery studies.

This electrochemical technology relies on hybridization at a PNA or DNA probe-modified electrode, indicated schematically in FIG. 3. The sample is applied to the modified electrode, and hybridization is allowed to proceed. The redox-active enzyme, linked to the detector probe, oxidizes an electrochemical mediator. The oxidized mediator diffuses to the electrode, where it is electrochemically reduced when appropriate potential is applied, and then returns to be re-oxidized at the enzyme. The catalytic current generated at the electrode and measured by the small analytical instrument corresponds to the amount of enzyme label coupled to the sensor through the target probe hybrid, which in turn represents the concentration of the target in the sample.

4.2.1 Electrode Design

The preferred element in the biosensor comprises a carbon electrode coated with an array of probes that is capable of detecting target analyte at attomole ($10^{-18}$ mole) levels in approximately ten minutes. The assay is based on amperometry at a test electrode and has been previously described in U.S. Pat. Nos. 5,217,594; 5,368,707; 5,225,064; 5,334,296; and 5,391,272, incorporated herein by reference.

The use of high performance screen printed sensors containing an ultramicro array of colloidal gold particles is preferred in some applications of the present invention. Due to spherical diffusion, ultramicroelectrode arrays are more electrochemically "active" than corresponding bulk electrodes. The gold particles serve uniquely as a high surface area immobilization support to which enzymes, antibodies or other biomolecules can be attached. The ultramicroelectrode array allows enhanced sensitivity over other electrochemical approaches by having a high effective signal-to-noise ratio, being highly sensitive to analyte and having fast response to the analyte. A small size is also desirable under many assay conditions. The resulting system is applicable for both research and field lab applications that require monitoring large numbers of samples.

The electrical contacts are made inside the monitor with screen-printed electrodes on a plastic test strip (FIGS. 2A and 2B). The area within the circle on the test strip is the sample well, here the unknown, hybridized sample, is to be placed over the working electrode. The working electrode is formed by modifying the surface into the immobilization support for active reactants such as the probes. The central black area is the working electrode onto which active reactants are immobilized. The working electrode is surrounded by two other blackened areas that function as reference and counter electrodes. The three electrodes are contained within a bean-shaped depression which serves as a sample well. Rectangles at the left end of the strip show where electrical contacts are made with the monitor.

Screen printing is a preferred method to fabricate the biosensor electrodes. The electrodes have been printed using a polyester screen of 240 mesh count and 36.25 angle. Appropriate conducting inks may be purchased from DuPont. Multiple overprintings of dielectric have been used to build up the well to contain the sample. A silver electrode serves as the reference electrode.

The electrochemical monitor in its most basic form has a port to accept the disposable test strip, a button to begin the analysis, and a liquid crystal display (LCD) screen to display results. The monitor can display test results on its LCD screen or store data in internal memory. Preferably, configured with an RS-232 port, the stored data can be later uploaded to a personal computer or network for further analysis or long-term storage.

4.3 Probe Design and Target DNA

Short stretches (about 15–50 nucleotides) of single stranded DNA are preferred as oligonucleotide components of the probes of the invention. Two oligonucleotides directed toward separate, non-overlapping segments or regions of a target nucleic acid sequence are used in a sandwich hybridization format. By using two non-overlapping, non-complementary probes to identify a target nucleic acid sequence, the risk of "background noise" being interpreted as a false positive reading is reduced as compared to a system that relies on the hybridization of a single probe for detection.

In certain cases, one of the probes, the capture probe, is biotinylated and is readily bound to the colloidal gold-streptavidin conjugate of the working electrode array. The other oligonucleotide probe, the detector probe, is labeled with fluorescein. A preferred detector probe comprises at least one molecule of fluorescein, a more preferred detector probe includes about two to about four molecules of fluorescein and a particularly preferred detector probe includes about two to about eight molecules of fluorescein. Anti-fluorescein antibody conjugated to an electroactive label, e.g. horseradish peroxidase (HRP), is used to enzyme-label the probe in certain instances.

A preferred source of target is ribosomal RNA (rRNA) rather than genomic DNA because of its far greater copy number in a given cell. For example, there are approximately 1000 molecules of rRNA per *E coli* cell and approximately 500 rRNA molecules per eukaryotic cell. Alternatively, the source of target nucleic acid segments may be genomic DNA, RNA, cDNA, rRNA, or mRNA.

Double-stranded DNA should in most applications be denatured before hybridization. Denaturation can be performed in solution in a test tube. DNA may also be treated with restriction enzymes before denaturation and hybridization with the probes. The stability of the hybrids and consequently the specificity of hybrid formation may be adjusted by varying the temperature and ionic strength of the solution. Other conditions that may be desirable to optimize include, but are not limited to, temperature, magnesium concentration, amount of target DNA and probes, and interference between hybridization and sensitivity.

4.3.1 Detection Methods

Detection methods may be applied in several general formats. These include a direct detection method, the rapid PCR™ detect method and a hybrid PCR™ detect method. In the direct detection method, DNA or RNA may be detected without amplification. This requires two probes specific for a selected target sequence. Typically these probes are a biotinylated capture probe and a fluoresceinated detector probe. The target hybridizes with both probes, is captured on the sensor, is labeled with enzyme-label using anti-fluorescein HRP conjugate and then electrochemically measured following addition of horseradish peroxide substrate and mediator.

The rapid PCR™ detect method can be used to detect and quantify double-stranded PCR™ product directly without a probe hybridization step. This method relies on the specificity of a PCR™ amplification procedure giving a rapid quantitative result. One PCR™ primer is modified at the 5'-end with, for example, fluorescein and a second primer is labeled at the 5'-end with, for example, biotin. The resulting PCR™ product is therefore labeled with a biotin on one end and a fluorescein on the other and can be directly captured on the sensor, reacted with a anti-fluorescein HRP conjugate, and measured electrochemically as described for the direct detection method.

The hybrid PCR™ detect method was designed for situations requiring added specificity. One strand of a PCR™ product is converted to single-strands using lambda exonuclease. This process requires a 5'_$PO_4$ on one of the PCR™ primers. Since lambda exonuclease requires the 5'-phosphate for activity, the non-phosphorylated strand is left intact. The remaining single-strand is then hybridized to the fluoresceinated detector probe and, if appropriate, a biotin-labeled capture probe. The hybrid is captured on the sensor, reacted with an anti fluorescein HRP conjugate and measured.

In each of the three methods described, any target nucleic acid that does not participate in probe hybridization is removed by wash steps after capture of the probe-target-hybrid at the electrode surface. The capture-probe-target-hybrid is detected as a current generated at the sensor when the detection probe, enzyme conjugate, and substrate for the enzyme label are added.

In the direct detection method the lower limit of sensitivity has been shown to be at least 0.5 attomoles (approximately $10^5$ molecules).

The present invention also provides an electrochemical detection system which uses only a capture probe. An electrochemical signal is generated when the target-probe hybrid is immobilized on the working electrode. A controlled potential is applied to the working electrode using the reference electrode. An electrochemical current flows between the working electrode and another electrode in the presence of an electroactive group that is either inherent in the target nucleic acid segment, e.g. a thiol group, or is chemically or enzymatically added to the target.

4.4 Single Nucleotide Polymorphisms

Genetic factors appear to contribute to virtually every disease, conferring susceptibility or resistance to disease, affecting, the severity or progression, and interacting with environmental factors (NIH Guide, 1998). There are several types of DNA sequence variations that affect human health, including insertions and deletions, differences in copy number of related sequences, and single base-pair differences—with these differences being the most frequent. These DNA variations are termed single nucleotide polymorphisms (SNPs) when the variant sequence has a frequency of at least 1% in the population.

Unfortunately, current methods available are often inadequate for scoring known SNPs in genotyping assays because of low throughput, efficiency, and cost. The present work discloses a new, effective method of scoring known SNPs in which a new sensor array chip has been designed to analyze DNA. An advanced analyzer in the form of a chip-washer and reader that is capable of accurate and reliable SNP measurement, and which produces an integrated system for SNP scoring that provides higher performance at lower cost is described.

SNPs have many properties that make them a good choice as the primary analytical target for the study of human sequence variation which are particularly important for mapping and discovering genetic factors that are major health threats. Determination of a large number of SNPs in the human population will stimulate many areas of biological research, including identification of the genetic components of disease SNPs are common in human DNA. When individuals are compared, any two random chromosomes have significant differences. There may be anywhere from 6 million to 30 million nucleotide positions in the genome at which non-lethal variation can occur in the human population. Overall, approximately one in every 100 to 500 bases in human DNA may be polymorphic.

SNPs can be used as genetic markers in mapping studies; e.g., for whole-genome scans in pedigree-based linkage analysis of families. A map of about 2000 SNPs has the same analytical power for this purpose as does a map of 800 microsatellite markers—currently the most frequently used type of marker.

When the genetics of a disease are studied in individuals in a population, rather than in families, the haplotype distributions and linkage disequilibria can be used to map genes by association methods. For this purpose, it has been estimated that from 30,000 to perhaps 300,000 mapped SNPs are required.

Genetic analysis can be used in case-control studies to directly identify the functional SNPs that contribute to a particular phenotype. Because only 3% to 5% of human DNA sequence encodes proteins, most SNPs are located outside of coding sequences.

SNPs are important for mapping and discovering genes associated with common diseases because they are more likely to have functional significance than a random SNP. Many processes and diseases result from or are influenced by complex interactions among multiple genes, including processes involved in development and aging, and common diseases such as diabetes, cancer, cardiovascular and pulmonary disease, autoimmune diseases, psychiatric illnesses, alcoholism, common birth defects, and susceptibility to infectious diseases, teratogens, and environmental agents.

A variety of methods have been used to detect SNPs. Almost all of these begin with sample preparation and amplification of individual sequences or their transcripts by PCR. Almost all require sequencing or separation by gel electrophoresis. The need for sequencing and electrophoresis greatly complicates the development of good, efficient, cost-effective technology for automated, higher-throughput detection of SNPs. The one method that does not require sequencing or electrophoresis—the probe-array (DNA chip) technologies being developed by Nanogen (San Diego, Calif.) and Affymetrix (Santa Clara, Calif.)—is expensive and complex. Although DNA chip technologies are finding use in some large industrial research laboratories because of their ability to handle multiple probes on a single chip, they are far too costly for most applications.

Because of the relative rarity of SNPs in the population, appropriate scoring of SNPs requires the analysis of large numbers of samples. The methods described herein are economical based on peptide nucleic acid (PNA) probes in low-density arrays. The quantitative electrochemical PNA probe approach has high inherent specificity and sensitivity. Advantages of this approach to the measurement of SNPs include avoiding expensive equipment, gel electrophoresis, use of radioisotopes, and other time-consuming methods of traditional molecular biology; inexpensive mass-production for use with multiple samples and probes; small size and less extensive operator training.

Moreover, the electrochemical detection system can be used with crude samples, and its operation is independent of variations in optical clarity; and it is amenable to scale-up of the throughput and automation using conventional fluid-handling technologies.

Significant differences exist between PNA probes and DNA probes that are believed to make the use of PNAs in conjunction with appropriate detection low-cost and robust. PNAs are nucleic acid bases joined by a peptide backbone. PNAs recognize complementary DNA and RNA by Watson-Crick base pairing (Egholm et al., 1993), but PNA probes work faster and more specifically in hybridization and affinity-capture techniques and they can more easily be incorporated into arrays for simultaneous probing of multiple samples. Multiple-sample capability, combined with accurate analysis in a very economical system, should provide substantial savings in time, labor, and cost—and thereby greatly facilitate progress in scoring SNPs in the human population.

The basic principle of detection of SNP sequences is represented below:

PNA Probe Complementary to SNP Sequence
+SNP Sequence--------------> Strong Signal
+Normal Sequence-----------> Weak Signal An electrochemical signal indicative of probe hybridization to the target sequence is produced by an enzyme-catalyzed reaction.

The electrochemical analyzer measures signals quantitatively and provides a read-out indicative of normal or altered gene sequences. The method is well-suited to a multi-phase development.

Single base-pair variations, or deletions may be detected. Significant differences in electrochemical signal between wild-type and variant sequences of the BRCA1. gene were observed. Homozygous wild-type samples were distinguished from heterozygous samples with a single base deletion (1323dG), or a single base change (1177 G/A) in the BRCA1 gene.

4.5 Detection of Pathogenic Organisms in Marine and Freshwaters

*Pjiesteria piscicida* and *Pfiesteria*-like organisms associated with large fish kills have emerged as the most recent new threat to environmental and human health posed by harmful algae. Detection and identification of *Pfiesieria* is complicated by the fact that it can assume very different shapes, making normal microscopic identification methods inapplicable. No discriminating culture methods have been developed. At present, only scanning electron microscopy methods that involve treatments that reveal morphological sub-structures are successful in discriminating between *Pfiesteria* and many other small dinoflagellates. Molecular methods of detection are clearly needed.

The emergence of strains of microbes with increased virulence and toxicity adds to the burden of human illness and death associated with microbial diseases and contributes a sense of urgency to find better ways to detect and identify them. Current methods of culture and microscopic examination usually fail to identify specific strains, take days to carry out, and are thus inadequate to meet public health needs. Some microbes cause chronic disease, others cause acute infections that spread rapidly, while others act only through toxins that they release. Some have long periods of latency, with chronic or acute disease being evident only years later. Some cases of microbial disease reach epidemic proportions, as in the case of water-borne *Vibrio cholera*, the microbe responsible for cholera epidemics. Less well known are *Giardia* cysts and *Cryptosporidium* oocysts that infect both humans and other animals and can be transmitted via water supplies. They can adversely affect human health by persistent diarrhea, weight loss, and malaise. With proper treatment and good immune system response these are readily cured, but they can be life-threatening to AIDS patients and other immune-compromised people.

Sub-clinical microbial infections contribute to the development of some chronic diseases that were not previously suspected to be associated with microbes. Studies suggest that infections with one or more of the water-borne enteroviruses can be latent for many years before symptoms like chronic fatigue are manifest. Detection of the infectious nature of chronic disease has eluded scientists forced to depend on antibody-detection systems, because persistent infections rarely involve significant antibody production. *Cytomegalovirus* may cause serious infections and disease symptoms in persons who have received organ transplants and in persons whose immune systems are weakened. In 5%–25% of infected children, symptoms such as neurologic and developmental problems, sight and hearing deficits, and dental abnormalities appear several years after birth. As another example of latency, many duodenal ulcers have been traced to the presence of *Helicobacter pylori*, a bacterium discovered only in 1982. It can infect and reside in people for decades, then progress to form ulcers in 10%–20% of those infected, sometimes resulting in stomach cancers. In Western countries, 20% of the population below the age of 40 and 50% of those above 60 are infected. Low socioeconomic status is predictive of *H. pylori* infection.

Growing populations can overburden sanitation systems and create conditions that allow the introduction and spread of food- and water-borne organisms (Wilson, 1995). Outbreaks of *Vibrio cholerae* reappeared in the Western Hemisphere in 1991 (Tauxe et al., 1995). In the former Zaire, more than half a million Rwandan refugees from civil war suffered devastating outbreaks of cholera and dysentery in squalid camps (Goma, 1994). In 1993, standard municipal water-purification practices that failed to clean the local drinking water effectively contributed to a major outbreak of cryptosporidiosis in Milwaukee, Wis. (MacKenzie, 1994).

Nucleic acid sequence differences in ribosomal RNA (rRNA) can be used to differentiate between pathogenic and non-pathogenic microbial strains, where most methods would fail to discriminate between them. These molecular methods have the potential to provide much more rapid microbe detection and identification than is possible with traditional culture methods and microscopic assays. Moreover, levels of gene expression, indicated by levels of messenger RNA (mRNA), are also amenable to quantification by molecular assays, so that toxin-producing and non-toxin-producing stages of microbial growth could be distinguished by molecular assays.

Probes for microbe detection may be either DNA, RNA, or PNA-based. To enhance both sensitivity and selectivity, PNA probes represent preferred classes of capture and detector probes. Synthesis and characterization of electroactive PNA probes for the target microbes to be detected may be obtained from a variety of sources using standard molecular biological techniques for oligonucleotide probe preparation.

The formation of specific hybrid duplexes between PNA-based probes and target rRNA is promoted under highly stringent conditions at the sensor. In one completed system, there is the choice of using lysed cells, total cellular RNA, or any other RNA subset as the starting target material, although the enhanced sensitivity and selectivity of the present methods do not generally require RNA isolation. Hybridization is followed immediately by wash and electrochemical detection. Any target RNA (or other materials) that does not participate in probe hybridization is removed by wash steps after capture of the probe-target hybrid at the electrode surface. The captured probe-target hybrid is detected as a current generated at the sensor when the substrate for the enzyme-label is added. (Processing steps such as these may be simplified using automated methods, robotic sample handling devices, or other high-throughput sample processing equipment).

In general, hybridization may be performed in buffer containing formamide, an environment that tends to give very low background by promoting specific RNA:PNA duplexes rather than non-specific hybridization. Preferably, single stranded PNA probes and conditions may be employed that tend to minimize or remove any non-specific RNA:DNA and/or RNA:RNA structures but that do not interfere with PNA:RNA hybridization.

4.6 Clinical Diagnosis of Sepsis

Sepsis or bacteremia results from the infection of blood by pathogenic bacteria. The same organism can cause either clinical state, depending on the susceptibility of the patient and the concentration of the bacteria in their blood. Considering the distinction between two possible clinical outcomes of infection illuminates the need for new diagnostic tests. In the least-threatening case, bacteremia, patients are ill, typically with low-grade fever that may not be associated with other clinical symptoms, and blood cultures are positive. These patients may require no hospitalization, and some can even recover without antibiotic treatment. In contrast, in the more serious manifestation of bacterial infection, sepsis, patients are very sick and exhibit high fever and low blood pressure. These patients are typically admitted to the hospital and given intravenous antibiotics even before blood-culture results are obtained-primarily because of the current one- to three-day wait required for blood-cultured results. This latter type of infection can cause extremely high fever, shock, and even death if not treated promptly and aggressively. Clearly it is desirable to be able to test rapidly for infection when present at low levels so that appropriate treatment can be administered in a timely fashion.

There are currently no commercially available nucleic acid-based diagnostic tests for bacteria in blood. Several nucleic acid-based tests use blood or serum to identify specific viruses, and are either being used for research or are in the process of being reviewed for FDA approval. The one exception is Roche's Amplicor test, which is an FDA-approved nucleic acid test for HIV in blood. All of these tests target pathogenic viruses and are designed for high-throughput, quantitative assessment of viral load from relatively small sample sizes. For example, Roche's next-generation "Ultra-Sensitive" Amplicor test for HIV will use only 0.5 mL of blood. This volume is completely inadequate for the diagnosis of low-level bacteremia, for which as few as 10 colony-forming units per milliliter can be significant in terms of disease progression, and for which a 10-mL sample of blood is currently taken from adults for culture.

The current state of the art for clinical diagnosis of bacterial blood infection (bacteremia or sepsis) is whole-blood culture. Blood samples for analysis are collected from the patient and injected into commercial blood-culture tubes containing nutrient media. The tubes are placed in an incubator/detection instrument for a period of time, during which a variety of organisms may grow. This type of analysis can take from one to three days, resulting in a lengthy and often critical period of uncertainty for determination of appropriate patient care. Often, after waiting days for these results, cultures are negative and the physician is left to guess at the etiology of the sickness.

While most of the commercially available blood-culture systems are capable of detecting a wide range of microorganisms, the successful and accurate detection of specific bacteria can vary, depending on the infecting organism and the growth medium (Zaidi et al., 1997; Welby-Sellenriek et al., 1997). Thus, the reliability of the culture method for detecting low levels of target organisms (with low target levels being common in bacterial tests) depends a great deal upon the survival and growth of the target species in a single medium. Based on conventional blood-culturing methods, the incidence of false-positive cultures is reported to be as high as 8% (Bates et al., 1990, Weinbaum et al., 1997), with a significant proportion of these erroneous results being due to contamination from the skin by Coagulase-Negative Staphylococci during collection of blood (Souvenir et al., 1998). This organism is also responsible for a significant portion of true-positive blood infections [10% to 20%] (Souvenir et al., 1998).

One advantage of the present invention is in the development of a nucleic acid-based test for bacterial RNA that does not rely on blood culture. Such a test can utilize a single blood sample to rapidly determine (<~2 hours) the presence of infection as well as to provide information about the identity of the causal organism(s). Such advantages lead to more-rapid and appropriate patient care, reduced hospital stays, and lower healthcare costs. Likewise, the method employs single-tube, hands-off blood-processing means for diagnosing bacterial infections.

Moreover, the present method reduces the need for processing large volumes of blood as is typically required for conventional culture-based diagnoses. This is a particularly critical issue with neonates and children, from whom it is inherently difficult to obtain volumes of blood in excess of 1 to 2 mL and within whom low-level bacteremia is common (Sullivan et al., 1982; Isaacman et al., 1996; Schelonka et al., 1996; Kellog et al., 1997). The facility of the present methods in readily identifying three human pathogens have been demonstrated using, three different microbes (*E. coli, Salmonella*, and *Chlamydia*) with both conventional DNA and PNA detector probes.

The current generated by probe-target hybridization results from detection of species specific rRNA in a blood sample containing bacteria and interaction of the enzyme label horseradish peroxidase (HRP) with its substrate near the surface of the sensor. The sensors are coated with neutravidin for capture of biotin-labeled probes or primer sequences hybridized to the target sequence. The first approach relies on direct detection of rRNA released from viable bacteria. Data shown in FIG. 5 were generated by the direct measurement of rRNA released from bacteria.

Capture probe was labeled with biotin at the 3'-end and the detector probe was fluorescein-labeled at the 5'-end. Antifluorescein-HRP was added, and the current caused by the HRP-catalyzed reaction was measured at a fixed electrode potential (−100 millivolts). The signal increased linearly with target concentration. No signal above negative control was seen with rRNA from three other microbes tested, indicating specificity of detection of specific rRNA target.

Data in FIG. 6 were obtained by incorporating an enzymatic nucleic acid amplification-step, the polymerase chain reaction (PCR), prior to electrochemical detection. As with direct detection of rRNA targets, the electrochemical signal obtained was proportional to the concentration of target in the sample.

4.7 Hepatitis Screening Using Electrochemical Molecular Biosensors

Hepatitis is a serious, widespread infectious disease marked by inflammation and destruction of the liver. Hepatitis is often the underlying cause of cirrhosis and liver cancers. After two decades of unsuccessful searching, the agent responsible for non-A, non-B hepatitis has been identified as hepatitis C virus (HCV) (Choo et al., 1992).

According to the U.S. Surgeon General, there are 30,000 new cases of HCV in the United States every year, and some 10,000 die from the disease. It is the most common cause of liver failure in patients who require liver transplantation. Beyond that, the Department of Health and Human Services blood-safety advisory committee has recommended that anyone who was given blood between 1987 and 1992 should be tested.

Diagnostic tests that provide greater specificity are under development, and treatments in addition to interferon are undergoing clinical trials (BonNovsky, July 1997), <odp.od-.NZH.gov/consensus>). Sequencing several clones of HCV from around the world has revealed significant genetic diversity among strains (Esumi and Shikata, 1994). This genetic diversity is proving to be important, both diagnostically and in terms of understanding the pathophysiology and treatment of HCV infections.

Current diagnostic testing for HCV is based on both antibody detection and detection of viral RNA (Nicoll et. al., 1996). None of these tests is suitable for HCV assessment in an outpatient setting. In attempts to improve sensitivity of the antibody-detection assays, proteins from the capsid region of the viral genome have been included and the assay has been formatted as a recombinant immunoblot assay (Ortho Diagnostics). These tests are licensed for laboratory use. The third-generation version (Chiron, Emeryville, Calif.) includes synthetic HCV peptides and recombinant viral proteins, which further increases the sensitivity and specificity of the assay and also allows earlier detection of seroconversion.

Antibody assays, however, are not suitable for HCV genotyping. Moreover, they inadequately reflect viral loads because of variations in individual immune response systems. Serological diagnosis lags exposure by weeks to months. Nucleic acid-based tests are clearly preferable.

The detection of viral RNA associated with HCV is also being employed with PCR and RNA-capture assays. An assay known as RT-PCR, which uses an initial reverse transcriptase (RT) step to convert viral RNA to cDNA, followed by PCR amplification, has been developed in a number of formats (www.medscape.com). PCR has been applied to several regions of the HCV genome, but detection of the highly conserved 5'-UTR is most common.

4.8 Detection of Polio Virus

Polio virus was grown, harvested and used to demonstrate direct detection and quantification of polio virus in crude samples. A simple sandwich hybridization assay method was used, with unoptimized probes labeled with electroactive enzymes. Polio virus was clearly detected in crude samples containing $2.5 \times 10^7$ plaque forming units (pfu)/ml. Results for direct detection without amplification may be further improved by using signal-amplification techniques, combined with PNA rather than DNA probe sets. FIG. 12 shows a more sensitive test based on RT-PCR followed by detection with the disclosed biosensor system.

4.9 Malaria

Malaria has a public health and economic impact in many countries outside the United States (NIAID, 1997). The burden of this disease is felt around the world, with some 300 million to 500 million cases and up to 3) million deaths per year (NIAID, 1997). Beyond those immediate deaths, malaria has "an even larger impact on disability-adjusted life years (DALYs), an indicator developed to estimate the disease burden for purposes of evaluating the cost-effectiveness of interventions." Globally, malaria is responsible for the loss of 35,728,000 DALYs—more than 38 times the DALYs predicted for hypertension (Olliaro et al., 1996).

Malaria has made a comeback, with the appearance of drug-resistant strains of the parasite. Malaria continues to claim an estimated 2 to 3) million lives annually and to account for unknown morbidity in the approximately 300 to 500 million people infected annually (WHO, 1996). Furthermore, it has been predicted that malaria will increase dramatically in the world's temperate regions—where it is now practically non-existent and that it will also increase in tropical regions (Martens et al., 1995).

Historically, vaccines are the most cost-effective and simple-to-administer method of controlling infectious diseases. Unfortunately, the costs of vaccine development using current methods are high. Moreover, a survey conducted by the Wellcome Trust found that global expenditure on malaria research-only a portion of which involves vaccine development-was only $84 million in 1993 ("Malaria Research: An Audit of International Activity," 1996).

Since it is known that immune responses against the liver and blood stages of the malaria parasites' life cycle can protect against malaria, researchers are attempting to identify relevant immune mechanisms and targets, determine if immune responses complement the immunity of pre-bloodstage vaccines, and develop and test vaccines against the liver and blood stages of the parasites' life cycle (Hoffman et al., 1998; Stanly, 1998). However, current state-of-the-art nucleic acid microarray technology is inadequate for the systematic studies needed for identifying genes as potential drug and vaccine targets, especially in later disease stages. The probe assay methods disclosed herein are capable of quantitatively detecting—without PCR or other target-amplification—parasite mRNA present at very low levels in human cells.

The *Plasmodium falciparum* genome consists of approximately 30 million bases in 14 chromosomes. The complete sequence of Chromosome 2 has already been determined and made public (Gardner et al., 1998). The sequences of the remaining chromosomes are being determined, and the information can be accessed from the GenBank as it becomes available.

Malaria is an important model for genomics-based vaccine development because of the need for a vaccine and because of the complexity of the disease. One concern for an antibody-based vaccine is the natural selection of parasites resistant to the vaccine. It is important to develop vaccines that block multiple stages of the parasite, including the transmission stage (Miler and Hoffman, 1998).

RNA isolated directly from human samples or culture can be simultaneously assayed for the presence of many specific malarial mRNAs. For example, the thousands of probes for electrochemical detection might consist of specific segments of known genes, or of expressed sequence tags that could be traced back to a certain gene or clone.

Using the present methods, genes that are unique to a stage of growth of a particular pathogenic parasite, drugs or vaccines can be targeted to these genes or their products. The search for malaria vaccines has-thus far been unsuccessful, possibly because the vaccine-development techniques have previously been confined to a limited number of pathogen targets (Wakelin, 1996).

DNA array technology may now be used to identify more appropriate pathogen antigens for vaccine development that are expressed during key stages of the parasite's growth. Likewise, electrochemical assays may be used to analyze malarial gene expression during, the varied life stages of the malarial parasite that have previously been technically difficult or impossible to carry out.

4.10 Cancer and Detection of Genetic Mutations

Cancer starts as a genetic error in the division of a single cell. Typically, that error is corrected or the immune system identifies and destroys the aberrant cell before it can multiply to form a cancer-but when the system breaks down, fast-growing tumors form and invade healthy tissue or metastasize through the blood vessels and lymph system to other areas, where new malignant tumors grow. Cancers are thought to be genetic in origin, resulting from multiple events involving many genes functioning at various levels of expression over time. Genetic factors and microenvironmental variations contribute to virtually every aspect of the disease and affect both its severity and progression. Differences in the genetic makeup, shifts in growth stages, and varied microenvironments of individual tumors make cancer therapy difficult. Consequently, molecular analysis of tumor samples that can clarify these differences is becoming an increasingly important avenue for understanding, the relationship between genetic, microenvironmental, and other contributors to the disease and its progression and ultimately for effective treatment.

It is now recognized that carcinogenesis is an extremely complicated process in which many factors play distinct roles. These factors can be grouped into two general categories: 1) molecular genetics, and 2) tumor microenvironment. Certain key aspects of the evolution of cancer (e.g., invasive and metastatic potential) are not easily amenable to study—yet with the right technology, important scientific advances can be made on the apparently intractable question of cancer.

Each tumor is in an individual disease state with distinct genetic makeup. At the molecular level, more than 100 oncogenes have been identified that are able to transform normal cells into tumorigenic cells when mutated or expressed at a high level. Many "tumor suppressor" genes have also been identified whose inactivation renders the cell more susceptible to oncogenic transformation. In many instances, multiple oncogenes or tumor-suppressor genes are involved in the same etiological process. The process is complicated, involving the interplay of many oncogenes and tumor-suppressor genes. Gene expression in a tumor is dynamic, being constantly selected and modified by the tumor microenvironment, which is highly unstable (Kimura et al., 1996). As a consequence, different treatments are called for at different times.

Tumor microenvironment plays an equally important role in tumor development. Tumor microenvironment consists of tumor cells and normal host tissue such as stromal cells, vascular endothelial cells, and immune cells. Host cells play significant roles in tumor development. The process of tumor growth from the single-cell level involves interaction of tumor cells with normal host-tissue cells. Host cells and secreted factors are essential for the survival of the tumor cells. They participate in some of the most important processes of tumorigenesis, such as angiogenesis. Many factors such as vascular endothelial growth factor are at least partially provided by normal cells (Fukumura et al., 1998).

There is evidence that genetic and microenvironmental factors interact and modify each other during tumor development and treatment, as illustrated by the mutant p53 gene. It has been shown that under conditions of hypoxia, which occurs in most if not all solid tumors, the mutant p53 gene confers overwhelming selective growth advantage to tumor cells (Graeber et al., 1996). Those cells expressing mutant p53 grow at a normal rate under hypoxic conditions, while those with wild-type p53 stop growth or die by apoptosis. This relationship of genetic predisposition/microenvironmental selection also exists for other tumor-related phenomena, such as cell-cycle control, DNA repair, signal transduction, and angiogenesis. Angiogenesis, for example, is essential for tumor growth and is stimulated by tumor hypoxia. Genetic instability, a feature common to most cancer cells, can result from interaction between genetic and microenvironmental factors (Reynolds et al., 1996). The tumor microenvironment exerts selective pressure on the tumor cells, and those tumor cells possessing advantageous genetic mutations survive better and eventually dominate the tumor cell population.

Profiling tumor microenvironment and genetic makeup at the molecular level provides information for tumor diagnosis and treatment. It is estimated that some 60,000 to 100,000 genes are encoded in the human genome, and that some 15,000 to 30,000 genes are expressed in any given cell. Of these, scores or even hundreds may play a role in tumor development. At the microenvironmental level, it is likely that many genes from both the host and the tumor cells interact and cooperate in creating and responding to the tumor's dynamic conditions. These include the constant need for angiogenesis, stress from intermittent hypoxia and reoxygenation cycles, and nutrient depletion resulting from poor blood supply and continued growth.

Various techniques exist for the detection of differential gene expression in two closely matched cell populations. These include subtractive cloning (Sagerstrom et al., 1997), differential display (Liang and Pardee, 1992), serial analysis of gene expression [SAGE] (Velculescu et al., 1995), sequencing of expressed sequence tags [ESTs] (Adams et al., 1991), and the newer hybridization-based technologies. While all of the above-mentioned approaches have yielded significant and meaningful results, most of them have potential drawbacks. Subtractive cloning, SAGE, and ESTs tend to be labor-intensive and costly and therefore not suitable for use on a routine basis. For example, SAGE and ESTs entail the use of hundreds or thousands of DNA sequencing reactions, which are prohibitively expensive under most circumstances.

Two recent areas of progress make hybridization-based technology feasible and superior to other screening techniques. The first is the rapid advance of the Human Genome Project, which is identifying new genes and unique EST's every day. As of Nov. 30, 1998, 17,5831 human genes or complete coding sequences had been identified, and 52,277 unique EST's had been catalogued. For mice, the figures were 7,497 genes and 12,342 unique EST's. The second advance is the emergence of the so-called DNA microarray or gene-chip technology. The technology involves the positioning of highly condensed and ordered arrays of DNA probes on glass slides or nylon membranes. Up to 50,000 DNA fragments, each representing an individual gene, can be placed on a single 2"×3" glass slide, and up to 5,000 can be placed on a 2"×3" nylon membrane. The resulting "microarrays" can then be used to examine the presence and concentration of these genes.

To identify differentially expressed genes in two closely related cell populations, current technology generally involves three simple steps: 1) generating fluorescent or radioactive probes from the mRNA of the two populations; 2) hybridizing the labeled probes with two identical arrays; and 3) obtaining signals of hybridization from arrays by use of a phospho-imager. Once the signals are recorded, a detailed comparison of gene expression from the samples is conducted easily with commercially-available software.

The present invention is significantly improved over conventional methods and provides a more-versatile, higher-throughput system that can be easily tailored to the specific research or clinical need for a specific set (usually 5 to 20) of user-defined genes. This technology provides measurement of between 96 and 384 elements in a microtiter plate format in less than an hour-far faster than any current method. The gene-detection array design can be easily tailored to meet the needs of specific applications. This technical approach involves the direct measurement of low levels of RNA on a sensor array.

4.10.1 Factor V

Techniques for allele-specific amplification of Factor V wild-type and mutant genes have been described (Kirschbaum and Foster, 1995). The allele-specific amplification of Factor V genes has been repeated followed with electrochemical detection using Rapid PCR™ detection methodology. The forward primer has the same sequence as that reported by Kirschbaum and Foster, except that it is labeled with a biotin at the 5'-end. Two discriminating reverse primers have the same sequences as those reported by Kirschbaum and Foster, but are modified with a 5'-fluorescein. These primers are discriminatory based on homology of the Y-nucleotide of the reverse primers with either the wild-type or the mutant DNA sequence. PCR amplification was performed as described by Kirschbaum and Foster (1995), and amplification products were captured directly onto sensors through the biotin:avidin interaction. The double-stranded DNA was conjugated with anti-fluorescein HRP, washed and treated with the substrate and mediator to generate a current. PCR amplification products were also monitored by agarose gel electrophoresis to confirm that double-stranded products generated are of the predicted size. Null DNA controls and controls of known genotype were included as well. A high signal is expected only when the discriminating primer finds homology with one of the alleles in the sample.

4.10.2 VEGF Gene Expression

Angiogenesis is a process by which new blood vessels sprout from pre-existing capillary beds. Malignant tumors are in constant need of angiogenesis due to their aggressive growth which requires new vessels to replenish various nutrients. The hypoxia condition that is prevalent in the solid tumor microenvironment acts as a trigger for the activation of the various angiogenic factors which are normally dormant. Vascular endothelial growth factor (VEGF) is one of the more important tumor angiogenic factor so far identified. It is a potent cytokine that targets endothelial cells and induces their proliferation. It has been shown to be important in wound healing, tumor growth and metastasis, all of which require the formation of new vessels. VEGF is strongly and rapidly induced by hypoxia (Shweiki et al., 1992). Additionally, its expression has also been shown to be closely correlated with tumor progression and tumor prognosis in human patients (Crew et al., 1997). In animal models, agents that target VEGF itself or its receptors are effective in inhibiting tumor growth (Borgstrom et al., 1996; Lin et al., 1998). The significance of VEGF in cancer prognosis and treatment is well-recognized.

Poly A messenger RNA can be 1% to 4% of the total RNA and a low copy number mRNA may be as rare as 1/100,000 of the poly A RNA. To detect 5 copies per cell, approximately $10^6$ cells or 1 $mm^c$ tissue would be required using the disclosed methods. Detection of mRNA employs gene specific nucleic acid probes, a colloidal gold sensor array and a small electrochemical instrument for automatic detection and processing. Signals from a particular element in the array are indicative of the presence of a specific mRNA in that sample. Formation of specific hybrid duplexes between probe and target RNA is promoted under highly stringent conditions at the sensor. The method provides a choice of using total cellular, total cytoplasmic, poly A mRNA or any other RNA subset as the starting target material although the enhanced sensitivity of the approach usually does not mandate poly A selection. Hybridization is followed immediately by wash and electrochemical detection. Any target DNA that does not participate in probe hybridization is removed and the specific target mRNA detected at the sensor. In general, hybridization is performed in buffer providing an environment that tends to give a very low background by promoting specific RNA/PNA duplexes rather than non-specific hybridization. Single-stranded PNA probes are used under conditions that tend to remove any RNA/DNA and/or RNA/RNA structures but do not interfere with PNA/RNA hybridization.

PNA probes consist of 10 to 15 PNA residues. Such probes should possess a sequence at least a portion of which is capable of binding to a known portion of the sequence of the mRNA in areas of low secondary structure. Low or high salt and elevated temperature conditions are suitable for use with PNA probes. Electrochemical detection may be performed with differential pulse amperometry or intermittent pulse amperometry. The pulse methods provide for discrimination between redox events near to or remote from the electrode and can be used to reject undesirable background signals.

Correct choice of target cell population is important for successful identification of an appropriate set of molecular markers. Cell line 4T1 is a spontaneously arising mouse mammary adenocarcinoma cell line that shares many characteristics with malignant metastatic human breast cancers when tumors are grown from this cell line in syngeneic BALB/C mice (Aslakson and Miller, 1992; Miller et al., 1983). The cells produce spontaneously metastasizing cells while the primary tumor is in place. Primary sites of metastasis include lungs and liver similar to human breast cancer, where 24% to 77% and 22% to 62% of patients have metastases, respectively (Rutgers et al., 1989; Tomin and Donegan, 1987). Preliminary data indicate that injection of $10^5$–$10^6$ cells subcutaneously injected consistently result in growth of tumors in BALB/C mice. There are advantages in using a syngeneic mouse tumor model instead of zenograft human cancer model in breast cell cancer cells. Syngeneic tumor model uses a mouse strain with an intact mouse immune system which has been shown to participate in tumor growth and tumor microenvironment. Additionally, non-tumor cell mRNAs which may constitute a significant percentage of the tumor mass can also be detected. The non-tumor cell population plays a significant role in tumor growth and development. With increasing availability of both mouse and human gene sequences identification of human homologs can usually be achieved by well known methodologies.

4.11 Use of Probes in Electrochemical Detection

The present invention couples probe technology with sensitive electrochemical detection. "Probe" is intended to include biological probes, oligonucleotide probes, gene probes, peptide nucleic acid probes and similar terms.

The basic system for electrochemical detection is one of coupled reactions, such as the HRP electrode assays previously developed (U.S. Pat. Nos. 5,217,594; 5,225,064; 5,334,296; 5,368,707; 5,391,272 all incorporated herein by reference, and also described in O'Daly et al., 1992; Zhao et al., 1992; Henkens et al., 1987; 1991; 1992a; 1992b; Stonehuerner et al., 1992; Crumbliss et al., 1990; 1992; 1993). An electrode is bonded to a capture probe which, in turn, binds a target nucleic acid sequence with high specificity.

In certain cases, the electrode is further prepared by binding to the immobilized capture probe/target-nucleic acid sequence a detector probe which is conjugated to an electroactive reporter group, for example horseradish peroxidase (HRP), which can transfer electrons. When suitably combined with a reference and a working electrode, the capture probe/target-nucleic acid sequence/detector probe/electroactive reporter group complex, in the presence of a substrate or activator for the electroactive reporter group, such as peroxide, and an electron transfer mediator, causes a measurable and quantifiable electrical current.

4.11.1 Homogeneous Hybridization and Electrochemical Detection

The assay chemistry can be conveniently divided into four general steps: (1) sample treatment, (2) hybridization, (3)) hybrid capture, and (4) detection.

4.11.2 Sample Treatment/Cell Lysis

Samples are collected and concentrated or lysed, as required. Appropriate adjustment of pH, treatment time, lytic conditions and sample modifying reagents may be made in order to optimize reaction conditions. Such modification techniques are well known to those of skill in the art and are described in Maniatis et al., 1989 and Ausubel et al., 1989, incorporated herein by reference. Although amplification steps are generally undesirable, procedures that include short amplification prior to measurement may be desirable in some cases. Such assays by the disclosed method would still have shortened analysis time compared to conventional assays, because it is unnecessary to amplify target nucleic acid to the same degree.

4.11.3 Hybridization

Hybridization of the target DNA and oligonucleotide robes is generally carried out in an aqueous solution which contains an excess amount of dissolved (capture and/or detector) probes. Hybridization proceeds rapidly, because both the target DNA and probes are in a homogeneous hybridization system rather than a heterogeneous hybridization system.

As used herein the term "complement" is used to define the strand of nucleic acid that will hybridize to a first nucleic acid sequence to form a double stranded molecule tinder stringent conditions. Stringent conditions are those that allow hybridization between two nucleic acid sequences with a high degree of homology, but preclude hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of other compounds such as formamide in the hybridization mixture.

Thus one will desire to employ varying conditions of hybridization to achieve varying degrees of selectivity of probe towards target sequence. For applications requiring high selectivity, one will typically desire to employ relatively stringent conditions to form the hybrids, e.g., conditions of high stringency where one will select relatively low salt and/or high temperature conditions, such as provided by about 0.02 M to about 0.15 M NaCl at temperatures of about 50' C to about 70' C. Such selective conditions tolerate little, if any, mismatch between the probe and the template or target strand.

It is generally appreciated that conditions can be rendered more stringent by the addition of increasing amounts of formamide, which serves to destabilize the hybrid duplex in the same manner as increased temperature. Thus, hybridization conditions can be readily manipulated, and conditions can be readily selected depending on the desired results.

In a homogeneous hybridization system, hybridization of probes and target DNA occurs in solution. Probes and target DNA do not need to be transferred to a solid support surface, such as a nitrocellulose filter, in order for hybridization to take place. In conventional filter hybridization methods such as Southern blot hybridization (Southern, 1975), the target DNA or RNA is immobilized on a filter membrane and then allowed to hybridize with the probe molecule. After the conventional hybridization reaction is complete, excess probe molecules are removed by washing the filter and the labeled hybrids are detected by autoradiography or by a non-radioactive detection method.

In these conventional methods the rate of hybridization is very slow because the target is present in low concentration and immobilized on a surface (Flavell et al., 1974). Overnight or longer incubations and autoradiographic exposures are sometimes required to obtain good sensitivity. Protocols of the claimed invention are faster, because they are designed to-increase hybridization rates by carrying out reactions in small volumes of solution and capturing the DNA hybrids afterwards (Albretsen et al., 1990). Thus the amount of time, labor, expense and technical expertise required is reduced.

4.11.4 Hybrid Capture

The present invention allows identification of specific nucleic acid sequences in crude samples. In certain cases, it is desirable to use two different probes, i.e. a capture and a detector probe. This hybridization technique can be more specific than single probe hybridization, because two hybridization events must occur in order to generate a signal. The electrodes are coated with molecules, such as streptavidin or avidin which are designed to capture target nucleic acid capture probe hybrids. Alternatively, electrodes are coated with the capture probe itself, designed to allow capture of the target or a target/detector probe hybrid.

In embodiments that include a detector probe, a strong catalytic current is produced when target nucleic acid probe hybrids that are immobilized on the working electrode surface and labeled with an electrochemically detectable label, such as HRP, are exposed to an amperometric potential in the presence of a substrate, e.g. peroxide. The result of catalysis by the HRP label is a flow of current between the working electrode and another electrode, either the reference electrode in a two electrode system or the counter electrode in a three electrode system. The current is measured by a monitoring device, as referred to earlier.

Equations 1–3 illustrate the electrochemical detection of HRP bound at an electrode. An electron transfer mediator is used in this system. A preferred mediator is ferrocene monocarboxylic acid (Fc).

$$HRP_r + H_2O_2 + 2H^+ \rightarrow HRP_o + 2H_2O \quad (1)$$

$$HRP_o + 2Fc \rightarrow HRP_r + 2Fc^+ \quad (2)$$

$$2Fc^+ + 2e^- (electrode) \rightarrow 2Fc \quad (3)$$

At the molecular level, capture at the colloidal gold electrode or biosensor puts the HRP in close proximity to the working electrode, where it generates a current in the presence of peroxide. The peroxide is added, Equation 1, after allowing the probe and target sequences to hybridize. The electrochemical detection assay exhibits rapid response with a good signal-to-noise ratio.

Another electron transfer mediator that can be used in the claimed invention is 3,3',5,5'-tetramethylbenzidine.

The hybridization solutions may comprise buffers of relatively low stringency, as determined by previous hybridization studies.

4.11.5 Detection

The sample containing hybridized target DNA/detector probe, or hybridized capture probe/target-DNA/detector probe or hybridized capture probe/target DNA, is applied to a "test strip" which contains the electrode biosensor and comprises at least a working electrode and a reference electrode. A third, counter, electrode is also present if quantitation of target nucleic acid concentration is desired. Hybrids are captured at the working electrode surface by reaction of the capture probe with the electrode biosensor or by the hybridization of the target-DNA/detector probe hybrid with the capture probe that is already bound to the biosensor.

Although an excess of capture probe is present, either bound directly to the biosensor or in the aqueous hybridization solution, no catalytic current or electrochemical signal is generated by these non-hybridized capture probes because these capture probes are not also attached to an electroactive reporter. In one preferred embodiment, the capture probe is biotinylated and the electrode biosensor is coated with colloidal gold and avidin, preferably a synthetic avidin.

4.11.5.1 Electrochemical Measurement of HRP-Enzyme Label

The DNA and RNA assays described herein preferably involve quantitative measurement of an enzyme label capable of generating an electrochemical signal. An exemplary label for the electrochemical sensors of the present invention is horseradish peroxidase (HRP). Alternatively, other peroxidases, microperoxidases, and phosphatases, such as alkaline phosphatase (AP) may also be used for this purpose. In the final step of the assay, the amount of enzyme label bound to the detector probe-target-capture probe hybrid captured on the sensor's surface is measured using the electrochemical monitor with either intermittent pulse amperometry (IPA), differential pulse amperometry (DPA), or DC amperometry (DCA). Measured signal, which is a function of the enzyme surface activity, is proportional to the concentration of target nucleic acid in the sample.

Prior to the measurement, unbound HRP has to be washed from the sensor, and then HRP-label activity is measured using a stabilized mixture of 3,3',5,5'-tetramethylbenzidine (TMB) and hydrogen peroxide ($H_2O_2$). $H_2O_2$ is a substrate for HRP and TMB serves as an electrochemical mediator or electron shuttle.

The enzymatic reaction is as follows:

$$H_2O_2 + 2H^+ + HRP_{red} \rightarrow HRP_{ox} + 2H_2O$$

In this process the HRP is being converted from its original (active towards $H_2O_2$) form to its oxidized form ($HRP_{ox}$). The enzyme is regenerated by TMB:

$$2TMB + HRP_{ox} \rightarrow 2TMB^+ + HRP_{red}$$

In solution containing sufficient-concentrations of both $H_2O_2$ and TMB, the formation of $TMB^+$ can be used as a measure of surface activity of the HRP. Nucleic Acid Biosensor detection is based on electroreduction of $TMB^+$ at the surface of the sensor. The biosensor applies pulses of potential at –100 mV (vs. Ag/AgCl reference electrode) and measures current due to the following reaction:

$$TMB^+ + e^- \rightarrow TMB$$

Reaction (3) generates reduction current that is directly proportional to the concentration of TMB+ and, consequently, to the amount of HRP label captured on the sensor.

4.12 Types of Electrochemical Detection

4.12.1 Conventional DC Amperometric Detection

Most electrochemical systems employing electrochemical sensors such as those for blood glucose, oxygen, or hydrogen peroxide, as well as immunosensors and gene-probe sensors, involve measuring., currents using DC Amperometric Detection, (FIG. 7), which is also referred to as Amperometric Detection. In this method a constant potential is continuously applied to the working electrode and, after allowing sufficient time (usually, several seconds), a "steady state" current is measured. The current results from an electrochemical process induced by the applied potential, in which the analyte electrochemically either reacts at the working electrode or is involved in a reaction cycle with some other species reacting electrochemically. In order to have analytical utility, the measured current signal has to have predictable and stable correlation to the concentration of the analyte. The same, of course, has to be true for any other detection method. The major drawback of DC Amperometric Detection is that the properties of the electrode interface change in time as a result of continuously applied potential. The change, usually called electrode fouling, may be due to adsorption of sample components (e.g., proteins, lipids) on the surface of the sensor which changes the current signal and makes it less predictable. The measurement tends to be slow as sufficient time is needed to allow the electrode surface to equilibrate with the tested solution.

4.12.2 Pulsed Electrochemical Detection

Pulsed Electrochemical Detection (PED) is used almost exclusively in liquid chromatography. PED (Johnson and LaCourse, 1990) is an amperometric detection method in which a potential waveform comprised of a sequence of pulses is imposed on the working electrode in a detector system. It is a non-stationary system. That is, solution containing analytes flows through a cell and passes by the detector. PED has been applied to numerous organic compounds following their separation by high performance liquid chromatography (HPLC). PED is best known for its superiority in detecting carbohydrates and other compounds whose complex surface electrochemistry makes their measurements using conventional, DC Amperometric Detection unreliable or insufficiently sensitive. Despite its popularity in HPLC, Pulsed Electrochemical Detection, or for that matter any other kind of Pulse Amperometric Detection, has not been used with stationary systems such as those involving electrochemical sensors.

In PED the potential is applied as a series of fast (i.e. about 50–400 ms) pulses of constant amplitude. The current is measured at the end of the detection pulse while other pulses, of similar or higher amplitude, may be used to precondition the electrode surface either by electrochemical cleaning (i.e., desorption) or reactivating (i.e., regeneration of active groups on the electrode surface). The advantage of this approach is that the electrode fouling due to adsorption of the product of electrochemical reaction, or other sample components, can be greatly diminished.

4.12.3 Differential Pulse Amperometry

In the present invention, two new approaches, Differential Pulse Amperometry (DPA) and Intermittent Pulse Amperometry (IPA), for the measurement of current signals using disposable sensors were developed because the limitations of the preceding detection systems did not allow detection of target nucleic acids either with sufficient sensitivity to eliminate amplification steps or in a stationary system.

Differential Pulse Amperometry (DPA) involves applying a series of two pulses (FIG. 7). The first pulse is a longer "base" pulse set at the "resting" potential, i.e. where no significant charge transfer should be expected, or at potential that would allow measurement of a background current. The second pulse is a shorter detection pulse with sufficient potential to electrochemically oxidize, or reduce the analyte, or one of the products or reagents participating in the analyte reaction in solution phase or on the electrode surface. Current is measured at the end of both pulses and the subtracted value is used as a signal. By proper selection of the base potential, variable effects of background currents are eliminated, which is of great importance in applications employing disposable sensors.

4.12.4 Intermittent Pulse Amperometry

In Intermittent Pulse Amperometry (IPA) a very similar approach to that used in Differential Pulse Amperometry is applied, but a significant difference is that instead of the "base" pulse during which controlled potential is applied to the working electrode, the working electrode is disconnected from the potentiostatic circuit of the monitor or amperometer (FIG. 7). Thus the electrode is allowed to "relax or rest," i.e. assume its natural potential where truly no charge transfer is occurring. The boundary conditions are restored in a natural way, i.e. not imposed by any applied potential. Thus, the current which is measured at the end of the detection pulse reflects the activity of the enzyme (or other redox) label attached to the electrode surface, and is not obscured by the accidental charge transfer process which could be the case when the base potential selected in the Differential Pulse Amperometry is not truly the open circuit potential. Surprisingly, IPA greatly improves the sensitivity of the present invention. One would not expect that disconnecting the electrode would actually improve its function and the sensitivity of the assay.

Advantages of both differential and intermittent pulse measurement schemes include:

1. Electrode fouling is effectively eliminated. The measurement time, when a potential is applied to the electrode, is significantly reduced (from seconds to milliseconds) and, consequently, adsorption of reaction product(s) or other sample components is minimized, helping to maintain a steady response of the electrode.

2. The measurement is faster. Currents are measured on the millisecond time scale while the time scale of seconds or minutes is used in conventional DC Amperometric Detection. One to two seconds is sufficient to establish a "steady state" current signal and a quantifiable measurement.

3. A high rate of current measurement (about 5–50 Hz can be used, but about 10 to 25 Hz sampling rates are preferred) allows for rapid acquisition of a large number of data points and effectively reduced background signal interference.

4. Additional improvement of the signal-to-noise ratio can be accomplished by data averaging, or FFT (fast fourier transformation) smoothing.

Intermittent Pulse Amperometry (IPA) is an electrochemical detection technique developed for DNA assays and immunoassays. IPA measurements involve a series of millisecond pulses of the same or variable potential applied to the working electrode, separated by longer periods when the electrode is disconnected from the potentiostat circuit. Current signals, which are measured during the last 100 microseconds of each pulse, are significantly larger than those measured by conventional DC ("Direct Current") Amperometry (DCA). This is due to reduction of concentration depletion created by continuously applied potential in DCA. In comparison to Differential Pulse Amperometry (DPA) IPA offers a better control of currents measured for one form of a mediator (e.g., reduced form) in the presence of the other form (e.g., oxidized form). When, for example, the conversion of TMB to $TMB^+$ by the HRP enzyme is used for detecting an HRP label, small concentrations of $TMB^+$ must be measured in the presence of large excess of the reduced from of TMB. Under those conditions IPA offers better sensitivity and superior signal stability compared to DCA and DPA.

In measurements involving probes and disposable colloidal gold based sensors, IPA is more suitable and advantageous. For example, when colloidal gold-Neutravidin (cAu/NA) biosensors were used with captured biotin-HR-P label, IPA produced significant enhancement of the sensitivity compared to the conventional DC Amperometric Detection. Further, after a 5 minute incubation of 1:20,000 dilution of biotin-HRP stock solution in phosphate buffered saline (PBS) and bovine serum albumin (BSA) buffer on the biosensor at room temperature, the measured currents were approximately 7–8 times higher in pulse detection compared to the conventional amperometric detection.

4.12.4.1 Intermittent Pulse Amperometric Detection Systems For Multi-Electrode Sensors The IPA measurement involves a series of millisecond pulses of the same potential applied to the working electrode, separated by longer periods when the electrode is disconnected from the potentiostat circuit. Current signals, which are measured during the last 100 microseconds of the pulse, are significantly larger than those measured by conventional DC ("Direct Current") Amperometry. This is due to reduction of the effect of concentration depletion created by a continuously applied potential.

Several units of the Pulse Amperometric Monitor (PAM) operating in the IPA detection mode were produced. The hardware and firmware of the Amperometric Monitor were modified to accommodate new pulse detection functions. Moreover, the PAM monitor is capable of simultaneous detection and quantitation of several targets using dual sensor arrays. Operational features of the new Pulse Amperometric Monitor include (a) three modes of operation including Intermittent Pulse Amperometry, (b) "One Touch" change of setup and calibration using a Calibration/Setup Button (touch memory chip), (c) 2-line Liquid Crystal Display, (d) battery or AC adapter operation, (e) RS-232 Port and a computer program that allow the operator to change parameters, and save and analyze the data, (f) a single-key START operation.

As a direct consequence of introducing IPA detection, the sensitivity of direct detection DNA/RNA assays was improved by a factor of 10. Using IPA, the inventors were able to measure, attomolar quantities of targets. Additional attributes of the IPA detection, which are particularly beneficial for assays involving complex samples such as blood, include (a) reduction of electrode fouling effects, (b) faster measurement, (c) noise reduction, and (d) sensor array detection capability.

Data presented in Table I illustrates very good precision and sensitivity of dual sensor strips in IPA measurements involving a synthetic DNA target. These data demonstrate that despite the smaller electrode size and concurring measurements conducted on all electrodes of the strip, the dual sensors produce (a) lower background signals, (b) similarly low detection limits, and (c) almost the same levels of reproducibility as standard sensors.

Data-Shown in Table 2 were obtained during simultaneous measurements of test solutions containing different combinations of three BRCA1 targets at sub-nanomolar concentrations, using the multi-sensor Pulse Amperometric Monitor. A cocktail of detector probes and a sensor array containing capture probes immobilized on different electrodes were used in this experiment. The data demonstrate the ability of the multi-target detection system to (a) detect the presence and absence of a target sequence in sample, (b) differentiate between different target sequences, and (c) generate a sensitive signal that can be used for determination of target concentration.

TABLE 1

COMPARISON OF THE SENSITIVITIES OF STANDARD cAu/NA SENSORS AND SMALLER DUAL cAu/NA SENSORS USING SYNTHETIC DNA TARGET

| | | Negative Control | | | Positive Control | | | Detection |
|---|---|---|---|---|---|---|---|---|
| | | Avg. signal | RSD | Ratio/* | Avg. signal | RSD | Ratio/* | Limit, pM |
| Standard Sensor | | 0.039 | 14% | — | 3.213 | 26% | — | 0.50 |
| Dual Sensor | Left WE | 0.010 | 9% | 3.8 | 0.568 | 28% | 5.7 | 0.49 |
| | Right WE | 0.010 | 8% | 3.9 | 0.503 | 22% | 6.4 | 0.50 |

Negative Control Diluant
Positive Control 0.1 nM 76mer

TABLE 2

ILLUSTRATION OF MULTI-TARGET DETECTION CAPABILITY OF DNA/RNA DETECTION SYSTEM

| Sensor Array | Immobolized Capture | Corresponding BRCA1 Target | Test Solution #1 | | Test Solution #2 | | Test Solution #3 | | Test Solution #4 | | Test Solution #5 | |
|---|---|---|---|---|---|---|---|---|---|---|---|---|
| | | | Target Conc., nM | Sensor Signal, μA | Target Conc., nM | Sensor Signal μA | Target Conc., nM | Sensor Signal μA | Target Conc., nM | Sensor Signal μA | Target Conc., nM | Sensor Signal μA |
| Sensor #1 | BRCAl-ex11-517 | Ex11-1249-1335WT | 0.0 | 0.09 | 0.5 | 0.91 | 0.0 | 0.06 | 0.5 | 0.86 | 0.5 | 1.29 |
| Sensor #2 | BRCAl-ex11-381 | Ex11-358-432 | 0.0 | 0.13 | 0.2 | 1.56 | 0.2 | 1.83 | 0.0 | 0.20 | 0.2 | 1.39 |
| Sensor #3 | BRCAl ex2-178 | Es2-WT-syn | 0.0 | 0.05 | 0.2 | 1.41 | 0.2 | 10.5 | 0.2 | 1.10 | 0.0 | 0.03 |

4.12.5 Intermittent Differential Pulse Amperometry

Intermittent Differential Pulse Amperometry (IDPA) is an electrochemical detection technique that has a great potential for conducting biosensor measurements with improved sensitivity. A prototype of the detection monitor capable of conducting IDPA measurements has been designed, constructed and tested.

IDPA measurements involve a series of millisecond double-step pulses comprising a base potential pulse followed by a detection potential pulse without interrupting the contact with the potentiostat between the pulses. Base pulses have a distinctively different potential relative to the detection pulse. It can be used to precondition the surface before each detection pulse or to restore the boundary conditions disturbed by the processes taking place during the detection pulse. For example, +200 mV potential can be used as base potential and −100 mV can be used as the detection pulse. Consecutive double-step pulses are separated by a longer period when the electrode is disconnected from the potentiostat circuit. Currents are measured during last 100 microseconds of the base pulse and the detection pulse. Current measured at the detection pulse, or the difference between the currents measured at detection pulse and base pulse, can be used as current signal for the purpose of detecting the presence or determining the quantity of the target in test sample. The effect of intermittent double pulse is an increase in sensitivity of measurement and additional reduction of electrode fouling effect due to interference or surface reaction products adsorbing or otherwise distorting the performance of the sensor.

4.12.6 Enzymatic Detection

In Enzymatic Detection the steps following capture of the hybrid nucleic acid on the sensor involve binding an electroactive enzyme as a reporter group (such as HRP conjugated to an anti-fluorescein antibody) via fluorescein, and then detecting the current generated when the enzyme is activated.

4.12.7 Electrochemical Differential Thermal Scanning

The electrochemical differential thermal scanning method utilizes oligonucleotide hybridization to interrogate DNA sequences. Multiple probes are immobilized on the solid support and a single hybridization is performed with a pool of allele-specific oligonucleotide probes to the target gene. Alternatively, the allele-specific oligonucleotides can be immobilized on the solid support. Enzymatic or non-enzymatic electroactive detection groups may Se used. An electron transfer mediator is used to carry electrons between the electroactive detection group label and the surface of the electrode. The catalytic current at excess mediator is directly proportional to bound label concentration which in turn is proportional to the level of captured probe target hybrid. Measurement of the catalytic current is made at a fixed potential. Sensor electrodes contain an ultra-micro colloidal gold array conjugated to Neutravidin that binds to biotinylated labeled capture probes on the surface of the sensor. Native or synthetic targets hybridized to the capture probe then can be detected by hybridization to a detection probe carrying fluorescein. Anti-fluorescein antibody conjugated to horseradish peroxidase is used to enzyme-label the detection probe and provide an electroactive label. See FIG. 8.

4.12.7.1 Detection of Alterations in Synthetic Oligonucleotide Targets.

Synthetic targets were used to study conditions under which alterations in DNA melting might be observed for each mutation. Four pairs of synthetic oligonucleotide targets were designed and synthesized, each of which spanned one of four different regions in the BRCA1 gene. One target of each pair was completely wild-type in sequence, the second target of each pair contained the indicated mutation. Targets and probes were combined in hybridization reactions and detected on disposable electrochemical sensors following a wash of the sensor at different temperatures.

Detection of a single base change (I 177G/A) using differential thermal scanning is typical of the ability of the system to detect alterations in oligonucleotide targets.

Average signals ranged from 1–10 μA with blank signals 0.1 μA and below. For comparison among multiple experiments and for clarity of graphical analysis the data were normalized to the signal at the lowest temperature, which was arbitrarily set at 100. Third order polynomial regression was performed on the normalized wild-type and mutant data sets to obtain melting curve equations. The difference curve Δ was obtained by subtracting the mutant curve from the wild-type curve (FIG. 9A, FIG. 9B and FIG. 9Q.

Additional mutations were studied using similar methods of data collection and analysis. The data for each mutation shown in FIG. 10 were generated under identical conditions. Therefore, direct comparisons between curves can be used to illustrate the consistency of the data with the expected theoretical outcome. In one example, the 11 base pair BRCA1 deletion 1201d11, the peak in the temperature-dependent Δ curve was observed at 52 C. In this case the capture probe was relatively long, 27 nucleotides, having a GC base composition of 48%. The single base-pair deletion, 1323dG, gave a smaller peak in the Δ curve at 49 C. The capture used to detect this mutation was short, having 16 nucleotides of homology with the target and a GC base composition of 50%. Thus, two different types of mutation gave clearly distinct peaks in Δ curves at similar temperatures.

The 1201d11 mutant target (with 11 bases deleted) has only 16 nucleotides of homology with the 27 nucleotide probe, while the 1323dG mutant target (with 1 base deleted) had 15 nucleotides of homology with the 16 nucleotide probe. Thus, the similar peaks for these different mutations were consistent with the theoretical molecular biology considering, that the length of homology between the mutant targets and their respective capture probes differed by only 1 nucleotide. Similar melting temperatures for the mutant targets would therefore be expected and were in fact observed with these two examples. The peak in the Δ curve for the third mutation, 1177 G/A, was also experimentally distinguishable, but in this case the peak was at 33 C, much lower than for the other two mutations. The lower temperature was consistent with melting of the mutant target from a relatively short capture probe (16 nucleotides), having a low GC base composition (only 25%).

These data demonstrate that differential thermal scanning can be used to screen for mutations and to distinguish different types of mutations, including large and very small deletions, and targets with very small changes melting temperature such as those involving single base-pair changes. In addition, the dependency of the data on the length and base composition of the capture probes suggests that with further examination of multiple types of mutations and capture probe composition, a useful data base of information can be generated. This data base can be used to write an algorithm that could predict the type and length of mutation in an unknown DNA sample based on the length of the capture probe, its base composition and the peak in the Δ curve obtained relative to a normal sample.

4.12.7.2 Detection of Heterozygous Mutations in Mixtures of Synthetic Oligonucleotide Targets.

Synthetic targets were used separately to mimic the homozygous wild-type (+/+) and homozygous mutant (−/−,) conditions, or combined in equal proportions to mimic the heterozygous (+/−) condition for the BRCA1 point mutation 1177 G/A. The three test samples were analyzed as described in Protocol D. The melting curve for each set was subtracted from the homozygous wild-type to generate Δ curves (FIG. 16).

Comparison of the wild-type target to the homozygous mutant target mimic gave a Δ curve with the highest amplitude (stars in FIG. 16). In contrast, the comparison of a wild-type target to another wild-type target gave a Δ curve with low amplitude and no apparent peak (diamonds in FIG. 16), and comparison to the heterozygous mimic target gave a Δ curve that fell between the two (triangles in FIG. 16). These data demonstrate that the Electrochemical Differential Thermal. Scanning method distinguishes the heterozygous condition from either the homoyzgous wild-type or the homozygous mutant.

5.0 EXAMPLES

The following examples are included to demonstrate preferred embodiments of the invention. It will be appreciated by those of skill in the art that the techniques disclosed in the examples represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Materials and Methods 5.1.1 Preparation of Colloidal Gold/Streptavidin (cAu/SA) and Colloidal Gold/NeutrAvidin (cAu/NA) Electrodes Streptavidin solution 1 mg/ml (salt-free) was purchased from Pierce (Rockford, Ill.). Gold trichloride ($HAuCl_4$ $3H_2O$) (Fisher Chemical Co.) was used to prepare colloidal gold sols with a particle diameter of approximately 300 Å by the method of Moremans et al. (1985). Colloidal gold (cAu) sol stock (0.05 mg/ml) was centrifuged at 7,000 rpm for 50 minutes. Supernatant was removed as much as possible. The red pools were collected and distilled $H_2O$ added so that the Absorbance of the sol at 1:100 dilution in water was 0.5 at 518 nm (OD=50). The concentration of this centrifuged cAu sol is about 2.5 mg/ml.

One milliliter of Au sol and 200 μl streptavidin solution were mixed together and 20μ bicarbonate solution (1M $NaHCO_3$, pH 8.5) was immediately added in a glass test tube. The solution was stored in a refrigerator before use. Salt-free NeutrAvidin (Pierce, Rockford, Ill.) was dissolved in H20 to make a 2 mg/ml solution. Distilled water, 500μ and 2 mg/ml NeutrAvidin (in $H_2O$), 200 pl, were mixed together and 12μ of 1 M $NaHCO_3$, pH=8.5 (freshly filtered) was immediately added. The solution was stored overnight in a refrigerator before use.

Colloidal Gold/Avidin was mixed (1:2) with absolute ethanol (1 part cAu/SA or cAu/NA, 2 parts ethanol). cAu/Avidin, 2.5 μl, was deposited on each working electrode and allowed to dry completely at room temperature. StabilCoat is a polymer used to coat bio-molecular layers. StabilCoat (50 μl, BSI) was added to each working electrode and incubated for 10 minutes at room temperature. The StabilCoat was aspirated from the electrode and the sensor was allowed to dry briefly then bagged with desiccant for storage.

The current range for a Gene-Probe sensor is from 0 nA to about 12,000 nA. Sources of minor variation between different batches of sensors may be the cAU/Avidin sol, cAu/Avidin strip or the Biotin-HRP solution. Hence conditions may be optimized if desired. Variables to optimize include: 1) sensor printing parameters; 2) colloidal gold formulation and deposition; 3) polymer coating; and. 4) electrode size and configuration. A relative standard deviation (RSD) of 5% or less to sensors is preferred.

5.1.2 Nucleic Acid Samples

Fresh or recently isolated biological samples are used for DNA isolation. Alternatively, synthetic DNA targets and human DNA from commercial sources may be used.

5.1.3 Assay Conditions Using a Model System

Target DNA, an oligonucleotide comprising 21 contiguous guanosines and 27 contiguous thymidines and designated as G21-T27, was placed in varying amounts of solution at concentrations of 0 or 3.5 nM.

The biotin-poly-cytosine capture probe was attached to the electrode and immersed in the target DNA solution. The detector probe, Fluorescein-A23, (twenty-three contiguous adenosines bonded to at least one fluorescein molecule), was added to this solution to a concentration of 14 nM, and incubated at room temperature for 15 minutes to allow hybridization. Test strips were then washed with Phosphate Buffer Solution (PBS)/0.5% BSA. Anti-Fluorescein-HRP conjugate (25 μl of a 1:1000 dilution in PBS/0.5% BSA from 1–2 mg/ml solution purchased from Biodesign International) was added to the test strip and incubated at room temperature for 5 minutes. The test strips were washed with PBS/O.5% BSA. The consequence of the described procedure is the localization of the electrochemically labeled target nucleic acid at the test strip's working electrode. TMB/hydrogen peroxide substrate solution was added to the test strip and the current measured.

Alternatively, when the capture probe, the detector probe, and the target nucleic acid were dissolved in the hybridization solution the following conditions were used. PBS/0.5% BSA (25µ) containing biotin-poly-cytosine, Fluorescein-A23, and anti-Fluorescein-HRP conjugate was mixed on the electrode with target DNA, G21-T27 (25 µl) in PBS/0.5% BSA, and incubated at room temperature for 15 minutes. The strips were washed with PBS/0.5% BSA. The consequence of the described procedure is the localization of the electrochemically labeled target nucleic acid at the test strip's working electrode. TMB/hydrogen peroxide substrate solution was added and the current was measured.

Sample volume affected assay performance as shown in Table 3. Sample volumes of 100 µl or more yielded the greatest net signal indicative of the target DNA compared to the background signal produced in the absence of any target DNA.

TABLE 3

Effect of sample volume on signal strength.

| Sample Volume (µl) | Current (nA) | |
|---|---|---|
| | 0 nM Target DNA | 3.6 nM Target DNA |
| 10 | 167 | 898 |
| 25 | 165 | 1241 |
| 50 | 129 | 1344 |
| 100 | 151 | 2210 |
| 1000 | 120 | 2199 |

The target DNA was detected regardless of whether the capture probe was attached to the electrode (1 step), was in the hybridization solution with the electroactive label (2 step), or was in the hybridization solution before the electroactive label was added (3 step) (Table 4).

TABLE 4

Comparison of different hybridization protocols.

| Target DNA (fmol/sensor) | i/nA (1 step) | i/nA (2 step) | i/nA (3 step) |
|---|---|---|---|
| 0 | 291 | 210 | 142 |
| 22 | 709 | — | 479 |
| 24.5 | — | 526 | — |
| 65 | 1234 | — | 754 |
| 74 | — | 1039 | — |
| 200 | 2572 | — | 2348 |
| 222 | — | 2811 | — |
| 600 | 3022 | — | 4577 |
| 665 | — | 4825 | — |

5.2 Attachment of Capture Probes to Disposable Sensors

One of the requirements for a multi-target detection is the ability to capture different targets on different sensing elements of a sensor array and detect them simultaneously. There are several methods that can be used for probe attachment to sensors, and several have potential for mass-production of inexpensive, disposable sensor devices. Covalent binding to a carbon sensor is for numerous reasons highly preferred for DNA sensing. The covalent attachment may be carried out using the following procedure:

5.2.1 Preparation of Solutions

EDAC/S·NHS Stock Solution ([EDAC]=0.05 M, [S·NHS]=0.08 M, [Phosphate buffer]=0.2 M, pH=6.5). In a 5-mL Falcon tube weigh 0.048 g of EDAC {1-ethyl-3-(3-dimethylaminopropyl)carbodiimide, SIGMA E-7750, FW=191.7) and 0.087 g of Sulfo-NHS {N-Hydroxysulfosuccinimide, PIERCE 24510, FW=}. Add 5.0 mL of 0.20 M phosphate buffer, pH=6.5, and mix well to dissolve the solids. EDAC/S-NHS Working Solution ([EDAC]=10 mM, [S,NHS]=16 mM, [Phosphate buffer]=40 mM, pH=6.5). Dilute the EDAC/S·NHS stock solution 5 times with de-ionized water.

Oxidizing Treatment Reagent
  2.5% $K_2Cr_2O_7$ in 10% $HNO_3$
Probe Solution
  1-µM dilution of a 5'-amine-terminated DNA probe in de-ionized water.
Oxidizinig Treatment of Working Electrodes
  Deposit 50 µL of Oxidizing Treatment Reagent on a working electrode of carbon sensors (DUPONT ink). Incubate 40 minutes at room temperature. Wash thoroughly with running DI water. Store under water for future use.
EDAC/S·NHS Treatment of Working Electrodes
  Spread 2.5 µL of the EDAC/S—NHS solution on the working electrode. Allow to dry at room temperature.

5.2.2 Probe Immobilization

Spread 5.0 µL of 1 µM 5'-amine-terminated DNA probe solution on the working electrode. Allow to dry at room temperature.

The stability of probe attachment was tested by conducting consecutive tests using the same sensor, with the first test followed by a wash step. Another stability experiment involved soaking the sensor in wash solution prior to using it in the assay. Both experiments showed that biotin-avidin attachment is the least sensitive to prolonged exposures of the sensor to electrolytes, surfactants, and buffer solutions used in DNA assays. Although the covalent attachment is believed to be chemically most stable, a relatively larger fraction of signal is lost due to contact with the same solutions.

FIG. 11 shows the effects of different methods of surface attachment of a capture probe on the sensor's responses to DNA. 1: Covalent binding on pre-oxidized carbon electrode; 2: Covalent binding on untreated carbon electrode; 3: Adsorption on untreated carbon electrode; and 4: Avidin-biotin binding on cAu/NA-modified carbon electrode.

5.3 Gold and Copper PCB Sensors

Electroplated gold and copper electrode PCB sensors have been developed and examined. An electroplated copper dual sensor was tested using the following method: 5 minute incubation with 1:20,000 Bio-HRP, wash, substrate application. At potentials spanning −100 to −700 mV, no signal was detected (using an external Ag reference). Using 500 µL of K-Blue substrate incubated for 30 minutes with 0 and 10 µL of 1:20,000 Bio-HRP, the copper sensor was again tested using an external Ag reference and the Pulse Amperometric Monitor 5.1 in both amperometric and pulse modes, at −100 and −400 mV each. No differentiation was evident between the blank ("0") and ("10") mixtures.

Electroplated gold dual sensors were tested using an external Ag reference, the PAM 5.1 monitor in both amperometric and pulse modes, at −100 mV, with the two substrate/

Bio-HRP mixtures given above (delay=O, 10s, 10 µA). The blank mixture generated an electrochemical signal of +0.03 using the pulse mode, and the "10" mixture resulted in a signal of −0.28. The signals from bare carbon dual sensors under the same conditions were −0.01 and −2.84. The potential applied to the S8 sensor using the Ag external reference was optimized at a value of −150/160 mV. This is the potential at which the blank was the least negative without being positive, while having the best signal to noise ratio.

The sensor was tested using the internal Au reference. Using the same monitor (in pulse mode), a preferred potential was found at −25 mV by applying the "0" and "10" solutions to the sensor across a potential spread from 10 to −300 mV. Solutions having 0, 5, 10, and 15 µL of 1:20,000 Bio-HRP in 500 µL substrate were used to demonstrate the clear electron transfer mediator concentration dependence of the signal at this potential. The current signal values corresponding to the four different concentrations of mediator were (in parallel order): −0.18, −0.34, −0.49, −0.54.

Various electroplated gold single working electrode sensors were tested. The sizes of the working electrodes ranged from equivalent to FIG. 2A, equivalent to FIG. 2B, and smaller than FIG. 2B. The sensors were tested with a range of mediator concentrations. Clear mediator concentration dependence was exhibited, with the smallest working electrode having the lowest blank reading, and likewise the smallest mediator signal for all concentrations. The sicynal observed was directly proportional to working electrode size.

Gold printed circuit board (PCB) sensors were tested using the following method: 5 minute incubation with 1:1,000 Bio-HRP, Wash buffer, K-Blue substrate application. Using the PAM 51 (pulse mode) at −25 mV, target signal was −3.30 µA for S6, while the blank signal was −0.39. As a WE size comparison, the NA-coated carbon dual sensor produced a target signal of −3.65 µA, and a blank of −0.01 at −100 mV.

Strips of 10 gold electroplated working electrodes were tested. The uncoated pieces were tested using the K-Blue substrate/Bio-HRP solutions "0", "5", "10", and "20". Mediator concentration dependence was exhibited, and the best signal-to-noise ratio was seen at a potential of −50 mV (between a test of −25 and −50 mV). The average electrochemical signals generated at the optimum potential were, in order of solution concentration: −0.19, −0.43, −0.52, −0.71.

A 76-mer standard was used to test the performance of the NA-coated gold electroplated sensors in a full-length assay, complete with hybridization, probe excess, and presence of antibody. Using standard NA-coated carbon dual sensors as a control, the assay was conducted using higher than standard concentration of target (1.0 nM). The NA-coated Au sensors used were single working electrodes, dual working electrodes, and strips of 10 working electrodes. At −50 mV for all Au prototypes, and using the dual pulse monitor, the dual working electrode sensors produced a target signal of −2.24 µA, and a blank signal of −0.24. Equivalent in WE size, the carbon NA-coated dual sensors generated a target signal of −2.94, and a blank signal of −0.01 µA (at −100 mV). The smallest sensors generated target signals ranging from −0.50 to −0.91, and a blank signal average of −0.27 µA. The 10 working electrode strips, using the 10-WE prototype monitor, gave an electrochemical signal for the target of ~−1.24 µA, and a blank of −0.40 µA.

In an attempt to reduce the blank signals generated by the Au prototype sensors, the next NA/EtOH deposition (on the same sensors, cleaned and wiped with EtOH and $H_2O$) was followed by the addition of Stabilcoat to the sensors, as well as 0.5% Casein Stabilcoat. The Stabilcoat, or Casein Stabilcoat mixture, was incubated for 10 minutes, aspirated, allowed to dry for 50 minutes, and heat cured in the box oven for 15 minutes at 54° C. A repeat of the same 76-mer assay, however, showed no reduction in the blank signal due to either modification. Two methods of blocking with 0.5% Casein were tested. For one test group of sensors, 0.5% Casein in water was added to the sensor after drying of the NA/EtOH solution following deposition. The Casein solution was allowed to air dry. The other test group received 0.5% Casein in 1×Tris/NaCl—HNa in a pre-soak step before the start of the 76-mer assay (no drying). Neither method produced a clear advantage to blank signal reduction, and the method in which Casein was dried on the sensor reduced the target signal by 50%. Casein is an effective blocker of non-specific binding on a NA-coated surface. The high blank signals were likely due to the reduction of $H_2O$, on the Au sensor, and not to any non-specific binding of the detector probe to the Au WE surface.

In order to diminish the effect of $H_2O$, reduction on the blank signal, further tests were conducted. Using the same 76-mer assay, more negative potentials and more positive potentials (than −50 mV) were employed. The results suggested that more negative potentials increase $H_2O_2$ reduction of the sensor (blank increase), and more positive potentials decrease $H_2O_2$ reduction (blank decrease). Fresh, unused sensors were deposited with NA/EtOH. Using the 76-mer assay, the potential for the smallest working electrode sensor was performed at the more-positive potential of −25 mV, where the blank readings were −0.08 and −0.14 µA, and the target was −0.65 µA. Likewise, the dual working electrode sensor produced blank signals of −0.06 and −0.14 µA at −15 mV, and target signals of −1.71 and −2.19 µA. Overall, more positive potentials reduced the blank signal without adversely affecting the target signal for the Au sensors deposited with NA.

In an additional study using Au sensors, pulse times were varied to further reduce background. The standard pulse time of 10 ms was shortened to 4 ms and lengthened to 20 ms. For dual working electrode and smallest working electrode, an increase in the pulse time shifted the blank values to more positive readings (at their optimized potentials of −15 and −25 mV, respectively). The dual working electrode blank went from +0.02 at 10 ms to +0.21 µA at 20 ms and the target signal remained relatively unchanged despite the variation of the pulse time. On the other hand, the blank increased, or became more negative, at the shorter pulse time.

5.4 Electrochemical Detection and Quantitation of *E. coli*

Two approaches were used for the electrochemical detection of *E. coli*. In the first approach, the capture probe was pre-immobilized on a colloidal gold working electrode biosensor through NeutrAvidin binding. In the second approach, the capture probe, examined at a fixed concentration of 200 µM, was allowed to hybridize to *E. coli* rRNA in solution, along with the detector probe. The hybrid was captured at the working electrode surface through biotin/NeutrAvidin binding. In both cases, the concentration profile of the detector probe was examined using the procedure described under Section Materials and Methods.

5.4.1 Probe Concentration and Hybridization

*E coli* cells were lysed with 0.75N sodium hydroxide for 5 minutes. A hybridization solution containing detector probe was added to the lysate and incubated for 10 minutes at 65 C. The hybrid solution was transferred to a test strip (see FIG. 5) which either included immobilized capture probe or cAu/Avidin and incubated for 10 minutes at 65 C. The sensor strip was washed to remove unbound hybrid HRP-anti-fluorescein, 0.1 ml, was applied to the sensor and incubated for 10 minutes at room temperature. The sensor was again washed and then inserted into a detection monitor. The substrate solution (0.001% hydrogen peroxide) was applied and after about 10 seconds the electrochemical signal was measured by the monitor.

A capture probe was prepared which was biotinylated at the five-prime end and contained the DNA sequence 5'-TCAATGAGCAAAGGTATTAACTTTACTCCC (SEQ ID NO:XX).

TTCCT-3I' (SEQ ID NO:1). The, detector probe contained the DNA sequence 5'-TGAAAGTACTTTACAAC-CCGAAGGCCTTCTTCATA-3' (SEQ ID NO:2), and a single fluorescein (FI) group was attached at the 5' and 3' ends, respectively, such that the probe was labeled with two FI groups.

In the first approach using the immobilized capture probe, increasing the detector probe concentration increased the assay signal. The signal peaked at about 30 nM of detector probe in the hybridization solution. Higher concentrations of detector probe yielded lower signal-to-noise ratios. Data are given in Table 5.

TABLE 5

Detection of *E. coli* (in nA) Using Immobilized Capture Probe

| *E. coli* | Detector Probe | | | |
|---|---|---|---|---|
| 10$^6$ cells/ml | 16 nM | 31 nM | 65 nM | 125 nM |
| 0 | 32 | 28 | 31 | 34 |
| 0.44 | 38 | 45 | 37 | 44 |
| 1.46 | 55 | 80 | 54 | 52 |
| 4.4 | 92 | 175 | 82 | 90 |
| 44 | 1008 | 1270 | 556 | 559 |

In contrast, the second approach (where the capture probe was included in the hybridization solution) yielded greater sensitivity of detection (Table 6). The highest sensitivity was achieved at a detector probe concentration of 100 nM in the hybridization solution. At higher concentrations of detector probe, the signal-to-noise ratio decreased. Based on these results, the preferred conditions for the assay format are 200 nM of capture probe and 100 nM of detector probe in the hybridization solution. This latter format reliably detected 0.5 million cells/ml of sample; whereas, the former approach only detected 2 million cell/ml of sample.

As with most analyses, detection employed an electrochemical pulse analyzer device which generates controlled potential pulses, applies the pulses to the working, electrodes of a cell or sensor and measures current resulting from electrochemical processes stimulated on the electrodes by the pulses.

TABLE 6

Detection of *E. coli* (in nA) Using Solubilized Capture Probe

| *E. coli* | Detector Probe | | |
|---|---|---|---|
| 10$^6$ cells/ml | 25 nM | 50 nM | 100 nM |
| 0 | 43 | 48 | 50 |
| 0.47 | 75 | 85 | 98 |
| 4.7 | 398 | 418 | 520 |
| 47 | 2700 | 2930 | 3440 |

5.4.2 Alternative Probes

To determine if altering the number of fluorescein groups available changed the sensitivity of the assay, detection probes that had different numbers of FI groups attached to SEQ ID NO:2 or that had altered attachments of the FI groups to SEQ ID NO:2 were prepared. These detection probes are summarized in Table 7.

TABLE 7

Generalized Detection Probe Structures

| Number of FL molecules | Probe Structures |
|---|---|
| 1 | 5'-SEQ ID NO:2-FL |
| 2 | 5'-FL-SEQ ID NO:2-FL |
| 4 | 5'-FL-T-FL-SEQ ID NO:2-FL-T-FL |
| 8 | 5'-FL-FL-FL-FL-SEQ ID NO:2-FL-FL-FL-FL |

In addition, a new probe set which is complementary to different regions of rRNA of *E. coli*, was designed to determine if the specificity of detection was influenced by the region of the RNA to which the probes hybridized. The capture probe of the second probe set comprised the DNA sequence 5'-GTCTCACGGTTCCCGAAGGCACATT-3' (SEQ ID NO:3) biotin at the 5' end. The detector probe comprised the DNA sequence 5'-TCTCTGAAAACTTC-CGTGGATGTCA-3' (SEQ ID NO:4) and included two molecules of fluorescein dUTP, one attached at each of the respective ends.

The assay conditions and procedure were the same as outlined above using the second approach in Section 5.4.1 in which the capture probe, 200 nM, and detector probe, 100 nM, were present in the hybridization solution. The *E. coli* sample solution concentration was 30 million cells/ml.

As shown in Table 8, the signal strength increased proportionally as a function of the number of fluorescein moieties present for probes labeled with either one, two or four fluoresceins. The presence of eight fluoresceins did not enhance signal strength possibly due to steric hindrance of the anti-fluorescein HRP conjugate binding to the fluoresceins. The results also indicate that spacing the fluoresceins apart with one thymidyl residue significantly increased signal, possibly through reduced the steric hindrance. With the four fluorescein labeled probe, the sensitivity of detection of *E. coli* was improved to 200,000 cells/ml.

TABLE 8

Effect of Fluorescein Moieties on Signal Response

| Number of Flourescein Moieties | Current (nA) |
|---|---|
| 0 | 30 |
| 1 | 4,000 |
| 2 | 8,000 |
| 4 | 11,750 |
| 8 | 7,500 |

Detection with the second set of probes, utilizing the oligonucleotides shown in SEQ ID NO: 3 and SEQ ID NO:4, was also successful. Results showed increased specificity and sensitivity compared to the first probe set, represented by SEQ ID NO: I and SEQ ID NO:2. With the first probe set the lower limit of sensitivity was about 500,000 cells/ml; whereas the lower limit of detection with the second probe set was about 50,000–100,000 cells/ml. These results demonstrate that the selection of the regions to which the probes hybridize, the assay conditions used, and the concentrations of the probes all affect the sensitivity of detection.

Based on these results, the detection limit of the electrochemical detection is about 0.01 nM, or 50 attomoles/sensor. The lowest noise level that was observed with the cAu/NeutrAvidin sensors for HRP detection was about 20–40 nA, of which about 20 nA is present in the substrate solution alone. Currents were observed to lose linearity above about 10,000 nA. Thus the preferred current detection range for the quantitation of a microbial target is between about 0 nA and about 10,000 nA.

5.4.3 Electrochemical Detection of E. Coli in Meat Extract

In this example it was determined that a food sample did not cause matrix interferences in the electrochemical determination of E. coli.

Approximately 10 grams of beef was cut into approximately 50 pieces (about 200 mg per piece). 40 ml of Butterfields Buffer was added to the meat and shaken for 1 minute. The meat was allowed to settle and the "Meat Extract" was removed and used as described below.

A stock solution of E. coli was diluted 1:10,000; 1:100,000; and 1:1,000,000 and added to the Meat Extract (Meat Extract without E. coli acted as a negative control.) One ml aliquots were placed on 3M Petrifilm Total Coliform/E. coli plates (3M, Minneapolis, Minn.) (a 1:10 dilution of the 1:100,000 sample and a 1:100 dilution of the 1:10,000 sample was used), and 1.2 ml each of these samples were added to a 1.5 mL microfuge tube containing 26 mg of Lennox L Broth (I g Casein Enzymatic Hydrolysate: 0.5 g Yeast Extract: 0.5 g NaCl: 100 mg Glucose). The tubes were shaken and vortexed until the powder was completely dissolved, then incubated at 37 C for 3 hours. Microfuge tubes were spun at 14,000 rpm for 3 minutes and supernatant was removed with a transfer pipet. Cells were resuspended in 75 μl of 0.125 N NaOH and incubated at room temperature for 5 minutes. Probe/Neutralization Buffer (25 μl) (2 M Phosphate/0.9 M NaCl/6 mM EDTA/0.1% SDS) containing 200 nM SEQ ID NO: 1 and 100 nM SEQ ID NO:2 was added to each tube and incubated at 65° C. for 10 minutes. An aliquot (100 μl) of sample was applied to a cAu/NeutrAvidin electrode and incubated at 65° C. for 10 minutes. The electrode was washed with Wash Buffer (GeneTrak, Framingham, Mass.) then incubated with 50 μl of 1:200 anti-Fluorescein-HRP in PBS/Casein at room temperature for 10 minutes and again washed with Wash Buffer (GeneTrak, Framingham, Mass.). Fifty microliters of K-Blue substrate Substrate (Elisa Technologies) was added to the sample/electrode and the current was measured after 10 seconds. The results are shown in Table 9 below.

TABLE 9

Detection of E. coli in Meat Extract

| Sample Dilution (E. coli) | CFU/ml (24 hour Petrifilm) | Electrochemical Current (nA) |
|---|---|---|
| Negative control | 0 | 313 238 |
| 1:1,000,000 | 200 | 759 668 |
| 1:100,000 | 1,900 | 2596 2596 |
| 1:10,000 | 20,000 | OFFSCALE OFFSCALE |

5.5 Electrochemical Detection of E. coli and Salmonella

E. coli and Salmonella were detected using the probes and assay reagents provided by the Colorimetric Gene Trak™ Assays kit with the streptavidin modified colloidal gold electrodes and detection monitor.

Samples containing Salmonella, or E. coli or neither (negative controls) were incubated with a 50:50 mixture of the E. coli and Salmonella detection probes from Gene-Trak (Medford, Mass.) for 15 minutes at 65° C. Aliquots of 100 μl of the samples were then transferred to electrodes and incubated at room temperature for 10 minutes. The electrodes were washed with PBS, 0.5% Tween-20. Fifty microliters of anti-fluorescein-HRP solution was placed on the electrodes and incubated for 5 minutes at room temperature. The electrodes were washed with PBS, 0.5% Tween-20. Current was measured using TMB/Peroxide solution and the detection monitor. The results of electrochemical detection of the bacteria are shown in Table 10.

TABLE 10

Electrochemical Detection of E. coli and Salmonella

| Sample | Current (nA) |
|---|---|
| Negative Control* | 375 |
| Negative Control* | 401 |
| E. coli Positive Control** | 1307 |
| E. coli Positive Control** | 1007 |
| Salmonella Positive Control** | 1731 |
| Salmonella Positive Control** | 1655 |

*A mixture of Negative control solutions provided with the Colorimetric Gene-Trak ™ E. coli and Salmonella assays which contain killed bacteria.
**Synthetic oligonucleotides provided with the Colorimetric Gene- ™ E. coli and Salmonella Assays and diluted 1:3 with bovine serum albumin in aqueous solution.

5.6 Virus Detection Using Electrochemical Sensors

Viral infections are the most common cause of human disease and are responsible for at least 60% of the illnesses that cause visits to a physician (Ray, 1979). Unfortunately, these organisms are also difficult to detect, requiring complex laboratory tests that take days to generate accurate results (e.g., culture), are inadequate in sensitivity and specificity (e.g., monoclonal antibodies), or lack quantitative capability (see e.g., Chan et al., 1990; Wilson et al., 1990; Tenover, 1988; Schofield, 1992; Payne and Kroll, 1991). There is a need for better tests for early diagnosis of viral disease (Garrett, 1994; Brown et al., 1996; Kaufman and Franz, 1996). The electrochemical sensor of the present invention using a nucleic acid sequence detection can rapidly detect, identify and quantify viruses in crude (unpurified) samples in order to provide early diagnosis and follow-up care of viral disease. This same system can be used as a simple, quantitative detector for systems such as reverse transcriptase polymerase chain reaction (RT-PCR) that amplify viral nucleic acid sequences.

Antibody assays for a number of viral diseases are available, but antibodies to the virus are often not detectable until well after onset of disease (see, e.g. Innis et al., 1989). Recent advances in molecular biology have enabled detection of specific DNA or RNA sequences with DNA probes (Wiedbrauk and Farkas, 1995; Kricka, 1993; Keller and Manak, 1989; Lowe, 1986) and have led to development of highly specific assays for detection of a variety of noncul-turable or difficult to culture viruses such as members of the enterovirus family (Robart, 1990) including hepatitis A, B, and C (Jansen et al, 1990; Kaneko et al, 1989; Ichimura et al., 1992).

In the present system, the current above background that is generated when complementary gene probes and targets hybridize indicates that specific DNA or RNA from an organism is present in a test sample. The amount of current generated is a measure of the quantity of the DNA or RNA that is complementary to the probe sequence.

Human pathogens such as poliovirus, hepatitis A virus, human rotavirus, coxsakievirus, echovirus and newer enteroviruses such as Hepatitis E viruses cause serious public health problems throughout many parts of the world (Melnick, 1990). Major pandemics caused by various strains of rotaviruses, result in staggering levels of death from diarrheal illness in infants in developing countries, with total infections estimated at 450 million yearly with a I to 4 percent fatality rate. Hepatitis E viruses, recognized only since 1988 as the cause of epidemic human liver disease, are common throughout topical zones of Asia, Africa, and South America. These and other viral pathogens such as dengue virus are of great concern to human health, since in many cases the diseases they cause can be transmitted from one to many individuals. For example, life threatening hemorrhagic fevers such as yellow fever and dengue have been spread by a human-mosquito cycle of transmission until now dengue is the most serious childhood disease in Southeast Asia.

5.6.1 Materials and Methods 5.6.1.1 Virus Strains

The virus strains employed were polio virus (PV) type I strain OPV (Sabin), PV type 2 strain OPV (Sabin) and PV type 3) strain OPV (Sabin). These were obtained from the Division of Product quality control CBER/EDA of the Food and Drug Administration (Rockville, Md., USA). PV type 1, strain LSC2ab (Sabin) was obtained from the World Health Organization (WHO) reference laboratory of the Institute of Poliomyelitis and Viral Encephalitis (Moscow, Russia).

5.6.1.2 Virus Culture Lines

Hep-2 (human larynx epidermis carcinoma), obtained from the Tissue Culture Department, University of North Carolina, Chapel Hill, N.C., and Vero (African green monkey kidney) obtained from Division of Product quality control CBER/EDA of the Food and Drug Administration, Rockville, Md., USA, cell lines were used for growth and maintenance of polio virus. They were maintained according to the suppliers' recommendations. Briefly, cells were grown in cell culture medium (0.05% Dulbecco's Modified Eagle Medium (DMEM)) with 10% calf serum. Cells were detached from the culture vessel with 0.05% trypsin-EDTA. A subcultivation ratio of 1:4 was typically used for cell passage in fresh media.

5.6.1.3 Virus Culture Methods

Poliovirus was cultured according to standard protocols (Manual for the Virological Investigation of Poliomyelitis, World Health Organization Expanded Programme on Immunization and Division of Communicable Diseases). Briefly, virus was propagated at 37±0.5° C. on healthy confluent monolayers. Cells were washed one time in DMEM without serum before inoculation. Approximately $10^{6-7}$ TCD 50 were used for inoculation. Poliovirus was isolated after 15–17 hours of subsequent culture at the standard temperature.

Titration of poliovirus stocks was accomplished by two methods. In the first case, cytopathic effect (CPE) was determined by inoculation of cell cultures with various dilutions of live virus. Titer is expressed as TCD and is defined as the highest dilution giving CPE in 50% of inoculated cell cultures. The second method involved identifying and counting plaques in inoculated cell cultures under a layer of media solidified with agar. The cell monolayer is washed with DMEM without serum. Virus dilutions were dropped gently onto the monolayers and allowed to adsorb for 20–30 min. Agar media was prepared {140.0 mL DMEM (70%), 10.0 mL calf serum (5%), 1.0 mL neutral red (1:30,000 dilution) ($1.7\times10^{-5}$%), 50.0 mL 2.5% Difco agar (0.62%)}, 5.0 mL of 37° C. agar media was poured gently on top of the monolayers. Plates were protected from light, incubated at 36 C in air+5% $CO_2$. Plaques were counted from 3 to 7 days. Virus titer is presented as plaque forming units (pfu) per mL.

Poliovirus has been grown on Hep-2 (human larynx epidermoid carcinoma) and Vero (African green monkey kidney) cells (Sabin Type 1, LSc 2ab). These have yielded viral titer values ranging from $10^6$ to $10^9$ TCD $_{50}$/ml. Substantial amounts of poliovirus have been isolated from these cultures. This virus is now used routinely in our poliovirus detection assays.

5.6.1.4 Culture of Other Viruses

Cell lines were established for hepatitis A virus and rotavirus. These cell lines include FRhK-4 (fetal kidney, rhesus monkey, ATCC no. CRL-1688), Vero (kidney, African green monkey, ATCC no. CCL-81), and MA-104 (African green monkey kidney, BioWhittaker, Walkersville, Md.).

Rotavirus was cultured using simian rotavir-us SA-II obtained from ATCC/Lot 6WE, ATCC/R/899. The culture line was NIA-104 African Green Monkey Kidney obtained from BioWhittaker/Lot 6CO 942 P:47 The culture medium was modified DMEM. Vero cell suspension was infected by active rotavirus.

5.6.1.5 Polio Virus Processing

Several lysis procedures have been tested for the poliovirus. The procedure developed denatures the poliovirus, allows for probe hybridization and does not interfere with electrode chemistry. Several lysis methods were tested (detergent, guanidinium, commercial RNA isolation kit, and freeze-thawing). Freeze-thawing for 3–5 cycles in dry ice/water bath appears to best meet the above criteria with minimal requirements in terms of time, manipulation or equipment. This combination of culture and lysis is used in direct detection of the Sabin 1 polio virus in tissue culture media.

5.6.1.6 Initial Viral Nucleic Acid Probes

A fluorescein-labeled detector probe and a 5'-biotinylated capture probe with sequences complementary to those of hepatitis A were synthesized. A 62 nucleotide (nt) artificial DNA target was also synthesized corresponding to bases 333–395 of hepatitis A virus RNA.

Initially probes for detection of poliovirus were based on a paper by Bosch et al. These large probes (up to 1400 bases long) were multiply labeled with digoxigenin (DIG). Additionally, two sets of two small probes were designed and used that are complementary to the poliovirus genome. Detector probes were complementary to nt 601–624 and 651–670 (DIG labeled) and 3431–3461 and 3363)–3393 (FI labeled). The corresponding capture probes were complementary to nt 677–706 and 3398–3427. The use of these short probes to detect the single-stranded RNA isolated directly from poliovirus increased the sensitivity and specificity of the reaction, as described in the following sections.

5.6.1.7 Viral Detection Results

For hepatitis A virus, detection of a synthetic DNA 62-mer having the target hepatitis A virus sequence was demonstrated. For poliovirus, detection of virus-specific complementary DNA clone (cDNA) was also obtained. In these studies a simple sandwich hybridization assay method was used. Probes labeled with electroactive enzymes were used so that captured target-probe hybrids would generate a detectable electrochemical signal upon addition of the enzyme substrate. Polio cDNA target was detected, and only blank currents were measured in the absence of the targets.

Some experiments were also performed without probe or system optimization that showed the feasibility of detecting poliovirus in crude samples, without target amplification. For this purpose poliovirus were grown, harvested, and used to demonstrate direct detection and quantification of poliovirus in crude samples. In these studies, as described below, a simple sandwich hybridization assay method used probes labeled with electroactive enzymes. As in the other assays, only captured target-probe hybrids generate a detectable electrochemical signal upon addition of the enzyme substrate. Poliovirus was clearly detected in crude samples containing $2.5\times10^7$ pfu/ml. When experiments used 1 anti-DIG labeled detector probe and 1 capture probe, the average blank was 0.027 μA and the average signal was 0.205 μA. Some experiments were run with multiple probes but these did not improve the signal to noise above that obtained with the single probe sets.

In order to demonstrate a highly sensitive assay for poliovirus using the present detection system, an electrochemical detection system was coupled to a conventional PCR target amplification system. Poliovirus was grown and harvested. RNA was isolated and used as the target. In these studies, poliovirus at clinically relevant levels (5–500 pfu) was detected using the disclosed electrochemical detection system and reverse transcriptase polymerase chain reaction (RT-PCR). The signals generated were proportional to the RNA levels (FIG. 13). Electrophoresis verified that the PCR product was of the expected size.

The electrochemical detection system can readily detect viral RT-PCR products at sensitivity levels that are clinically relevant. This indicates that this system can replace electrophoresis as a PCR product detection method. This detection system may also be applied to detect PCR amplification of any desired viral sequence. Table 11 presents evidence not only of RT-PCR product detection but also of the desired specificity of viral detection.

TABLE 11

| Sample | Modified Primers in RT-PCR | Input PFU | PFU/mL | μA Signal One Step | μA Without Fl probe | μA with new Fl probe Two-step | Gel Band |
|---|---|---|---|---|---|---|---|
| 1. Viral RNA | Fl/Bio | 500 | $5\times10^5$ | — | 0.038 | 0.35 | + |
| | | | | 2.23 | 0.038 | 0.402 | |
| | | | | 2.471 | 0.038 | 0.386 | |
| 2. Viral RNA | Fl/Bio | 50 | $5\times10^4$ | 1.486 | 0.042 | 0.336 | + |
| | | | | 1.349 | 0.048 | 0.208 | |
| | | | | 1.344 | 0.095 | 0.258 | |
| 3. Viral RNA | Bio only | 500 | $5\times10^5$ | 0.033 | 0.028 | 0.277 | + |
| | | | | 0.032 | 0.031 | 0.249 | |
| | | | | 0.028 | 0.066 | 0.277 | |
| 4. Viral RNA | Bio only | 50 | $5\times10^4$ | 0.038 | 0.086 | 0.177 | – |
| | | | | 0.033 | 0.068 | 0.135 | |
| | | | | 0.034 | 0.041 | 0.121 | |
| 5. Vira1 RNA No Rtenzyme | Fl/Bio | 500 | $5\times10^5$ | 0.035 | 0.021 | 0.037 | – |
| | | | | 0.042 | 0.034 | 0.033 | |
| | | | | 0.054 | 0.033 | 0.051 | |
| 6. Plasmid | Fl/Bio | | $\sim10^7$ | 2.339 | 0.034 | 0.543 | + |
| | | | | 2.164 | 0.033 | 0.754 | |
| | | | | 2.234 | 0.041 | 0.708 | |
| 7. No target | Fl/Bio | | | 0.029 | 0.076 | 0.031 | – |
| | | | | 0.036 | 0.105 | 0.027 | |
| | | | | 0.029 | 0.039 | 0.098 | |
| 8. Uninfected RNA | Fl/Bio | 500 | | 0.036 | 0.049 | 0.043 | – |
| | | | | 0.031 | 0.053 | 0.016 | |
| | | | | 0.029 | 0.045 | 0.018 | |

Reverse Transcriptase was omitted from RT-PCR reaction #5 in order to demonstrate that signals were coming from amplified RNA and not a DNA intermediate of viral replication. As described, one-step detection results from capture of Fluorescein-Biotin (Fl/Bio) hybrids at the gold electrode. Two-step detection occurs after the Fl-labeled strand is washed away and a new Fl-labeled probe specific for the target is bound.

As discussed, RT-PCR reactions targeting viral RNA or poliovirus plasmid and containing both a biotin and fluorescein-labeled primer generated a strong positive electrochemical signal. Reactions containing a biotin-labeled primer and an unlabeled second primer produced amplified products, as evidenced by the expected electrophoretic band, but gave no electrochemical signal (as expected). The absence of detectable electrophoretic bands in sample 4 where formation of the second hybrid gave a significant electrochemical signal reconfirms that the sensor assay is much more sensitive than visual inspection ethidium bromide fluorescence in an agarose electrophoretic gel. No signal was observed in the sample from which reverse transcriptase was omitted, confirming that the target of the RT-PCR reaction was in fact viral RNA and not a contaminating DNA intermediate. Samples 1, 2 and 6 illustrate the efficiency of the protocol used to remove the complementary (fluorescein-labeled) strand of the duplex prior to formation of the second hybrid with an added fluorescein-labeled probe. Assays of these samples without addition of the second probe gave signals approaching background levels.

This example describes a rapid Gene-Probe detection system for Polio virus. Polio virus is used as an exemplary enterically-transmitted RNA virus pathogen.

Hep-2 (human larynx epidermoid carcinoma) and Vero (African green monkey kidney) cells were grown in culture and infected with polio virus (Sabin Type 1, LSc 2ab). Types 2 and 3) polio virus can also be used.

The plasmid containing the cDNA for Type I polio virus obtained from American Type Culture Collection, Bethesda, Md. (ATCC) was used in preparation of several detector probes. Detector probes with multiple digoxigenin (DIG) labels were synthesized by PCR using this cDNA, a DIG-labeling kit (Boehringer-Mannheim, Indianapolis, Ind.), and three sets of primers. Two of the three probes (LPD2 and LPD3) were the same as those used by Bosch et al. (1996) for detection of polio virus at $5 \times 10^3$ particles/ml without target amplification. The first probe (LPDI) was generated in a different manner from Bosch et al. (1996) by use of PCR labeling with DIG and was complementary to bases 651–2099 of the polio virus. Another probe (LPD4) complements bases 700–2099 of the polio virus.

Dot blot tests indicated that the probe complementary to bases 3401–4686 of the virus was heavily labeled with DIG, and this probe was used to detect purified polio virus, RNA transcripts, and cDNA for the virus on cAu/NeutrAvidin electrodes in a system that incorporated a 5'-biotinylated capture probe with a sequence complementary to bases 601–625 of Type I polio virus. This capture probe recognizes enteroviruses in general and is useful in the detection of many types of enteroviruses (Nottay et al. 1995).

Results indicated that the DIG labeled probes can be employed to electrochemically detect 100 pM of polio cDNA without optimization of the system. Electrochemical response to the target polio cDNA is high (18,600 nA). Background signal from the multiply labeled DIG probes was acceptable (50 nA).

Related experiments were performed in which RNA was extracted from polio virus and then examined with our electrochemical detection assays, without amplification. Direct detection of the unamplified RNA was shown. Typical results with RNA extracted from $5.7 \times 10^7$ pfu/ml of polio virus were 0.32 µA signal, 0.17 µA blank, with an average sianal to blank ratio of 2.1. Direct RNA detection in these experiments has a poorer signal to noise ratio than was obtained in the direct assays using crude samples reported above.

As shown in Table 12, the electrochemical detection system readily detects viral RT-PCR products at sensitivity levels that are clinically relevant. Electrophoresis requires additional equipment and is relatively more time consuming and cumbersome. Since simple labels are used (Biotin and Fluorescein) this approach can be applied to detect PCR amplification of any desired viral sequence. Table 12 presents evidence not only of RT-PCR product detection but also of the desired specificity of viral detection.

TABLE 12

Electrochemical detection of Polio virus

| Polio; PFU | Current (nA) |
|---|---|
| 0 | 50 |
| 5 | 370 |
| 50 | 1,300 |
| 500 | 3,200 |

5.6.1.8 Electrochemical Detection of Hepatitis A Virus

For hepatitis A virus, electrochemical detection of a synthetic DNA 62-mer having the target hepatitis A virus sequence was demonstrated. Methods and procedures were similar to those described previously.

Noncomplementary viral nucleic acid sequences were used as additional controls in follow-on experiments. Cross-testing the signal response when hepatitis A sequences were introduced in tests with probes for hepatitis A viral sequences, respectively, demonstrated that this approach has the requisite specificity, i.e., only complementary target and probes produce the hybridization that leads to generation of an electrical current.

Results indicated that the this system may be employed to electrochemically detect synthetic hepatitis A virus DNA. Electrochemical response to the target synthetic hepatitis A virus DNA was 16,000 nA. Background signal was acceptable at 50 nA.

5.7 Electrochemical Detection of Sepsis Related Bacteria in Human Blood

A serious problem in modern medicine is the lack of ability to determine rapidly whether or not a patient is septic. In many cases, the knowledge that bacteria (or other pathogens) are present in blood is critical knowledge to the clinician in his/her determination of patient treatment.

Patients may present with high fever, prompting consideration of sepsis as a diagnosis. Standard protocol calls for obtaining a blood sample (up to 20 ml for an adult; as little as 1 ml for an infant). DNA from the blood sample is isolated using standard methods, for example a QiaAmp DNA extraction kit from Qiagen (Chatsworth, Calif.). A vortexing step with glass beads is used to shear the cell wall and membranes of bacteria that may be difficult to lose.

Extracted DNA or RNA samples may be concentrated using Millipore form-in-place technology and probes selected either for particular pathogens or, if desired, for classes of pathogens employing sequence-specific probes as illustrated in earlier examples.

Amplification is next performed, typically using PCR with universal primers such as 8F 5'Bio and 1492 5'PO under selected hybridization conditions, with stringency altered as desired for selectivity as discussed earlier. An aliquot of PCR product is digested for 15 min at room temperature with Lambda exonuclease to render the product single stranded. This is heated at 75° C. for 10 min to heat kill the Lambda exonuclease enzyme. The single stranded DNA product is diluted in 0.5M Tris/NaCl hybridization buffer. Hybridization is conducted at 65'C. Also included in the reaction are either universal bacterial probes or specific probes for bacteria that commonly lead to sepsis, including for example *Staphylococcus, Meningitis* sp., *Streptococcus*.

The probes are modified with a label such as fluorescein (Fl) or digoxigenin (DIG). After hybridization, the mixture is captured on the sensor surface through the biotin avidin interaction. The target nucleic acid/detector probe complex is bound to HRP through binding of an anti-fluorescein or anti-digoxigenin antibody conjugated to HRP. In the presence of an electrochemical mediator and hydrogen peroxide, a measurement is made which is reflective of the amount of bacterial nucleic acid and hence the number of bacteria present in the sample.

The method selectively detects genetic disease DNA from blood samples. It has been shown to detect *E. coli* without cross-reaction with *Salmonella* or *Chlamydia* in an aqueous sample; *Salmonella* without cross reactivity to *E coli* or *Chlamydia*; or detection of *E. coli, Salmonella* and *Chlamydia*.

The particular probes employed with the method are PNA probes, such as Eco-06, Uni-3 and Uni-13 purchased from Boston Probes (Belden, Mass.).

The method also may be practiced without the amplification step although sensitivity is less.

Ten-fold dilutions of an overnight culture of *E coli* (concentration determined microscopically by cell counts and by petri film) were spiked into blood at known concentrations. DNA was isolated using the QiaAmp kit (Qiagen, Chatsworth, Calif.) without modification. A blood only control was included as a test for contamination and for the ability of "universal bacterial primers" to amplify specific nucleic acid sequences from human DNA. PCR amplification with universal primers, EuBact 8F 5'Bio (5'Bio-AGAGTTTGATCCTGGCTCAG3', SEQ ID NO:5) and EuBact 1492 5'PO4 (5' P04-GGTTACCTTGTTAC-GACTTY (SEQ ID NO:6), Relman, 1993), was run to determine a lower limit of detection of *E coli* in blood. Amplification products were visible following agarose gel electrophoresis when the input sample contained $10^3$ *E coli* cells/ml. Lambda exonuclease digestion of the PCR product to generate single-strand target followed by single probe detection using probe (5Fl-T-Fl-GGAGTTAGCCGGTGCT-TCTTCTGCGGGTAAFI-T-Fl (SEQ ID NO:7), originally designed to detect *E coli* specifically) gave a clear signal at the same level of sensitivity ($10^3$ cells/ml). Since the amount of DNA included in the PCR™ was only a fraction of the total sample (10 PL), this represents detection of only 1 *E. coli* cell input (Table 13). There was no amplification of electrochemical signal from the control, human DNA without *E. coli*.

TABLE 13

Electrochemical detection of Sepsis (Blood Bacterial Load)

| Number of *E. coli* cells in Blood | Current (nA) |
| --- | --- |
| Control | 100 |
| 1 | 180 |
| 10 | 325 |
| 100 | 625 |
| 1000 | 1150 |

5.8 Electrochemical Analysis of PCR" Amplification Products

Plasmid DNAs containing either the wild-type exon 11 or a mutant ion (Lund 8) consisting of an 11-base pair (bp) deletion at nucleotide 1201 (codon 361) of the BRCA1 mRNA were obtained (Ambion, Austin, Tex.) and used to study conditions for detection of BRCA1 mutations in plasmid DNA. The polymerase chain reaction (PCR) was used to amplify the BRCAI wild-type (WT) and mutant (Lund8) plasmids according to the recommended protocols provided by the manufacturer. Initially, ~1000 bp products were amplified, denatured at high temperature in the presence of capture and detector probes and then the hybrid captured and detected electrochemically, see FIG. 4. It soon became clear that the double-stranded PCR-generated molecules were not being efficiently denatured. To solve this problem, lambda exonuclease was used to degrade one strand of the double-stranded DNA from a 5'-phosphate group. Reverse primers were designed that were modified with 5'-phosphate. These primers were used in a PCR reaction, followed by digestion with Lambda exonuclease to yield a single-stranded DNA target for hybridization. This procedure is diagrammed in FIG. 13.

BRCA1 plasmids (WT and Lund8) were PCR amplified with an unmodified forward primer and a 5'-phosphate modified reverse primer that were positioned outside the region of the deletion. These reactions produced double-stranded targets (192 bp or 320 bp for wild-type, 181 bp or 309 bp for mutant). The different sizes of the PCR products (WT and mutant) reflect the deletion of 11-bp in the Lund8 mutant. The resulting DNAs were digested with Lambda exonuclease, followed by hybridization with the wild-type probes (BRCA1-360-3'B, BRCA1-WT-408-5'Fl see Table 19). These results are shown in Table 14.

TABLE 14

Electrochemical Analysis of PCR ™ Amplification Products

| Target | Exo (yes/no) | Current (nA) |
| --- | --- | --- |
| None | N/A | 32 |
| WT 192 bp | No | 38 |
| WT 192 bp | Yes | 495 |
| Lund8 181 bp | No | 34 |
| Lund8 181 bp | Yes | 31 |
| WT 320 bp | No | 30 |
| WT 320 bp | Yes | 396 |
| Lund8 309 bp | No | 29 |
| Lund8 309 bp | Yes | 35 |

The data show that there is little or no signal from the undigested PCR products, presumably because the double-stranded DNAs are unavailable for base-pairing with the oligonucleotide probes. After digestion of the phosphorylated with Lambda exonuclease, the products are detectable. The signal from the wild-type products is elevated whereas the signal from Lund8 products remains at background level, indicating good discrimination between wild-type and mutant genes (16-fold and 11-fold differences between signal from the 200 bp and the ~320 bp product, respectively). This result demonstrates the system's capability to detect gene differences.

5.9 Detection of Genetic Diseases

Rapid advances in molecular genetic technology have created an opportunity for development of new, improved tests for diagnosis of human disease. An abundant literature points to the fact that an intensive research effort is underway to identify genetic targets for the diagnosis of cancer. At least twenty genes display the potential for diagnostic value of one or more malignancies. While many of the genes have been characterized quite extensively at the molecular level, their market value awaits further clinical evaluation.

Early diagnosis of human disease in many cases can be done with clinical tests that look for known gene alterations in a patient sample. Diseases such as cystic fibrosis, muscular dystrophy, sickle cell anemia, phenylketonuria, thalassemia, hemophilia, α1-antitrypsin deficiency and disorders of lipoprotein metabolism can be detected in this way (Benn et al., 1987; Lowe, 1986; Landegren et al., 1988; Young et al., 1989; Kricka, 1993). Quantitative analysis of human genes is also needed for analysis of amplified oncogenes (Altitalo, 1987) and in the measurement of gene expression levels in tumors (Slamon et al. 1989). Research on genetic aspects of human disease (for example research on genes such as BRCA1, BRCA2, p53, mutations of which confer a very high cancer risk) and research that looks for the links between causes of cancer (chemicals, radiation, viruses and heredity) would benefit from more rapid detection of altered gene sequences (Kricka, 1993; Benn et al., 1987; Lowe, 1986; Landegren et al., 1988, Young et al., 1989).

In terms of the total number of humans affected, the most serious hereditary cancer risk is associated with breast cancer. Among women who have a blood relative with the disease the risk of developing breast cancer is close to 1 in 5. Two genes that, if mutated, increase a woman's chances of developing breast cancer have recently been identified and genetic tests are available for detecting women who are at greatest risk. But the tests are expensive and time consuming, which means that they are not suitable for large studies that could lead to better understanding of the disease and improved methods for its prevention.

While many scientists are actively developing DNA probes for clinical diagnostic applications the systems for their analysis are often complex, and require semi- or fully-automated amplified probe systems in order to screen large numbers of samples. The biosensors of the present invention present a novel solution by providing a system that can be used without need for amplification of the target DNA, even when the polynucleotide target is present at fairly low levels in the sample, or alternatively, following a genetic amplification procedure when a greater sensitivity for detection of the target molecule is required.

These probe-based identification methods of the present invention can handle in minutes or hours work that have previously taken scientists and technicians days or weeks to accomplish using the conventional detection methods commonly employed by molecular biologists. The current methods avoid major obstacles to the use of gene-probe methods. These methods are less labor and time consuming and require less sophisticated personnel and equipment. The electrochemical nucleic acid probe assays are based on broad enabling technology (Crumbliss et al., 1993; O'Daly et al., 1992; Zhao et al., 1992; Henkens et al., 1992a, Henkens et al., 1992b; Stonehuemer et al., 1992; Crumbliss et al., 1992; Crumbliss et al., 1990; Henkens et al., 1991; Zhao, 1996; Henkens, 1996; Henkens et al., 1997).

5.9.1 Direct Detection of Genetic Sequences

For direct detection, both forward and reverse primers are labeled, such as 5-biotinylated and 5'-fluoresceinated, respectively. PCR amplification was performed and products are captured and detected directly on the sensor, with no subsequent manipulation.

5.9.2 Single-Probe Hybridization

For the single probe hybridization method, one PCR primer is 5'-biotinylated and the other PCR primer carries a 5'-phosphate. PCR amplification is performed, and the phosphorylated strand of the resulting product is digested with Lambda exonuclease (Boehringer Mannheim). The subsequent single-stranded product is hybridized to a discriminating detector probe which is fluoresceinated at either the 5'- or 3'-end of the probe. The single probe-target hybrid is captured on the nucleic acid biosensor and current measured.

5.9.3 Double-Probe Hybridization

For the double-probe hybridization method, one PCR primer is unmodified and the other PCR primer carries a 5'-phosphate. Like the single probe hybridization technology, Lambda exonuclease is used to digest the phosphorylated strand of the double-stranded PCR product, leaving only the complementary strand behind. This product is hybridized with two probes; a biotin-labeled capture probe and a fluorescein-labeled detector probe. As in the single-probe technology, this double-probe hybrid is then bound to the sensor via the avidin:biotin interaction and detected. If care is taken to choose novel capture and detector probes, then the double-probe method of detection affords the greatest specificity of the three testing methods.

5.9.4 Electrochemical Detection of Single Base Substitution Associated with Sickle Cell Disease The sickle cell anemia gene sequence was used as a model to test detection of a single base pair mismatch. Instead of the normal β-globin genotype ($\beta^A\beta^A$, individuals with sickle cell trait have one normal β-globin gene and one sickle cell allele ($\beta^A\beta^S$). Those with sickle cell disease have two sickle cell alleles ($\beta^S\beta^S$) and no $\beta^A$ gene. The probe sequences, one complementary to the normal human β-globin gene ($\beta^A$) and one complementary to the sickle cell β-globin gene($\beta^S$) (Conner et al., 1983) given in Table 15 were used in these studies.

TABLE 15

DNA SEQUENCE OF PROBES FOR NORMAL β-GLOBIN GENE ($\beta^A$) AND SICKLE CELL β-GLOBIN ALLELE ($\beta^S$)

| Gene | DNA sequence | |
|---|---|---|
| $\beta^A$ | 5'-CTCCTGAGGAGAAGTCTGC-3' | SEQ ID NO:8 |
|  | 3'-GAGGACTCCTCTTCAGACG-5' | SEQ ID NO:9 |
| $\beta^S$ | 5'-CTCCTGTGGAGAAGTCTGC-3' | SEQ ID NO:10 |
|  | 3'-GAGGACACCTCTTCAGACG-5' | SEQ ID NO:11 |

A two-probe hybridization format was used with a 60 base single-stranded synthetic target, one fluorescein labeled detector probe and one biotinylated capture probe. With this format several combinations were tested to study their effects on discrimination between the wild-type and mutant gene sequences. Results (Table 16) showed good discrimination between wild-type and mutant gene sequences and led us to conclude that (a) greater discrimination is afforded when the capture probe (rather than the detector probe) is designed to distinguish between the normal or the mutant allele; and, (b) pre-immobilization of the capture probe on the electrode (rather than hybridization in solution) gave best discrimination between the perfect match and mismatch. As expected, temperature and stringency conditions could affect the degree of discrimination obtained.

TABLE 16

Electrochemical Detection of a Single Base Substitution (Sickle Cell)

| Target Type | Target (nM) | Current (nA) with WT probe | Current (nA) with Mutant probe |
|---|---|---|---|
| Wild Type | 0 | 50 | 50 |
| Wild Type | 1 | 950 | 50 |
| Wild Type | 5 | 4,100 | 750 |
| Wild Type | 10 | 6,000 | 1,000 |
| Mutant | 0 | 100 | 450 |
| Mutant | 1 | 120 | 400 |
| Mutant | 5 | 400 | 2,050 |
| Mutant | 10 | 1,250 | 3,400 |

A capture probe designed to be complementary to the wild-type gene sequence gave a significantly higher signal upon hybridization to the synthetic WT target than obtained when the capture probe was complementary to the sickle cell sequence, and vice versa. This demonstrates of the discriminatory capability of the method.

5.9.5 Electrochemical Discrimination of BRCA1 Sequences in Model DNA Targets

For the following, experiment, a single-stranded synthetic DNA target was used that was entirely wild-type in sequence but spanned the Lund8 11 base-pair deletion in the BRCA1 gene (Johannsson et al., 1996). Wild-type probes for capture (BRCA1-360-3'B) and detection (BRCAI-WT-408-5'FI) were designed to recognize the synthetic target, with the aim of generating a hybrid between the target and the two complementary probes. The data in FIG. 6 shows the measurement of the synthetic target using the described system.

A distinguishing detection probe was designed to bind in the same region of the BRCAI target with full complementarity to the specific breast cancer gene mutation, Lund8 (BRCAI-Lund8-414-5'FI). An electrochemical signal with the probes and the wild-type synthetic target was measured. There was excellent discrimination (>70-fold) between the electrochemical signal obtained with the wild-type probe compared to the mutant probe. These results are shown in Table 17 below.

TABLE 17

Electrochemical Detection of Mutation in Synthetic DNA Target

| Sample | Probe mix | Synthetic target | Current (nA) |
|---|---|---|---|
| Blank 1 | WT | No | 25 |
| Blank 22 | mutant | No | 50 |
| WT | WT | Yes | 2788 |
| WT | mutant | Yes | 38 |

The synthetic target was present at a concentration of 1.0 nM.

The four samples of Table 17 include two blanks (to determine the level of background obtained with probes in the absence of target) and tests of the wild-type and mutant probes against the described synthetic target. The probe mixes contained the capture probe and either the wild-type detector probe (WT) or the mutant detector probe (mutant). The two blanks gave low readings, consistent with output from a DNA sample with no BRCA1 target. The sample readings show that only wild-type probes hybridized effectively to (and produced a signal from) wild-type BRCAI target. The mutant detection probes gave results no higher than background under these conditions.

5.9.6 Electrochemical Detection of BRCA1 from Genomic DNA

Experiments showed that BRCAI gene sequences could be amplified directly from genomic DNA (gDNA) and detected directly, without subsequent manipulations (no external probes used) (see Table 18). For these experiments, different amounts of gDNA (1.56 ng to 100 ng) were amplified with two modified primers; a 5'-biotinylated forward PCR primer (BRCA1-EXII-324-5'B) and 5'-fluoresceinated reverse PCR primer (BRCA1-EXII-620-5'F1) which, after PCR, yield a double-labeled '320 bp fragment (see Table 19). Agarose gel electrophoresis of the PCR products confirmed that the reaction was specific in that only the 320 bp product was formed by PCR. This product was not present in samples that included all the reactants except gDNA target (0 gDNA), whereas increasing amounts of PCR product were visible on the same gel from reactions with increasing amounts of input gDNA. This 320 bp PCR product was captured and detected directly on the sensor.

No visible product by electrophoresis and a low background signal (0.173 µA) was obtained when no gDNA was added to the PCR reaction. A direct signal response was obtained proportional to the amount of gDNA target in the PCR reaction. Exon 11 of BRCA1 is 3400 bp in length. The haploid human genome is $3.3 \times 10^9$ bp. BRCA1 exon 11 therefore represents $1/1.03 \times 10^{-6}$th of the human genome. The highest amount of genomic DNA input to the PCR reaction was 50 ng. At 50 ng input DNA, the biosensor is able to detect the equivalent of 0.1 pg DNA target in 100 ng of heterologous DNA. Studies have also shown that the BRCA I gene may be detected in 5 ng of gDNA. This is equivalent to 5 fg of BRCA1 exon 11.

TABLE 18

Direct response obtained with gDNA BRCAI target

| Target (ng of gDNA) | Current (nA) |
|---|---|
| 1.5 | 400 |
| 3 | 650 |
| 5.5 | 1200 |
| 25 | 1350 |
| 50 | 2300 |

TABLE 19

Primers and Probes Used in Detection of BRCA1 Sequences

| PCR Primers | Sequence (5' to 3') | Modification |
|---|---|---|
| BRCA1 | | |
| BRCA1-EX11-284 | ATAACAGATGGGCTGGAAGTA (SEQ ID NO:12) | NONE |
| BRCA1-EX 11-284-5'B | ATAACAGATGGGCTGGAAGTA (SEQ ID NO:13) | 5' BIOTIN |
| BRCA1-EX11-324 | GCGGACTCCCAGCACAGAA (SEQ ID NO:14) | NONE |
| BRCA1-EX11-324-5'B | GCGGACTCCCAGCACAGAA (SEQ ID NO:15) | 5' BIOTIN |
| BRCA1-EX11-451-5'Fl | TTTCTGAATGCTGCTATTTAGTGT (SEQ ID NO:16) | 5' FLUORESCEIN |
| BRCA1-EX11-451-5'PO$_4$ | TTTCTGAATGCTGCTATTTAGTGT (SEQ ID NO:17) | 5' PHOSPHATE |
| BRCA1-EX11-620-5'Fl | CATGAGGATCACTGGCCAGTAAGT (SEQ ID NO:18) | 5' FLUORESCEIN |
| BRCA1-ES11-620-5'PO$_4$ | CATGAGGATCACTGGCCAGTAAGT (SEQ ID NO:19) | 5' PHOSPHATE |
| BRCA1-EX11-T7-A-For | GATAATACGACTCACTATAGGGTTTTTGAGTA CCTTGTTATTT (SEQ ID NO:20) | |
| BRCA1-EX11-SP6-A-Rev | GATTTAGGTGACACTATAGAACGTTTGGTTAG TTCCCTGATT (SEQ ID NO:21) | |

TABLE 19-continued

Primers and Probes Used in Detection of BRCA1 Sequences

*p53*

| | | |
|---|---|---|
| p53#1-S-5'B | CCTGAGGTGTAGACGCCAACTCTCT (SEQ ID NO:22) | 5' BIOTIN |
| p53#1-AS-5'PO$_4$ | ACTTTGCACATCTCATGGGGTTAT (SEQ ID NO:23) | 5' PHOSPHATE |

| Capture Probes | Sequence | Modification |
|---|---|---|
| *BRCA1* | | |
| BRCA1-EX11-284-5'B | ATAACAGATGGGCTGGAAGTA (SEQ ID NO:24) | 5' BIOTIN |
| BRCA1-EX11-324-5'B | GCGGACTCCCAGCACAGAA (SEQ ID NO:25) | 5' BIOTIN |
| BRCA1-360-3'B | CATTCTTTTCTCTCACACAGGGGATCAGCA (SEQ ID NO:26) | 5' BIOTIN |
| BRCA1-360-352-5'B | CATTCTTTTCTCTCACACA (SEQ ID NO:27) | 5' BIOTIN |
| *p53* | | |
| p53#1-S-5'B | CCTGAGGTGTAGACGCCAACTCTCT (SEQ ID NO:28) | 5' BIOTIN |
| p53cap-13055-5'B | CATCTTGTTGAGGGCAGGGGAGTA (SEQ ID NO:29) | 5' BIOTIN |

| Detector Probes | Sequence | Modification |
|---|---|---|
| *BRCA1* | | |
| BRCA1-WT-400-3'Fl | ATCTCTAGGATTCTCTGAGCATGGCAGTT (SEQ ID NO:30) | 3' FLUORESCEIN |
| BRCA1-Lund8-400-3'Fl | ACATCTTCAGTATCTCTAGCATGGCAGTTT (SEQ ID NO:31) | 3' FLUORESCEIN |
| BRCA1-WT-408-5'Fl | CTCTAGGATTCTCTGAGCAT (SEQ ID NO:32) | 5' FLUORESCEIN |
| BRCA1-Lund8-414-5'Fl | CAGTATCTCTAGCATGGCAG (SEQ ID NO:33) | 5' FLUORESCEIN |
| BRCA1-WT-517-5'Fl | AGACTCCCCATCATGT (SEQ ID NO:34) | 5' FLUORESCEIN |
| BRCA1-Dg-517-5'Fl | AGACTCCCATCATGT (SEQ ID NO:35) | 5' FLUORESCEIN |
| BRCA1-EX11-620-5'Fl | CATGAGGATCACTGGCCAGTAAGT (SEQ ID NO:36) | 5' FLUORESCEIN |
| *p53* | | |
| p53det-13168-5'Fl | TCATGTGCTGTGACTGCTTG (SEQ ID NO:37) | 5' FLUORESCEIN |

Underlined sequence in BRCA 1 detector probes indicates nucleotides deleted in corresponding mutant.

5.9.7 Electrochemical Detection of Plasmid DNA Using Single Probe Method

In clinical detection applications, there will be tests where greater specificity is needed than that obtained by direct detection of a PCR product (see FIG. 6). In such cases, it may be preferable to chose a simple assay which allows additional sequence discrimination. This would be the case for example where it is difficult to create PCR primers that distinguish between WT and mutant.

PCR amplification primers were designed to flank the region of interest. The forward primer was 5'-biotinylated while the reverse primer carried a 5'-phosphate group. The PCR product was digested by Lambda exonuclease to degrade the phosphate-modified strand, leaving a single-stranded target available for subsequent hybridization (see FIG. 13). The single-stranded DNA target was the de facto capture probe, by virtue of the 5'-biotin label incorporated during PCR. This strand was captured onto the sensor and followed by hybridization with discriminating detector probes.

BRCA1 WT and Lund8 mutant plasmid clones (Ambion, Austin, Tex.) were amplified using a 5'-biotinylated forward PCR primer (BRCA1-EX11-324-5'B) and 5'-phosphate modified reverse PCR primer (BRCA1-EX11-620-5'PO$_4$). PCR amplification of the WT plasmid yielded a biotin-labeled 320 bp fragment. The 11-bp deletion of the Lund8 mutant plasmid has an 11-bp reduction in the size of the PCR product of this mutation, for a product of only 309 bp. Following Lambda exonuclease digestion, both products were hybridized with a discriminating detector probe that bound only to WT BRCA1 (BRCAI-WT-408-5'FI). The sensors were washed to remove any unbound detector probe, the open sandwich (single-probe) hybrids were conjugated with anti-FI-HRP antibody. Detection performed as described.

In these experiments, a 17-fold difference in signal was obtained between WT and Lund8 mutant plasmid, consistent with good discrimination between WT and mutant. These data indicate that single-probe hybrids can be used in applications where an additional round of selectivity between WT and mutant is preferably used instead of direct detection products, or where it is not possible to develop distinguishing PCR primers.

5.9.8 Electrochemical Detection of an 11 Base Pair Deletion in BRCA1

In this example, gDNA was obtained from an individual heterozygous for an 11-bp deletion of the BRCA1 gene (Lund8, provided by Dr. Åke Borg, Lund, Sweden). As in the experiments for the detection of the corresponding plasmid DNAs, genomic DNA was amplified by PCR, Lambda exonuclease digested, the biotin-labeled strand captured on the sensor through avidin:biotin interaction and hybridized with the discriminating detector probes. After moderately stringent washes (2×SSC, 55° C.), the captured hybrid was measured electrochemically.

The results shown in Table 20 below confirmed the ability to determine the genotype of an individual with a large deletion mutation in the BRCAI gene. The signal with WT probe from the WT individual (two copies of BRCAI, WT/WT) is approximately twice that of the LundS affected individual. This is the expected result for a heterozygous patient (one copy wild-type, one copy Lund8, WT/Lund8). In contrast, the signal with the Lund8 mutant probe is low in the unaffected individual, as expected for an individual with no deletion in either gene copy. However, in the heterozygous Lund8 carrier, the signal with the mutant probe is significantly elevated. It is anticipated that the signal from the mutant probes will be elevated in an individual carrying the mutation. Taken together, these data show that one may predict the genotype of an individual with respect to the given mutation using hybridization to mutation specific probes in the presence of appropriate controls.

TABLE 20

Electrochemical Detection of an 11 base pair Deletion in BRCA1

| Genotype | Current (nA) with WT probe | Current (nA) with Mutant probe |
| --- | --- | --- |
| WT/WT | 3,800 | 900 |
| WT/Lund8 | 2,700 | 5,100 |

5.9.9 Electrochemical Detection of a Single Base Deletion in BRCA1

Although discrimination of some mutations is relatively straightforward (for example large deletions/insertions) detection of point mutations can be more difficult. The example is illustrated with a single-base deletion, 1323dG. This mutation is a single base deletion of a guanine nucleotide at nt 1323 of the BRCAI gene mRNA. Unfortunately, this deletion falls within a string of four G nucleotides in the wild-type sequence. This leads to several problems, First, allele-specific amplification is not possible, because the 3' nucleotide of an allele specific primer would have to be cytosine to distinguish the presence/absence of a G. However, because of the remaining three G in that string, a primer ending in C would not act as a distinguishing primer. As a result, direct detection of the mutation using a biotinylated forward PCR primer and fluoresceinated reverse PCR primer was not possible with this sequence. Distinguishing detector probes were therefore designed for detection of the single base deletion. These were based on consideration of the thermodynamic properties of each half of the probe (5' to the deletion and 3' to the deletion).

```
BRCAI-WT-517-5'F1
GAC TCC CCA TCA TGT (SEQ ID NO:8)

BRCAI-dG-517-5'F1
AGA CTC CCA TCA TGT (SEQ ID NO:9)
```

The discriminating nucleotide is underlined and is in the exact center of the WT probe. The small size of the probes reduce the chance that a mismatched hybrid will survive elevated temperature hybridization and wash conditions. Results using these small probes showed that they discriminated well between wild-type and mutant DNA in the (see Table 23) hybridizations.

For these experiments, gDNA from an individual heterozygous for a single-point deletion, 1323dG (Coriell Institute for Medical Research, Camden N.J.) and wild-type gDNA were amplified by PCR using the primers; BRCAI-EX11-324-5'B and BRCAI-EX11-620-5'PO$_4$. After amplification, Lambda exonuclease digestion was performed to generate single-stranded nucleic acid which was captured by hybridizing to a probe attached to the surface of a colloidal gold electrode. Samples were then hybridized with the wild-type (BRCAI-WT-517-5'FI) or dG mutant (BRCAI-dG-517-5FI) detector probes. The results are shown in the Table 21 below.

TABLE 21

Electrochemical Detection of a Single Base Deletion in BRCA1

| Genotype | Current (nA) with WT probe | Current (nA) with Mutant probe |
| --- | --- | --- |
| WT/WT | 4,600 | 250 |
| WT/1323dG | 1,650 | 1,300 |

The WT probing of the WT/WT target gave a large electrochemical signal, indicating that it was readily detected. When probed with the mutant gene probe, DNA from the unaffected individual gave a signal no greater than background, indicating no mutant gene present. This confirmed that the genotype of this individual is homozygous wild-type.

In the normal individual the signal obtained with the wild-type BRCAI probe was high, but drops approximately two-fold in the carrier. This was expected, since the normal individual had two copies of the wild-type gene but the heterozygous individual had only one copy. In contrast, the mutant probe gave a much higher signal for the heterozygous carrier than for the WT/WT target, clearly indicating the presence of the 1323 dG mutation. In addition, the ratio of wild-type signal to mutant probe signal in the carrier was close to 1:1, as predicted from the genotype (1 copy wild-type gene: 1 copy mutant gene).

The data show that electrochemical detection of a single-base deletion both qualitatively and quantitatively provides an excellent assay of genotype. The test allowed detection of a single base deletion in a complex sequence in a heterozygous individual. To summarize, data were obtained on detection of two mutations in the BRCA1 gene from gDNA, a large (11-bp) deletion and a small (1-bp) deletion. In both cases, signals from WT probing of the homozygous wild-type individual were high, whereas mutant probing of this individual's DNA gave signals that were much lower indicating the absence of a mutant allele. WT and mutant probing of the heterozygous individuals' gDNAs both gave high signals indicating the presence of both WT and mutant genes (the heterozygous state) in both individuals.

5.10 Detection of Point Mutations

5.10.1 Factor V Tests

Activated protein C resistance is the result of a point mutation (G1691A) in the gene encoding Factor V. This mutation may lead to venous thrombosis in at-risk individuals, particularly those about to undergo surgery or women using oral contraceptives. Knowing the Factor V status of a patient would be a contra-indicator for use of oral contraceptives. Prophylactic treatment with anti-coagulants would prevent clotting episodes in surgical :D patients with one or two copies of the Factor V mutant gene.

Techniques for allele-specific amplification of Factor V wild-type and mutant genes have been described (Kirschbaum and Foster, 1995). Therefore, initial experiments were aimed at repeating, the allele-specific amplification of Factor V genes, followed with electrochemical detection using our direct detection methodology. The forward primer has the same sequence as that reported by Kirschbaum and Foster, except that it is labeled with a biotin at the 5'-end. Two discriminating reverse primers have the same sequences as those reported by Kirschbaum and Foster, but are modified with a 5'-fluorescein. These primers are discriminatory based on identity of the 3'-nucleotide with either the wild-type or the mutant Factor V gene sequence. PCR amplification was performed as described by Kirschbaum and Foster, and amplification products were captured directly onto sensors through the biotin:avidin interaction as described. The double-stranded DNA was conjugated with anti-fluorescein HRP, washed and treated with the substrate and mediator to generate a current. PCR amplification products will also be monitored by agarose gel electrophoresis to confirm that double-stranded products generated are of the predicted size. Null DNA controls and controls of known genotype will be included as well. A high signal from normal individuals is expected with only a background signal from homozygous carriers. After conditions for amplification and assay have been determined for Factor V, various types of samples will be tested. Samples from individuals known to be normal for the Factor V gene mutation, heterozygous for the mutation and homozygous for the mutation (provided by L. Silverman) were analyzed. In a blind study the genotype at the factor V locus was correctly determined in 19 samples.

5.10.2 Measurement of Extracellular Mutated K-ras Sequences in Plasma as a Tumor Marker Detection of mutated K-ras DNA in plasma of patients with pancreatic or other carcinoma may allow early clinical diagnosis of tumor metastasis (Sorenson et al., 1994).

As, noted earlier in relation to Factor V, allele-specific amplification (ASA) techniques exist that may be useful for detection of K-ras sequences in plasma (Rhodes et al., 1997). Therefore, these previously determined conditions for PCR amplification of K-ras sequences could be adapted for use with the disclosed electrochemical direct detection methodology. By analogy to the proposed methods for Factor V, 5'-biotinylated and 5'-fluoresceinated primers could be used to amplify wild-type or mutated K-ras DNA from plasma. The double-stranded products could be captured directly to sensors, followed by conjugation with anti-fluorescein HRP and detection using the substrate and mediator.

Given the difficulty of the proposed assay for mutated K-ras DNA, it may become important to use the power of PCR to generate as much of the K-ras target as possible (to increase sensitivity) without its allele-specific component. In this case, primers flanking the region of interest would be chosen to amplify both wild-type and mutant targets. One primer will be 5'-biotinylated while the other would be modified with a 5'-phosphate. After amplification, the double-stranded target would be converted to a single-stranded target by Lambda exonuclease. The target is captured through the biotin-avidin interaction to the sensor, then hybridized with a specific K-ras probe. This probe would detect either the wild-type or the mutant gene and would carry a fluorescein tag. Detection would be carried out as Inn in similar experiments. This methodology has the possibility of being more sensitive than ASA while maintaining (or even improving) the specificity of the assay.

Although the original assays were designed for the detection of a single mutation, detection of multiple mutations on a single target may eventually be of interest. In such a case, PCR amplification of the target is performed using primers flanking the region(s) of interest. One of these primers is unmodified, while the second primer is modified with a 5% phosphate. As described, the PCR product is digested with Lambda exonuclease to degrade the second strand. In this scenario, discriminating capture and detector probes are used to distinguish between two mutations (A&B) in four states; no mutation, mutation A only, mutation B only, or both mutations. The quantitative aspect of electrochemical assays allows distinguishing between one and two copies (homozygous or heterozygous) for each mutation. The sandwich hybridization technology allows expanding the assay to test for two mutations on a single molecule, even in the absence of any sensor modifications.

5.10.3 CD44 Gene as a Model System for Electrochemical Detection of Messenger RNA in the Early Diagnosis of Cancer The CD44 gene encodes a family of transmembrane glycoproteins that differ in amino acid sequence depending on the program of RNA splicing. The function of the different CD44 proteins is unknown although the pattern of expression is specific for different types of tissue. Recently it has also been shown that the pattern of expression for both CD44 mRNA and protein differs dramatically between normal and tumor tissues from a variety of malignancies (Woodman et al., 1996 and references therein). Therefore, CD44 may serve as a useful early indicator of disease.

The CD44 gene consists of at least 21 exons. Only 10 of these exons are expressed constitutively and encode a standard form of CD44 protein found in nearly all cell types. Cell-type specific forms of CD44 protein are translated from messenger RNA which contain one or more of the remaining 11 variant exons. The messenger RNAs for variant proteins are produced by alternative splicing of the primary RNA transcript. Woodman et al., 1996 used RT-PCR and Southern blot analysis to compare CD44 mRNA profiles in both normal and tumor tissues. Their findings and those of others (Sugiama et al., 1995; Tempfer et al., 1996) indicate that expression of the variant CD44 mRNA's are correlated with the malignant state.

Cell lines from tumors such as breast carcinoma which are known to express variant CD44 mRNA (Woodman et al., 1996) may be obtained from the American Type Culture Collection and used as a source of mRNA. Oligonucleotide primers that recognize standard exons which flank the variant exons may be used to amplify CD44 mRNA using RT-PCR or an isothermal amplification strategy. Unique probes recognizing either the standard exons or the variant exons can be designed and used to discriminate between the different classes of mRNA. Two approaches can be taken to detect the standard versus the variant CD44 mRNAs. A capture probe homologous to the standard region can be used to capture all species of CD44 mRNA. This can be followed by hybridization with the variant-specific detector probe to determine the identity of the mRNA on the sensor.

5.11 Amplification of BRCA1 Gene Using PESA

A unique fragment of the human BRCA1 gene was amplified by PCR™ using an unmodified forward primer and a 5'-phosphate-labeled reverse primer. The product of the reaction was a single fragment of 527 base-pairs having an unmodified top strand and a 5'-phosphate tagged bottom strand. The product was purified from residual PCR™ reactants using a commercial kit (QIAQuick™, Qiagen, Inc., Chatsworth, Calif.) and quantitated by measurement of the absorbance at 260 nm.

The bottom strand of the PCR™ product was removed by digestion with λ exonuclease and the product (10 nM) combined with 67 mM glycine, pH 9.3, 2 mM $MgCl_2$, 1 μλ exonuclease (Boehringer-Manhheim, Indianapolis, Ind.). The reaction mixture was incubated at room temperature for 10 minutes.

The single-stranded DNA target resulting from the lambda exonuclease digestion was combined in hybridization reactions containing 67 pM DNA, 50 mM Tris-HCl pH 7.5, 0.1 M NaCl, 0.2 mM EDTA, 0.05% Bovine serum albumin and 50 nM BRCA1 capture probe (5'-biotin-ATAC-CTTATTCCATTCTTTT-3' SEQ ID NO: 14). Control reactions performed without primer extension signal amplification (PESA) also contained BRCA1 detector probe (5'-fluorescein-ATCTCTAGGATTCTCTGAGCATGGCAGTTT-3' SEQ ID NO:15).

Negative control reaction mixtures contained no target DNA. All reaction mixtures were heated to 80'C for 5 min. and then cooled at room temperature for 10 min. Triplicate aliquots (50 μl) of each sample were applied to the electrochemical sensors that were coated with colloidal gold NeutrAvidin and incubated at room temperature for 20 min. Unbound material was washed from the surface of the sensor with a buffer containing 50 mM Tris-HCl, pH 7.5, 150 mM NaCl, 2 mM EDTA, 0.1% Tween 20.

Twenty microliters of a solution containing 50 mM Tris-HCl pH 7.13, 2.5 μM dGTP, 2.5 μM dATP, 2.5 μM dCTP, 5 μM Fluorescein-dUTP, 0.1 mM dithiothreitol, 0.5 Units Klenow enzyme, 10 mM $MgCl_2$, and 0.2 mg/mL bovine serum albumin was applied to each sensor and incubated at room temperature for 10 min. The sensors were washed as described above and then subjected to electrochemical detection following an incubation with anti-fluorescein-HRP conjugate. Alternatively, detection may be accomplished using specific antibodies that recognize double-stranded DNA or DNA:RNA hybrids or by direct electrochemical detection.

FIG. 16 and FIG. 17 show a comparison of electrochemical detection of DNA with electrochemical detection after primer extension. The figure indicates an approximately 5-fold amplification in signal in detecting a 285-bp fragment of BRCA1 gene which represents detection of 60,000 (or 30,000 diploid cells) molecules of target DNA.

5.12 Detection of Messenger RNA (mRNA)

A direct detection method is used to measure mRNA without amplification. Two probes specific for a target sequence are selected exemplified by a biotinylated capture probe and a fluoresceinated detector probe. The target is hybridized with both probes, captured on a sensor, labeled with enzyme using anti-fluorescein HRP conjugate and electrochemically measured following addition of HRP substrate and a mediator. The method detects mRNA in low copy number in 0.1 μg total from tissues or cells. This is approximately 1 molecule of specific mRNA in 1,000,000 molecules of mRNA.

The measurement of ApoA1 mRNA expressed in cultured hepatocellular carcinoma cells was used as an example of direct detection of specific mRNA (FIG. 17). Total RNA was combined in hybridization reactions with capture and detector probes specific for ApoA1 mRNA. Hybrids were captured on sensors and measured electrochemically as described earlier (FIG. 4). A moderately abundant mRNA (0.1%) was easily detected (two-fold signal-to-noise ratio) in 1 μg of total RNA. When two probes (capture and detector) were present, the sensor detected the AjpoA1 target (squares). When only one probe (detector) was present, sensor response (circles) is equivalent to the blank response obtained when no probes are present (triangles).

All of the compositions, methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

5.13 Detection of Messenger RNA with PESA

The liver-specific mRNA for ApoA1 was specifically detected in total RNA isolated from the hepatocellular carcinoma cell line, HepG2. Total RNA was combined with an ApoA1-specific biotinylated capture probe and the hybrids were bound to the surface of NeutrAvidin-coated electrochemical sensors (FIG. 14). After a brief wash, the sensors were subjected to treatment with a PESA solution containing reverse transcriptase and the precursors for DNA synthesis, including fluorescein-labeled dUTP. Hybrids forming the appropriate primer-template for DNA synthesis were extended during incubation with the solution resulting in target-dependent synthesis and incorporation of many fluorescein labels for each target. The improved electrochemical assay permits reliable detection of ApoA1 mRNA in between 0.1 and 0.2 μg of total RNA (FIG. 18). The signal to noise ratio at the 0.2 μg RNA level is 2.1. This data also demonstrates that the linearity of the electrochemical detection methodology using PESA extends well into the range needed for sensitive detection of mRNA. An alternative form of PESA can include two probes, a capture probe and a primer probe. In this configuration the capture probe would serve only to capture the target on the surface of the sensor in a sequence-specific fashion, and would require a blocked 3'-end such that it could not also serve as a primer. The primer probe is designed such that after annealing to a specific sequence in the target a primer-template competent for DNA synthesis is formed.

6.0 REFERENCES

The following references, to the extent that they provide exemplary procedural or other details supplementary to those set forth herein, are specifically incorporated herein by reference.

U.S. Pat. No. 5,217,594.
U.S. Pat. No. 5,225,064.
U.S. Pat. No. 5,334,296.
U.S. Pat. No. 5,368,707.
U.S. Pat. No. 5,3191,272.
Albretsen, Kalland, Haukanes, Hdvarstein, and Kleppe, *Anal. Biochem.* 189:40–50, 1990.
Aliltalo, In: Bradshaw, R. A., Prentis, S. (eds) *Oncogenes and Growth Factors*, pp. 17–23), Elsevier, Amsterdam, 1987.
Anderson, *Introduction to Microbiology*, The C. V. Mosby Co., St. Louis, 1973.
Baird, Anderson, Newcombe, Lowry, *Am. J Hum. Genet.* 42:677, 1988.
Benn, Soper, Eisenberg et al., "Utility of Molecular genetic analysis of the arrangement of the diagnosis of chronic myelold leukemia," *Cancer Gent Cytogenet,* 29:1–7, 1987.
Bonnard, Papermaster, Kraehenbuhl, *Immunolabeling for Electron Microscopy*, Polak, J., Vamdell, I. M., Eds., Elsevier, Amsterdam, 95–111, 1984.
Bosch et al. "Non isotopic autornatable molecular procedures for the detection of enteroviruses," *Molecular and Cellular Probes,* 10: 81–89, 1996.
Brown, Abramovitz, Bright, Flavin, Gardner, Kane, Platt, Postel, Roodman, Saches, and Starke, *State of the World 1996,* W. W. Norton & Co., New York, 1996.
Carpenter, *Microbiology*, W. B. Saunders Co., Philadelphia, Pa., 1977.
Crumbliss, Henkens Kitchell, Perine, Stonehuemer, Tubergen, "Amperometric Glucose Sensor Fabricated From Glucose Oxidase and a Mediator Co-Immobilized on a Colloidal Gold Hydrogel Electrode," *Biosensor Technology; Fundamentals and Application,* E. F. Bowden, R. Buck, W. E. Hatfield and M. Umana, Eds., Marcel Dekker Publ. Co., NY, Chap. 13, 1990.
Crumbliss, O'Daly, Penine, Stonehuemer, Tubergen, Zhao, Henkens, "Colloidal Gold as a C; Biocompatible Immobilization Matrix Suitable for the Fabrication of Enzyme Electrodes by Electrodeposition," *Biotechnology and Bioengineering,* 40:483, 1992.
Crumbliss, Stonehuemer, Henkens, Zhao, and O'Daly, "A Carrageenan Hydrogel Stabilized Colloidal Gold Multi-Enzyme Biosensor Electrode Utilizing Immobilized Horseradish Peroxidase and Cholesterol Oxidase/Cholesterol Esterase to Detect Cholesterol in Serum and Whole Blood," *Biosensors and Bioelectronics,* 8:331–337, 199').
Crumbliss, Zhao, Henkens, O'Daly, "The Use of Inorganic Materials to Control or Maintain Immobilized Enzyme Activity," *New Journal of Chemistry,* 18:327–33)$_9$, 1994.
Flavell, Birfelder, Sanders and Borst, *Eur. J. Biochem.* 47:53) 5–54'), 1974.
Fleischmann, Pons, Rolison, Schmidt, *Ultramicroelectrodes*, Datatech Systems Inc., 1987.
Garrett, *The Coming Plague*, Penguin Books, New York, N.Y., 1994.
Hall and Spiegelman, "Sequence Complementarity of T2-DNA and T-2 Specific RNA," *Proc. Nat[ Acad Sci. USA,* 47: 137–146, 1961.
Hashimoto, Keiko, and Ishimori, "Sequence-Specific gene Detection with a Gold Electrode Modified with DNA Probes and an Electrochemically Active Dye," *Anal. Chem.,* 66:3830–3S33, 1994.
Henkens, Johnston, Nevoret, O'Daly, Stonehuerner, Zhao, "Determination of Lead by its Inhibition of Isocitrate Dehydrogenase and Diagnosis of Lead Poisoning," *Metal Ions in Biology and Medicine,* Eds. J. Anastassopoulou, Ph. Collerly, J. C., Etienne, Th. Theophanides, John Libbey Eurotext, Paris, 2:275–280, 1992a.
Henkens, Kitchell, O'Daly, Perine, Crumbliss, "Bioactive Electrodes Using Metallo-Proteins Attached to Colloidal Gold," *Recl. Trav. Chim. Pays Bas,* 106:298, 1987.
Henkens, O'Daly, Penine, Stonehuerner, Tubergen, Zhao, Crumbliss, "Electrochemistry of Colloidal Gold Supported Oxidase Enzymes," *J Inorg. Biochem.,* 43:120, 1991.
Henkens, Zhao, O'Daly, "Convenient Enzymatic Determination of Trace Mercury in Water," *Metal Ions in Biology and Medicine, Eds*. J. Anastassopoulou, Ph. Collery, J. C. Etienne and Th. Theophanides, John Libbey Eurotext, Paris, 2:3 17–318, 1992b.
Jameson and Hollengerg, *Horm. Metab. Res.* 24:201, 1992.
Johnson, LaCourse, *Analytical Chemistry,* 62:589A–597A, 1990.
Kaufman and Franz, Student Learning *Guide to accompany Biosphere 2000, Protecting our Global Environment*, The Oxford Associates: Oxford, Ohio, 1996.
Keller and Manak, *DNA Probes*, Macmillan: New York, 1–23, 1989.
Kricka, "Labelling and Detection of Nucleic Acids," *Molecular Diagnostics,* 2:26–40, 1993.
Landegren, Kaiser, Caskey, Hood, Science, 242, 229, 1988.
Lowe, "Clinical applications of gene probes in human genetic disease, malignancy, and infectious disease (Review)," *Clin. Chim. Acta.* 157:1–32, 1986.
Millan and Mikkelsen, "Sequence-Selective Biosensor for DNA Based on Electroactive Hybridization Indicators," *Anal. Chem.* 65:2317–2323, 199').
Millan, Saraullo, and Mikkelsen, "Voltammetric DNA Biosensor for Cystic Fibrosis Based on a Modified Carbon Paste Electrode," *Anal. Chem.* 66:2943–2948, 1994.
Moremans, Daneels, and DeMay, "Sensitive colloidal metal (gold or silver) staining of protein blots on nitrocellulose membranes," *Anal. Biochem.,* 145:315–321, 1985.
Nei and Li, *Proc. Nat 7Acad. Sci. U.S.A.,* 76:5269, 1979.
Nottay et al., *J Clin. Microbiol.,* 33:562–571, 1995.
O'Daly, Zhao, Brown and Henkens, "Electrochemical Enzyme Immunoassay for Detection of Toxic Substances," *Enzyme Microb. Technol.,* i4:299–302, 1992.
Parkkinen, Nfa-ntyjdrvi, Syrjdnen and Ranki, *J Med. Virol.* 20:279–288, 1986.
Ranki, Palva, Laaksonen, and Soderlund, *Gene* 21:77–85, 1983.
Rapley and Walker, (eds) *Molecular Diagnostics*, Blackwell Scientific Publications: Cambridge, Mass., 1993.
Saiki, Bugawan, Horn, Mullis, Erlich, *Nature* 324:163–166, 1986.
Skogerboe, *Anal. Chem.* 65:416R, 1993.
Slamon, Godolphine, Jones, Holt, Wong, Keith, Levin, Stuart, Udover, Ullrich, and Press, *Science* 224:707–712, 1989.
Southern, *J Mol. Biol.* 98:503–517, 1975.
Stonehuemer, Zhao, O'Daly, Crumbliss, and Henkens, "Comparison of Colloidal Go4d_Electrode Fabrication Methods: The Preparation of a Horseradish Peroxidase Enzyme Electrode," *Biosensors & Bioelectronics*, 7:421–428, 1992.

Syvdnen, Söderlund, "Nucleic Acid Analyses as Diagnostic Tools," *Molecular Diagnostics*, Chap. 4:50–65, 1993).

The White House; WorldWatch, 1996.

Worldwatch Institute Report on Progress Toward a Sustainable Society, Brown, L. R., Abramovitz, J., Bright, C., Flavin, Q., Gardner, G., Kane, H., Platt, A., Postel, S., Roodman, D., Saches, A. and Starke, L., *State of the World* 1996, W. W. Norton & Co.: New York, 1996.

Wilson, Chan, DeRoo, Vera-Garcia, Johnson, Lane, and Halbert, "Development of a colorimetric, second generation nucleic acid hybridization method for detection of *Salmonella* in foods and a comparison with conventional culture," *J. Food Sci.*, 55: 1 3) 94–13989,1990.

Yogev, Halachmi, Kenny, and Razin, "Distinction of species and strains of mycoplasmas (mollicutes) by genomic DNA fingerprints with an rRNA gene probe," *J. Clin. Microbiol.*, 26:11998–1201, 1988.

Young, Bevan, Johnson, Blomfield, Bromidge, Maitland, and Woodman, *Br. Med. J.* 293: 14–18, 1989.

Zhao, Henkens, Stonehuemer, O'Daly, and Crumbliss, "Direct electron transfer at horseradish peroxidase/colloidal gold modified electrodes," *J. Electroanal. Chem.*, 327:109–19, 1992.

What is claimed is:

1. A battery or AC-powered portable biosensor apparatus comprising:
    a circuit board with a plurality of working and reference electrodes formed thereon;
    a plurality of nucleic acid segments attached to the surface of said plurality of working electrodes that capture nucleic acid targets by hybridization; and
    a monitor for measuring a current produced following hybridization of targets with the nucleic acid segments, said monitor being operably connected so that it controls the electrical potential of the electrodes and records, analyzes and displays the currents generated at the individual electrodes.

2. The portable biosensor apparatus of claim 1 wherein the circuit board is a printed circuit board or a screen printed circuit board or has a combination of printed and screen printed elements.

3. The portable biosensor apparatus of claim 2 further comprising a multiplexed potentiostat to apply electrical potential and to measure the current generated by each of said nucleic acid segments following hybridization to different target nucleic acids.

4. The portable biosensor apparatus of claim 1 wherein the monitor is a continuous or pulse amperometric monitor.

5. The portable biosensor apparatus of claim 4 wherein the amperometric monitor measures the currents generated by the elements of a sensor array with one or more working electrodes associated with a single reference electrode and simultaneously detects and quantitates a plurality of targets.

6. The portable biosensor apparatus of claim 5 wherein the amperometric monitor comprises pulse and intermittent pulse modes.

7. The portable biosensor apparatus of claim 1 further comprising an amperometric monitor operably linked to said plurality of electrodes so that currents at individual working electrodes are independent of each other.

8. The portable biosensor apparatus of claim 1 further comprising a touch memory chip to upload calibration curves and controlling parameters to the monitor.

9. The portable biosensor apparatus of claim 1 further comprising a liquid crystal display and an output port that enables data transfer to an external device.

10. The portable biosensor apparatus of claim 1 further comprising an integrated microprocessor for changing parameters, saving and analyzing data.

11. The portable biosensor apparatus of claim 1 further comprising a single-key start operation.

12. The portable biosensor apparatus of claim 1 wherein the nucleic acid segments are hybridized with single strand DNA generated from an amplified RNA or genomic DNA sample digested with an exonuclease.

13. A battery or AC-powered portable biosensor apparatus comprising:

a circuit board with a plurality of working and reference electrodes formed thereon;

a plurality of nucleic acid segments attached to the surface of said plurality of working electrodes that capture nucleic acid targets by hybridization, wherein each hybrid formed has one or more labels attached that catalytically enhance the current generated following hybridization; and a monitor for measuring the currents produced following hybridization of targets with the nucleic acid segments, said monitor being operably connected so that it controls the electrical potential of the electrodes and records, analyzes and displays the currents generated at the individual electrodes.

14. The biosensor apparatus of claim 13, wherein the nucleic acid segments are hybridized with single strand DNA generated from an amplified RNA or genomic DNA sample digested with an exonuclease.

* * * * *